United States Patent
Oppenheimer et al.

(10) Patent No.: US 7,566,714 B2
(45) Date of Patent: Jul. 28, 2009

(54) METHODS AND COMPOSITIONS FOR THE TREATMENT OF METABOLIC DISORDERS

(75) Inventors: Daniel I. Oppenheimer, Castro Valley, CA (US); Emil D. Kakkis, Novato, CA (US); Fredric D. Price, Bedford, NY (US); Alejandro Dorenbaum, Mill Valley, CA (US); Rudolf Moser, Schaffhausen (CH); Viola Groehn, Dachsen (CH); Thomas Egger, Kempthal (CH); Fritz Blatter, Reinach (CH)

(73) Assignee: Biomarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 11/143,887

(22) Filed: Jun. 1, 2005

(65) Prior Publication Data

US 2006/0040946 A1 Feb. 23, 2006

Related U.S. Application Data

(63) Continuation of application No. 10/991,573, filed on Nov. 17, 2004, now abandoned.

(60) Provisional application No. 60/520,767, filed on Nov. 17, 2003.

(51) Int. Cl.
*A61K 31/495* (2006.01)
(52) U.S. Cl. ...................... 514/249; 514/250
(58) Field of Classification Search ............... 514/183, 514/249, 250
See application file for complete search history.

(56) References Cited

U.S. PATENT DOCUMENTS

| | | | |
|---|---|---|---|
| 2,541,717 A | 2/1951 | Petering et al. | |
| 2,568,685 A | 9/1951 | Petering et al. | |
| 2,603,643 A | 7/1952 | Kirchsteiner et al. | |
| 2,955,110 A | 10/1960 | Patterson et al. | |
| 3,505,329 A | 4/1970 | Weinstock et al. | |
| 4,252,822 A | 2/1981 | Berry et al. | |
| 4,371,514 A | 2/1983 | Nagatsu et al. | |
| 4,540,783 A | 9/1985 | Viscontini | |
| 4,550,109 A | 10/1985 | Folkers et al. | |
| 4,595,752 A | 6/1986 | Azuma et al. | |
| 4,649,197 A | 3/1987 | Uchino et al. | |

(Continued)

FOREIGN PATENT DOCUMENTS

EP 0 108 890 5/1984

(Continued)

OTHER PUBLICATIONS

Blau, et al. 34th EMG Meeting, Zurich, CH, held May 31-Jun. 2, 2002, proceedings published Oct. 2002.*

(Continued)

*Primary Examiner*—Shengjun Wang
*Assistant Examiner*—Timothy E Betton
(74) *Attorney, Agent, or Firm*—Marshall, Gerstein & Borun LLP

(57) ABSTRACT

The present invention is directed to a novel methods and compositions for the therapeutic intervention in hyperphenylalaninemia. More specifically, the specification describes methods and compositions for treating various types of phenylketonurias using compositions comprising BH4. Combination therapies of BH4 and other therapeutic regimens are contemplated.

46 Claims, 20 Drawing Sheets

U.S. PATENT DOCUMENTS

| | | | |
|---|---|---|---|
| 4,713,454 A | 12/1987 | Sakai et al. |
| 4,758,571 A | 7/1988 | Curtius et al. |
| 4,774,244 A | 9/1988 | Curtius et al. |
| 4,778,794 A | 10/1988 | Naruse et al. |
| 4,920,122 A | 4/1990 | Naruse et al. |
| 4,937,342 A | 6/1990 | Kurono et al. |
| 4,943,575 A | 7/1990 | Cremer |
| 5,037,981 A | 8/1991 | Kurono et al. |
| 5,043,446 A | 8/1991 | Kikuchi et al. |
| 5,198,469 A | 3/1993 | Sakata |
| 5,418,192 A | 5/1995 | Borden et al. |
| 5,439,799 A | 8/1995 | Rautenberg et al. |
| 5,449,688 A | 9/1995 | Wahl et al. |
| 5,468,630 A | 11/1995 | Billiar et al. |
| 5,468,772 A | 11/1995 | Xu et al. |
| 5,502,050 A | 3/1996 | Gross |
| 5,554,647 A | 9/1996 | Perricone |
| 5,606,020 A | 2/1997 | Watanabe et al. |
| 5,643,586 A | 7/1997 | Perricone |
| 5,658,565 A | 8/1997 | Billiar et al. |
| 5,744,340 A | 4/1998 | Fossetta et al. |
| 5,753,656 A | 5/1998 | Sakai et al. |
| 5,763,392 A | 6/1998 | Hansen et al. |
| 5,830,461 A | 11/1998 | Billiar et al. |
| 5,846,775 A | 12/1998 | Hillman et al. |
| 5,856,158 A | 1/1999 | Rosazza et al. |
| 5,874,433 A | 2/1999 | Gross |
| 5,877,176 A | 3/1999 | Gross |
| 5,879,690 A | 3/1999 | Perricone |
| 5,880,124 A | 3/1999 | Gross |
| 5,882,908 A | 3/1999 | Billiar et al. |
| 5,902,810 A | 5/1999 | Pfleiderer et al. |
| 5,922,713 A | 7/1999 | Werner |
| 5,932,208 A | 8/1999 | Chedid et al. |
| 5,945,452 A | 8/1999 | Cooke et al. |
| 6,022,879 A | 2/2000 | Crow et al. |
| 6,046,010 A | 4/2000 | Andersson |
| 6,103,230 A | 8/2000 | Billiar et al. |
| 6,117,872 A | 9/2000 | Maxwell et al. |
| 6,153,615 A | 11/2000 | Gross |
| 6,162,806 A | 12/2000 | Arai et al. |
| 6,162,914 A | 12/2000 | Toderi et al. |
| 6,177,280 B1 | 1/2001 | Yan et al. |
| 6,180,597 B1 | 1/2001 | Liao |
| 6,200,758 B1 | 3/2001 | Richardson |
| 6,245,776 B1 | 6/2001 | Skwierczynski et al. |
| 6,251,953 B1 | 6/2001 | Baranowitz |
| 6,274,581 B1 | 8/2001 | Gross |
| 6,288,067 B1 | 9/2001 | Okamura et al. |
| 6,288,535 B1 | 9/2001 | Chass |
| 6,319,905 B1 | 11/2001 | Mandel et al. |
| 6,346,519 B1 | 2/2002 | Petrus |
| 6,410,535 B1 | 6/2002 | Kashiwagi et al. |
| 6,417,205 B1 | 7/2002 | Cooke et al. |
| 6,423,751 B1 | 7/2002 | Liao |
| 6,428,990 B1 | 8/2002 | Mukerji et al. |
| 6,441,038 B1 | 8/2002 | Loder et al. |
| 6,486,168 B1 | 11/2002 | Skwierczynski et al. |
| 6,500,857 B1 | 12/2002 | Perricone |
| 6,537,992 B2 | 3/2003 | Parker |
| 6,544,994 B2 | 4/2003 | Rabelink et al. |
| 6,562,969 B1 | 5/2003 | Robertus et al. |
| 6,576,105 B1 | 6/2003 | Ma |
| 6,617,359 B2 | 9/2003 | Wohlfart et al. |
| 6,649,345 B2 | 11/2003 | Richardson |
| 6,656,925 B2 | 12/2003 | Petrus |
| 6,660,831 B2 | 12/2003 | Fallon |
| 6,689,385 B2 | 2/2004 | Richardson et al. |
| 6,693,094 B2 | 2/2004 | Pearson et al. |
| 6,696,480 B2 | 2/2004 | Liao |
| 6,706,728 B2 | 3/2004 | Hedenstrom et al. |
| 6,749,875 B2 | 6/2004 | Selleck |
| 6,784,178 B2 | 8/2004 | Gross et al. |
| 6,995,158 B2 | 2/2006 | Rabelink et al. |
| 2002/0037284 A1 | 3/2002 | Fallon |
| 2002/0052374 A1 | 5/2002 | Rabelink et al. |
| 2002/0058674 A1 | 5/2002 | Hedenstrom et al. |
| 2002/0061862 A1 | 5/2002 | Billiar et al. |
| 2002/0076782 A1 | 6/2002 | Rosazza et al. |
| 2002/0082261 A1 | 6/2002 | Kashiwagi et al. |
| 2002/0106645 A1 | 8/2002 | Richardson |
| 2002/0119952 A1 | 8/2002 | Petrus |
| 2002/0155445 A1 | 10/2002 | Jarvik |
| 2002/0187958 A1 | 12/2002 | Horrobin et al. |
| 2003/0004125 A1 | 1/2003 | Hirst et al. |
| 2003/0032616 A1 | 2/2003 | Moskowitz et al. |
| 2003/0045543 A1 | 3/2003 | Hedenstrom et al. |
| 2003/0077335 A1 | 4/2003 | Richardson et al. |
| 2003/0078231 A1 | 4/2003 | Wilburn |
| 2003/0124524 A1 | 7/2003 | Kornman et al. |
| 2003/0212135 A1 | 11/2003 | Gross et al. |
| 2003/0216400 A1 | 11/2003 | Rabelink et al. |
| 2003/0232835 A1 | 12/2003 | Ishihara et al. |
| 2004/0002129 A1 | 1/2004 | Hennies et al. |
| 2004/0014167 A1 | 1/2004 | Yabuta et al. |
| 2004/0034030 A1 | 2/2004 | Richardson et al. |
| 2004/0077859 A1 | 4/2004 | Waer et al. |
| 2004/0115182 A1 | 6/2004 | Fallon |
| 2004/0162269 A1 | 8/2004 | Petrus |
| 2006/0035900 A1 | 2/2006 | Moser et al. |
| 2006/0194808 A1 | 8/2006 | Richardson et al. |
| 2006/0211701 A1 | 9/2006 | Muntau-Heger et al. |
| 2008/0146577 A1 | 6/2008 | Matalon et al. |

FOREIGN PATENT DOCUMENTS

| | | |
|---|---|---|
| EP | 0 318 926 | 11/1988 |
| EP | 0 349 204 | 6/1989 |
| EP | 0 488 078 | 6/1992 |
| EP | 0 908 182 | 4/1999 |
| EP | 0 983 765 | 3/2000 |
| EP | 1 314 782 | 5/2003 |
| EP | 1757293 | 2/2007 |
| JP | 59-021685 | 2/1984 |
| JP | 60-204786 | 10/1985 |
| JP | 63063613 | 3/1988 |
| JP | 9157270 | 6/1997 |
| WO | 95/13075 | 5/1995 |
| WO | 95/28377 | 10/1995 |
| WO | 97/44029 | 11/1997 |
| WO | 98/08516 | 3/1998 |
| WO | 99/43325 | 9/1999 |
| WO | 99/47153 | 9/1999 |
| WO | 00/03746 | 1/2000 |
| WO | 00/37653 | 6/2000 |
| WO | 00/56403 | 9/2000 |
| WO | 01/56551 | 8/2001 |
| WO | 02/17898 | 3/2002 |
| WO | 03/072096 | 9/2003 |
| WO | 03/077837 | 9/2003 |
| WO | 03/080063 | 10/2003 |
| WO | 03/084388 | 10/2003 |
| WO | 2004/002404 | 1/2004 |
| WO | 2004/016764 | 2/2004 |
| WO | 2004/017955 | 3/2004 |
| WO | 2004/041169 | 5/2004 |
| WO | 2004/044602 | 5/2004 |
| WO | 2004/058268 | 7/2004 |
| WO | WO 2005/049614 | 6/2005 |
| WO | WO 2005/065018 | 7/2005 |
| WO | WO-2007/007291 | 1/2007 |

OTHER PUBLICATIONS

Schaub et al. Arch Dis Child., 53(8):674-676 (1978).*
Arnold et al., Hyperalaninemia, Department of Pediatrics and Genetics, University of Rochester School of Medicne and Dentistry http://www. emedicine.com/PED/topic1087.htm(2006), pp. 1-8, especially pp. 1 and 5.*
Kure et al. (Tetrahydrobiopterin-responsive phenylalanine hydroxylase deficiency, J. Pediatr (1999); 135: 375-378).*
Kure et al. (Tetrahydrobiopterin therapy of atypical phenylketonuria due to defective dihydrobiopterin biosynthesis, Archives of Disease in Childhood; 1978, 53, 674-676.*
Shintaku et al. Long-term Treatment and Diagnosis of Tetrahydrobiopterin-Responsive Hyperphenylalinemia with a Mutant Phenylalanine Hydroxylase Gene, (2004), vol. 55, No. 3.*
Bonafe et al., Treatable neutrotransmitter deficiency in mild phenylketonuria, Neurology 2001; 57; 908-911, printed p. 1.*
Cerone et al., "Long-term follow-up of a patient with mild tetrahydrobiopterin-responsive phenylketonuria," *Molecular Genetics and Metbolism 2004 US*, 81(2):137-139 (2004).
Database WPI Section Ch, Week 199308 Derwent Publications Ltd., London, GB; AN 1984-155421 & JP 05 009065 B (1993).
International Search Report for PCT/US04/038296, mailed Sep. 28, 2005, from the European Patent Office.
Steinfeld et al., "A hypothesis on the biochemical mechanism of BH4-responsiveness in phenylalanine hydroxylase deficiency", *Amino Acids 2003 Austria*, 25(1):63-68 (2003).
Seashore, M.R., "Tetrahydrobiopterin and dietary restriction in mild phenylketonuria" *New England Journal of Medicine*, 347(26):2094-2095 (2002).
Trefz et al., "Potential Role of Tetrahydrobiopterin in the Treatment of Maternal Phenylketonuria," *Pediatrics*, 112(6): 1566-1569 (2003).
Written Opinion for PCT/US04/038296, mailed Sep. 28, 2005, from the European Patent Office.
Niederwiesser et al., "Atypical phenylketonuria with defective biopterin metabolism. Monotherapy with tetrahydrobiopterin or sepiapterin, screening and study of biosynthesis in man," *European J Pediatrics*, 138(2):110-112 (1982).
Spaapen et al., "Tetrahydrobiopterin-responsive phenylalanine hydroxylase deficiency in Dutch neonates," *J Inherit. Dis.*, 24(3):352-358 (2001).
Schircks Laboratories "Summary of Product Characteristics—Tetrahydrobiopterin 10 mg/50 mg Tablets," dated Jan. 7, 2004.
Belanger-Quintana et al., "Spanish BH4-responsive phenylalanine hydroxylase-deficient patients: Evolution of seven patients on long-term treatment with tetrahydrobiopterin," *Molecular Genetics and Metabolism*, 86:S61-S66 (2005).
Fiege et al, "Plasma tetrahydrobiopterin and its pharmacokinetic following oral adminstration," *Molecular Genetics and Metabolism*, 81:45-51 (2004).
Hennermann et al., "Long-term treatment with tetrahydrobiopterin increases phenylalanine tolerance in children with severe phenotype of phenylketouria," *Molecular Genetics and Metabolism*, 86:S86-90 (2005).
Lambruschini et al., "Clinical and nutritional evaluation of phenylketonuric patients on tetrahydrobiopterin monotherapy," *Molecular Genetics and Metabolism*, 86:S54-S60 (2005).
Mitchell et al., "Tetrahydrobiopterin-responsive phenylketonuria: The New South Wales experience," *Molecular Genetics and Metabolism*, 86:S81-S85 (2005).
Shintaku et al., "Long-Term Treatment and Diagnosis of Tetrahydrobiopterin-Responsive Hyperphenylalaninemia with a Mutant Hydroxylase Gene," *Pediatric Research*, 55:425-430 (2004).
Trefz et al., "Long-term treatment of patients with mild and classical phenylketonuria by tetrahydrobiopterin," *Molecular Genetics and Metabolism* 86:S75-S80 (2005).
Letter from Food and Drug Administration to BioMarin Pharmaceutical regarding Investigational New Drug application No. 69,708 for tetrahydrobiopterin, dated Sep. 27, 2004.
Letter from BioMarin Pharmaceutical to Food and Drug Administration in response to their comments in the Sep. 27, 2004 letter regarding Investigational New Drug application No. 69,708 for tetrahydrobiopterin, dated Oct. 19, 2004.
Bellamy et al., "Oral folate enhances endothelial function in hyperhomocysteinarmic subjects", *Eur. J. Clin. Invest.*, 29(8), pp. 659-662 (1999).
Al Aqeel, et al. "Response of 6-Pyruvoyl-tetrahydrobiopterin Synthase Deficiency to Tetrahydrobiopterin," *J Child Neurology*, 7:S26-S30 (1992).
Blau et al, "Disorders of Tetrahydrobiopterin and Related Biogenic Amines," in Scriver et al., eds, *The Metabolic & Molecular Bases of Inherited Disease*, 8th edition, vol. II (McGraw Hill Medical Publishing Division: New York, 2001), pp. 1725-1776.
Dudesek et al., "Molecular Analysis and Long-Term Follow-Up of Patients with Different Forms of 6-Pyruvoyl-Tetrahydropterin Synthase Deficiency," *Eur J Pediatr*, 160:267-276 (2001).
Niederwieser et al., "'Peripheral' tetrahydrobiopterin deficiency with hyperphenylalaninaemia due to incomplete 6-pyruvoyl tetrahydropterin synthase deficiency or heterozygosity," *Eur J Pediatr*, 146: 228-232 (1987).
Ogawa et al., "A case of 6-pyruvoyl-tetrahydropterin synthase deficiency demonstrates a more significant correlation to L-Dopa dosage with serum prolactinlevels than CSF homovanillic acid levels," *Brain & Development*, 30:82-85 (2008).
Ponzone et al., "Catalytic Activity of Tetrahydrobiopterin in Dihydropteridine Reductase Deficiency and Indications for Treatment," *Pediatric Research*, 33(2): 125-128 (1993).
Shintaku, "Disorders of Tetrahydrobiopterin Metabolism and their Treatment," *Current Drug Metabolism*, 3: 123-131 (2002).
Tanaka, et al., "Early initiation of L-dopa therapy enables stable development of executive function in tetrahydrobiopterin (BH4) deficiency," *Developmental Med & Child Neurology*, 49:372-376 (2007).
Levy et al., Efficacy of saropterin dihydrochloride (tetrahydrobiopterin 6R-BH4) for reduction of phenylalanine concentration in patients with phenylketonuria: a phase III randomised placebo-controlled study. *Lancet*. 370: 504-10 (2007).
Levy et al., Recommendations for evaluation for responsiveness to tetrahyrobiopterin (BH4) in phenylketonuria and its use in treatment. *Mol. Genet. Metab*. 92: 287-91 (2007).
Mattock et al., Expression and activity of the cysteine protease, legumain, is up-regulated in unstable Regions of human atheroclerotic plaques. *Atherosclerosis*. 193 Abstract: S1-5 (2007).
Ponzone et al., Hyperhyenylalaninemia and pterin metabolism in serum and erythrocytes. *Clinica Chemica Acta*. 216: 63-71 (1993).
Shintaku et al., Tetrahydrobiopterin, responsive, hyperphenylalaninemia without biopterin deficency. *Pteridines*. 11: 83-4 (2000).
Zurfluh et al., Pharmacokinetics of orally administered tetrahydrobiopterin in patients with phenylalanine hydroxylase deficiency. *J. Inherit. Metab. Dis.* 29: 725-31 (2006).
Bates, et al., *Medical Administration: The Correct Way*, in Children's Medications- A Parent's Guid, Harvey Whitney Books Company (1996).
Bernegger et al., "High Frequency of Tetradrobiopterin-responsiveness Among Hyperphenylalaninemias: a Study of 1919 Patients Observed from 1988 to 2002," *Molecular Genetics and Metabolism*, 77, pp. 304-313 (2002).
Blau et al., "Disorders of phenylalanine and tetrahydrobiopterin metabolism" In: Blau et al., eds., *Physician's Guide to the Laboratory Diagnosis of Metabolic Diseases*. 2nd ed., Heidelberg: Springer-Verlag, pp. 89-106 (2003).
Blau et al., "Disorders of Tetrahybiopterin and Related Biogenic Amines," *New York: McGraw Hill*, pp. 1725-1776 (2001).
Blau, et al., 34th EMG Meeting, Zurich, CH, held May 31-Jun. 2, 2002, proceedings published Oct. 2002.
Bunout et al., "Effects of supplementation with folic acid and antioxidant vitamins on homocysteine levels of LDL oxidation in coronary patients," *Nutrition*, 16(2), pp. 107-110 (2002).
Christensen et al., "Comparison of epidermal keratinocytes and dermal fibroblasts as potential target cells for somatic gene therapy of phenylketonuria," *Molecular Genetics and Metabolism*, 76, pp. 313-318 (2002).

Christensen et al., "Development of a skin-based metabolic sink for phenylalanine by overexpression of phenylalanine hydroxylase and GTP cyclohdrolase in primary human keratinocytes," *Gene Therapy*, 7, pp. 1971-1978 (2000).

Cosentino et al., "Tetradrobiopterin and Dysfunction of Endothelial Nitric Oxide Synthase in Coronary Arteries," *Circulation*, 91, pp. 139-144 (1995).

Coskun, "Guanosine Triphosphate Cyclohydrolase 1 Deficiency," *The Turkish Journal of Pediatrics*, 41, pp. 231-237 (1999).

Curtius, et al., *Advances in Neurol.* 40: 463-466 (1984).

Curtius, et al., *The Lancet*, 1: 657-658 (1983).

Davis et al., "The auto-oxidation of tetrahydrobopterin" *Eur. J. Biochem.*, 173, pp. 345-351 (1988).

De Vriese et al., "Endothelial dysfunction in diabetes," *British Journal of Pharmacology*, 130, pp. 963-974 (2000).

De Vriese et al., "Mild to moderate hyperhomocysteinaemia in cardiovascular disease," *Acta Cardiol*, 53(6), pp. 337-344 (1998).

DeFily, "Control of microvascular resistant in physiological conditions and reperfusion," *J. Mol Cell Cardiol.*, 30(12), pp. 2547-2554 (1998).

Dhondt et al., "Atypical Cases of Phenylketonuria," *Eur J. Pediatr.*, 146, pp. A38-A43 (1987).

Dhondt et al., "Diagnosis of Variants of Hyperphenylalaninemia By Determination of Pterins in Urine," *Clinica Chimica Acta*, 110, pp. 205-214 (1981).

Dhondt, "Pterin Metabolism in Normal Subjects and Hyperphnylalaninaemic Patients," *J. Inher. Metab. Dis.*, 4, pp. 47-48 (1981).

Dissing, et al., *Acta Neurol. Scand.*, 79: 493-99 (1989).

Doshi et al., "Folate Improves Endothelial Function in Coronary Artery Disease," *Arteriosclerosis, Thrombosis, and Vascular Biology*, 21(1196), pp. 1-16 (2002).

Durand et al, "Folate deficiencies and cardiovascular pathologies," *Clin Chem Lab Med.*, 36(7), pp. 419-419 (1998).

Ellis, *Philos Trans R Soc Lond B Biol Sci.*, 339: 257-261 (1993).

Endres et al., "Atypical Phenylketonuria Due to Biopterin Deficiency," *Helv. Pediat. Acta*, 37, pp. 489-198 (1982).

Erlandsen et al., "A Structural Hypothesis for BH$_4$ Responsiveness in Patients with Mild Forms of Hyperphenylalaninaemia and Phenylketonuria," *J. Inherit. Metab. Dis.*, 24, pp. 213-230 (2001).

Ferraris et al., "Essai de Depistage Indirect Des Deficits En Tetrahydrobiopterine," *Pediatrie*, 42, pp. 549-555 (1987).

Furrer et al., "Trennug der Diastereomeren (6R)- und (6S)-5, 6, 7, 8-Tetrahydro-L-biopterin," *Helvetica Chemica Acta*, 62(8), p. 264 (1979).

Giugliani et al., "Successful Therapy of Hyperphenylalaninemia Due to Defective Tetrahydrobiopterin Metabolism in Two Siblings," *Rev. Brasil. Genet. IX*, 4, pp. 685-692 (1986).

Güttler, "Hyperphenylalaninemia: Diagnosis and Classification of the Various Types of Phenylalanine Hydroxylase Deficiency in Childhood," *Acta Paediatrica Scandinavica Supplement*, p. 280 (1980).

Hájek et al., "Proton in Vivo Spectroscopy of Patients with Hyperphenylalaninaemia," *Neuropediatrics*, 24, pp. 111-112 (1993).

Hanley et al., "Tetrahydrobiopterin and Mild Phenylketonuria," *N. Engl. J. Med.*, 348(17), pp. 1723-1724 (2003).

Heitzer et al., "Tetrahydrobiopterin improves endothelium-dependent vasodilation by increasing nitric oxide activity in patients with Type II diabetes mellitus," *Diabetologia*, 43(11), pp. 1435-1438 (2000).

Hennermann, et al, Society for the Study of Inborn Errors of Metabolism 40th Annual Symposium. Dublin, Ireland, Sep. 3-6, 2002, abstract published in *J. Inherit. Metabl. Dis.*, Suppl 1: 1-184, Jul. 2002.

Hsia et al., "Hyperphentlalanemia," *Metabolism*, 16(2), pp. 99-101 (1967).

Huether et al., "Individual Carboxylic Ester Hydrolases of the Developing Cerebellum, Influence of Experimental Hyperphenylalaninaemia," *Cellular and Molecular Biology*, 28(3), pp. 313-317 (1982).

Hyland et al., "Matters Arising," *Journal of Neurology, Neurosurgery, and Psychiatry*, 50, pp. 242-243 (1987).

Isaacs, *American Druggist*, 216(6): 37-41 (1999).

Katusic, "Vascular endothelial dysfunction: does tetrahydrobiopterin play a role?" *Am J Physiol Heart Circ Physiol*, 281(3), pp. H981-H986 (2001).

Kaufman et al., "Variant Forms of Phenylketonuria," *The Lancet*, pp. 1236-1237 (1976).

Kaufman, "Hepatic Phenylalanine Hydroxylase and PKU", in Buchwald et a.l., "Brain mechanisms in mental retardation: proceedings of a conference in the series on mental retardation sponsored by the National Institute of Child Health and Human Development mental retardation research centers series", NY: Academic Press, pp. 445-458 (1975).

Kaufman, "Phenylketonuria and Its Variants," *Annals of Clinical and Laboratory Science*, 7(2), pp. 1785-1785 (1977).

Kaufman, "Phenylketonuria Due to a Deficiency of Dihydropterdine Reductase," *The New England Journal of Medicine*, 293(16), pp. 785-790 (1975).

Kaufman, "Unsolved Problems in Diagnosis and Therapy of Hyoperhenylalaninemia Caused By Defects in Tetrahydrobiopterin Metabolism," *Journal of Pediatrics*, 109(4), pp. 572-578 (1986).

Koch et al., "Large Neutral Amino Acid Therapy and Phenylketonuria a Promising Approach to Treatment," *Molecular Genetics and Metabolism*, 79, pp. 110-113 (2003).

Kredan et al., "Homocysteine-induced endothelial superoxide anion production is inhibited by tetrahydrobiopterin and folate," *European Heart Journal*, 20, p. 41 (1999).

Kure et al., "Tetrahydrobiopterin-responsive phenylalanine hydroxylase deficiency," *The Journal of Pediatrics*, 135(3), pp. 375-378 (1999).

Laffranchi et al., "Tetrahydrobiopterin synthesis precedes nitric oxide-dependent inhibition of insulin secretion in INS-1 rat pancreatic beta-cells," *Biochem Biophys Res Commun.*, 233(1), pp. 66-70 (1997).

Lang et al., "Homocysteine-Induced Endothelial Superoxide Anion Production Is Inhibited by Tetrahydrobiopterin and Folate," *Circulation*, 100(18), p. 411 (1999).

Lässker et al., "Tetrahydrobiopterin responsiveness in phenylketonuria. Two new cases and a review of molecular genetic findings," *J. Inherit. Metab. Dis*, 25, pp. 65-70 (2002).

Leeming et al., "Relationship Between Plasma and Red Cell Biopterins in Acute and Chronic Hyperphenylalaninaemia," *J. Inher. Metab. Dis.*, 13, pp. 883-887 (1990).

Lindner et al., "Tetrahydrobiopterin Responsiveness in Phenylketonuria Differs between Patients with the Same Genotype," *Molecular Genetics and Metabolism*, 73, pp. 104-106 (2001).

Liu et al., "Study on a Novel Strategy to Treatment of Phenylketonuria" *Art Cells Blood Subs and Immob Biotech*, 30(4), pp. 243-257 (2002).

Lücke, et al., "BH$_4$-Sensitive Hyperphenylalaninemia: New Case and Review of Literature," *Pediatric Neurology*, 28(3) pp. 228-230 (2003).

Lucock, et al., "The Impact of Phenylketonuria on Folate Metabolism," *Molecular Genetics and Metabolism*, 76, pp. 305-312 (2002).

Mabry, "Phenylketonuria: Contemporary Screening and Diagnosis," *Annals of Clinical and Laboratory Science*, 20(6), pp. 392-397 (1990).

Maier et al., "Tetrahydrobiopterin improves endothelial function in patients with coronary artery disease," *J Cardiovasc Pharmacol*, 35(2), pp. 173-178 (2000).

Mallolas et al., "Mutational Spectrum of Phenylalanine Hydroxylase Deficiency in the Population Resident of Catalonia: Gentotype-phenotype Correlation," *Hum. Genet.*, 105, pp. 468-473 (1999).

Matalon et al., "Phenylketonuria: Screening, Treatment and Maternal PKU," *Clinical Biochemistry*, 24, pp. 337-342 (1991).

Matsubara et al., "Improved Diagnosis of Classical vs Atypical Phenylketonuria by Liquid Chromatography," *Clin. Chem*, 30/2, pp. 278-280 (1984).

Matsuura et al., "Highly Stereoselective Procedure for (6R)-Tetrahydrobioterin Cofactor," *Chemistry Letters*, pp. 735-738 (1984).

McCaman et al., "Fluorimetric method for the determination of phenylalanine in serum," *J. Lab. Clin. Med.*, 59, pp. 885-890 (1962).

Meininger et al., "Impaired nitric oxide production in coronary endothelial cells of the spontaneously diabetic BB rat is due to tetrahydrobiopterin deficiency," *Biochem J.*, 349(Pt 1), pp. 353-356 (2000).

Milstein, "Interconversion of 6- and 7-Substituted Tetrahydropterins Via Enzyme-Generated 4a-Hydroxtetrahydropterin Intermediates," *Methods in Enzymology*, 281, pp. 116-123 (1997).

Missiou-Tsagaraki et al., "Phenylketonuria in Greece: 12 Years' Experience," *Journal of Mental Deficiency Research*, 32, pp. 271-287 (1988).

Mohyuddin et al., "Screening for Biopterin Defects Among Hyperphenylalaninemic Patients: Report of a Canadian Program After 3 Years," *Chemistry and Biology of Pteridines*, pp. 243-246 (1986).

Muntau, et al., "Tetrahydrobiopterin as an Alternative Treatment for Mils Phenylketonuria," *New England Journal of Medicine*, 347(26), pp. 2122-2132 (2002).

Nagatsu, *Essays in Biochemistry*, 30: 15-35 (1995).

Nixon et al., "Neopterin and Biopterin Levels in Patients with Atypical Forms of Phenylketonuria," *Journal of Neurochemistry*, 35(4), pp. 898-904 (1980).

Parker, "Diseases of Phenylalanine Metabolism," *Western Journal of Medicine*, 131, pp. 285-197 (1979).

Patterson et al., "The Synthesis of a Pteridine Required for the Growth of Crithidia Fasciculata", 78(22), p. 5868-5871 (1956).

PhenylAde Amino Acid Bars. brochure, Nov. 2002.

PhenylAde Amino Acid Blends brochure, May 2002.

Pieper, "Acute amelioration of diabetic endothelial dysfunction with a derivative of the nitric oxide synthase cofactor, tetrahydrobiopterin," *J Cardiovasc Phamacol*, 29 (1), pp. 8-15 (1997).

Ponzone et al., "Differential Diagnosis of Hyperphenylalaninaemia by a Combined Phenylalanine-tetrahydrobiopterin Loading Test," *Eur J Pediatr*, 152, pp. 655-661 (1993).

Ponzone et al., "Tetrahydriobiopterin Loading Test in Hyperphenlalaninemia," *Pediatric Research*, 30(5), pp. 435-438 (1991).

Primrose, "Phenylketonuria With Normal Intelligence," *J. Ment. Defic. Res.*, 27, pp. 239-246 (1983).

Rabinoff, "Possible Uses of Urinary Neopterin and Biopterin Measurement," *Medical Hypotheses*, 29, pp. 241-243 (1989).

Reddi, "Tissue concentrations of water-soluble vitamins in normal and diabetic rats," *Int J Vitam Nutr Res.*, 63(2), pp. 140-144 (1993).

Rey et al., "Kinetics of Phenylalanine Disapperance After Intravenous Load in Phenylketonuria and Its Genetic Variants," *Pediat. Res.*, 13, pp. 21-25 (1979).

Roth, M.D., "Newborn Metabolic Screening: A Search for "Nature Experiments"," *Current Concepts in Diagnosis*, 79(1), pp. 47-54 (1986).

Schaub et al., *Arch Dis. Child.*, 53(8): 674-676 (1978).

Schircks et al., "Eline neue, regiospezifische Synthese von L-Biopterin," *Helvetica Chimica Acta*, 60(1), p. 24 (1977).

Schlesinger et al., "Urinary Dihydroxanthopterin in the Diagnosis of Malignant Hyperphenylalaninemia and Phenylketonuria," *Clinica Chimica Acta*, 92, pp. 187-195 (1979).

Schmid et al., "The nitric oxide synthase cofactor tetrahydrobiopterin reduces allograft ischemia-reperfusion injury after lung transplantation," *J. Thorac Cardiovasc Surg.*, 118(4), pp. 725-732 (1999).

Schulze et al., "Evaluation of 6-year Application of the Enzymatic Colorimetric Phenylalanine Assay in the Setting of Neonatal Screening for Phenylketonuria," *Clinica Chimica Acta*, 317, pp. 27-37 (2002).

Schutte, Department of Health and Human Services, Pub No. HRS-MCH 89(5), pp. 1-22 (1990).

Scriver et al., "Hyperphenylalanine: Phenylalanine Hydroxylase Deficiency," *New York:McGraw-Hill*, pp. 1667-1724 (2001).

Scriver, "Science, Medicine and Phenylketonuria," *Acta Pardiatr*, 407, pp. 11-18 (1994).

Sharma et al., "Development of a Refractory Stage in a Dog Model for Phenylketonuria," *Research Communications in Chemical Pathology and Pharmacology*, 33(1), pp. 145-153 (1981).

Shaw et al., "Analytical Methods in Phenylketonuria Clinical Biochemistry," in Bickett et al., Eds., *Phenylketonuria and some other Inborn Erris of Amino Acid Metabolism*, Stuttgart: Georg Theim Verlag, 47, pp. 47-56 (1969).

Shimizu et al., "Protective effects of tetrahydrobiopterin against nitric oxide-induced endothelial cell death," *Life Sci.*, 63(18), pp. 1585-1592 (1998).

Shimizu et al., "Role of tetrahydrobiopterin in the function of nitric oxide synthase, and its cytoprotective effect (Review)," *Int J Mole Med.*, 2(5), pp. 533-540 (1998).

Shinozaki et al., "Abnormal Biopterin Metabolism Is a Major Cause of Imparied Endothelium-Dependent Relaxation Through Nitric Oxide/O2-Imbalance in Insulin-Resistant Rat Aorta," *Diabetes*, 48, pp. 2437-2445 (1999).

Shinozaki et al., "Oral Administration of Tetrahydrobiopterin Prevents Endothelial Dysfunction and Vascular Oxidative Stress in The Aortas of Insulin-Resistant Rats," *Circ. Res.*, 87, pp. 566-573 (2000).

Slazyk et al., "Liquid-Chromatographic Measurement of Biopterin and Neopterin in Serum and Urine," *Clinical Chemistry*, 36(7), pp. 1364-1368 (1990).

Smith et al, "Neurological Aspects of Biopterin Metabolism," *Archives of Disease in Childhood*, 61, pp. 130-137 (1986).

Smith et al., "New Variant of Phenylketonuria With Progressive Neurological Illness Unresponsive to Phenylalanine Restriction," *The Lancet*, pp. 1108-1111 (1975).

Spaapen, et al., "Tetrahydrobiopterin-responsive Phenylalanine Hydroxylase Deficiency, State of the Art," *Molecular Genetics and Metabolism*, 78, pp. 93-99 (2003).

Steinfield et al, *Eur. J. Pediatr.*, 161: 403-405 (May 2002).

Stroes et al., "Folic Acid Reverts Dysfunction of Endothelial Nitric Oxide Synthase," *Circ. Res.*, 86, pp. 1129-1134 (2000).

Sugimoto et al., "The Convenient Synthesis of Biopterin and Its Three Optical Isomers," *Bulletin of Chemical Society of Japan*, 48(12), pp. 3767-3768 (1975).

Tada et al., "Follow-up Study of a Nation-wide Neonatal Metabolic Screening Program in Japan," *European Journal of Pediatrics*, 145, pp. 204-207 (1984).

Tanaka et al., "Hyperphenylalaninemia Due to Impaired Dihydrobiopterin Biosynthesis," *European Journal of Pediatrics*, 136, pp. 275-280 (1981).

Taylor et al., "Pteridines. XXXVII. A Total Synthesis of L-erythro-Biopterin and Some Related 6-(Polyhydroxyalkyl)pterins," *J. Am. Chem. Soc.*, 98(8), pp. 2301-2307 (1976).

Thöny et al., "Mutations in the Pterin-4α-carbinolamine Dehydratase (PCBD) Gene Cause a Benign Form of Hyperphenylalaninemia," *Human Genet.*, 103, pp. 162-167 (1998).

Tiefenbacher et al., "Endothelial Dysfunction of Coronary Resistance Arteries Is Improved by Tetrahydrobiopterin in Atherosclerosis," *Circulation*, 102, pp. 2172-2179 (2000).

Treacy et al., "Analysis of Phenylalanine Hydroxylase Genotypes and Hydroxylase Genotypes and Hyperphenylalaninemia Phenotypes Using $_L$-[1-$^{13}$C] Phenylalanine Oxidation Rates in Vivo: A Pilot Study," *International Pediatric Research Foundation, Inc.*, 42(4), pp. 430-435 (1997).

Trefz et al., "Successful treamtent of phenylketonuria by tetrahydrobiopterin," *Eur J Pediatr.*, p. 315 (2001).

Vasquez-Vivar et al., "Superoxide generation by endothelial nitric oxide synthase: The Influence of cofactors," *Proc. Natl. Acad. Sci. USA*, 95, pp. 9220-9225 (1998).

Verhaar et al., "5-Methyltetrahydrofolate, the Active Form of Folic Acid, Restores Endothelial Function in Familial Hypercholesterolemia," *Circulation*, 98, pp. 237-241 (1998).

Verhaar et al., "Effects of Oral Folic Acid Supplementation on Endothelial Function in Familial Hypercholesterolemia," *Circulation*, 100, pp. 335-338 (1999).

Verhaar et al., "Future for folates in cardiovascular disease," *European Journal of Clinical Investigation*, 29, pp. 657-658 (1999).

Verma et al., "Novel Cardioprotective Effects of Tetrahydrobiopterin After Anoxia and Reoxygenation: Identifying Cellular Targets for Phamacologix Manipulation," *The Journal of Thoracic and Cardiovascular Surgery*, 123(6), pp. 1074-1083 (2002).

Villasana et al., "Neurological Deterioration in Adult Phenylketonuria," *J. Inher. Metab. Dis.*, 12, pp. 451-457 (1989).

Viscontini et al., "Eine neue Synthese von D, L-Biopterin," *Helvetica Chemica Acta*, 55(2), pp. 60-61 (1972).

Viscontini et al., "Fluoreszierende Stoffe aus Drosphila Melanogaster," *Helvetica Chimica Acta*, 52(5), p. 131 (1969).

Wachtel, "Review of Current Practices in Management of Inherited Disorders of Amino Acid Metabolism in Western Europe," *Human Nutrition: Applied Nutrition*, 40A(1), pp. 61-69 (1986).

Walter et al., *Am. J. Respir. Crit. Care Med.*, 156(6): 2006-2010 (1997).

Weglage et al., "Tetrahydrobiopterin Responsiveness in a Large Series of Phenylktonuria Patients," *J. Inherit, Metab. Dis.*, 25, pp. 321-322 (2002).

Wever et al., "Atherosclerosis and the Two Faces of Endothelial Nitric Oxide Synthase," *Circulation*, 97, pp. 108-112 (1998).

Wever et al., "Tetrahydrobiopterin regulates superoxide and nitric oxide generation by recombinant endothelial nitric oxide synthase," *Biochem Biophys Res Commun.*, 237(2), pp. 340-344 (1997).

Yoshioka et al., "Atypical Phenylketonuria Due to Biopterin Deficiency: Diagnosis by Assay of an Enzyme Involved in the Synthesis of Sepiapterin from Dihydroneopterin Triphosphate," *Zoological Science*, 1, pp. 74-81 (1984).

\* cited by examiner

METHODS AND COMPOSITIONS FOR THE TREATMENT OF METABOLIC DISORDERS

CROSS-REFERENCE TO RELATED APPLICATION

This application is a continuation of U.S. patent application Ser. No. 10/991,573, which was filed on Nov. 17, 2004 and which claimed the benefit under 35 U.S.C. § 119(e) of U.S. Provisional Patent Application Ser. No. 60/520,767, which was filed Nov. 17, 2003. The entire disclosure of each of these priority applications is hereby incorporated herein by reference.

BACKGROUND

1. Field

The present invention is generally directed to the therapeutic intervention of metabolic disorders, particularly those involving amino acid metabolism. More particularly, the present invention is directed to methods and compositions for the treatment of phenylketonuria, vascular diseases, ischemic or inflammatory diseases, or insulin resistance, or conditions and patients that would benefit from enhancement of nitric oxide synthase activity.

2. Background of the Related Technology

Phenylketonuria (PKU) is an inherited metabolic disorder that was first identified in the 1930s. In most cases, and until the mid-1990s, it was thought that this is a disorder of amino acid metabolism resulting from a deficiency in the liver enzyme phenylalanine hydroxylase (PAH). Deficiencies in PAH in turn result in an excess of phenylalanine (Phe) in the brain and plasma. The deficiency in PAH ultimately manifests in a lack of tyrosine, which is a precursor for the neurotransmitters.

Left undetected and untreated early in the life of an infant, PKU leads to irreversible damage of the nervous system, severe mental retardation and poor brain development. Features other than mental retardation in untreated patients include brain calcification, light pigmentation, peculiarities of gait, stance, and sitting posture, eczema, and epilepsy. It has been reported that an infant suffers a loss of 50 IQ points within the first year of infancy and PKU is invariably accompanied by at least some loss of IQ. Once detected, the condition is treated by providing the infant, and later the child, with a low Phe diet. In adults, the protein supplements routinely taken by classic PKU patients may be Phe-free with the assumption that such adults will receive sufficient quantities of Phe through the remaining diet, controlled under a strict regimen, so that the overall diet is a low Phe diet. Also, pregnant women who suffer from the condition are recommended a diet that is low in Phe to avoid the risk of impairment of the development of the fetus and congenital malformation (maternal PKU syndrome).

In more recent years it has been shown that pathological symptoms which manifest from the condition of excess of Phe, collectively termed hyperphenylalaninemia (HPA), may be divided into multiple discrete disorders, which are diagnosed according to plasma Phe concentrations and responsiveness to a co-factor for PAH. At an initial level, HPAs may be divided into HPA caused as a result of a deficiency in the cofactor 6R-L-erythro-5,6,7,8, tetrahydrobiopterin (BH4; malignant PKU) and HPA resulting from a deficiency in PAH. The latter category is further subdivided into at least three categories depending on the plasma concentration of Phe in the absence of dietary or other therapeutic intervention (referred to herein as "unrestricted plasma Phe concentration").

Normal plasma Phe homeostasis is tightly controlled resulting in a plasma Phe concentration of 60 µmol/L±15 µmol/L. Classical PKU (OMIM No. 261600) is the most severe form of PKU and it results from null or severe mutations in PAH, which lead to unrestricted plasma Phe concentrations greater than 1200 µmol/L when left untreated. Individuals with classical (or severe) PKU must be treated with a strict dietary regimen that is based on a very low Phe diet in order to reduce their Phe concentrations to a safe range. Milder forms of HPA also have been characterized. A less severe form of PKU is one which manifests in plasma Phe concentrations of 10-20 mg/dL (600-1200 µmol/L), and is generally termed "mild PKU". This moderate form of PKU is managed through the use of moderate dietary restrictions, e.g., a low total protein diet, but otherwise not necessarily Phe-free. Finally, mild HPA, also referred to as benign or non-PKU HPA is characterized by plasma Phe concentrations of between 180-600 µmol/L. The individuals with non-PKU HPA are not routinely treated as they are considered to have plasma Phe levels that are within the "safe" range. Nevertheless, as mentioned above, these Phe levels are still significantly elevated in these individuals as compared to normal, non-PKU subjects and may present detrimental sequelae in at least pregnant women and very young patients. For a more detailed review of HPA resulting from PAH deficiency, those of skill in the art are referred to Scriver et al., 2001 (*Hyperphenylalaninemia: Phenylalanine Hydroxylase Deficiency*, In: Scriver C R, Beaudet A L, Sly W S, Valle D, Childs B, Vogelstein B, eds. The Metabolic and Molecular Bases of Inherited Disease. 8th ed. New York: McGraw-Hill, 2001: 1667-1724). NIH Guidelines indicate that for children with PKU, it is preferable reduce the plasma Phe to be 360-420 µmol/L.

HPA also results from defects in BH4 metabolism. BH4 is an essential cofactor of both tyrosine and tryptophan hydroxylase, the rate limiting enzymes in the biosynthesis of the neurotransmitters dopamine and serotonin. The effects of deficiencies in dopamine and serotonin are collectively known as "atypical" or "malignant" HPA. Thus, traditional diagnoses of HPA have involved a determination of whether the HPA is a result of BH4 deficiency or PAH deficiency. Typically, diagnosis of PKU is established on the basis of a persistently elevated blood Phe concentration. Following a positive screen for elevated blood Phe (plasma Phe>120 µmol/L; Weglage et al., *J. Inherit. Metab. Dis.*, 25:321-322, 2002), a differential screen is performed in which it is determined whether the elevated Phe is a result of BH4 deficiency or PAH deficiency. The differential diagnosis involves determining whether the elevated Phe concentration is decreased as a result of BH4 administration (BH4 loading test). The BH4 loading test typically involves a one-time load of BH4 e.g., 5-20 mg/kg being administered to the subject who is on a normal (i.e., unrestricted) diet and determining whether the subject experiences a decrease in Phe levels (see e.g., Ponzone et al., *Eur. J. Pediatr.* 152:655-661, 1993; Weglage et al., *J. Inherit. Metab. Dis.*, 25:321-322, 2002.)

Typically, individuals that respond to a BH4 loading test by a decrease in plasma Phe levels are diagnosed as having a defect in BH4 homeostasis. However, there have been various reports of patients with a BH4 responsive type of PAH deficiency (Kure et al., *J. Pediatr.* 135:375-378, 1999; Lassker et al., *J. Inherit. Metabol. Dis.* 25:65-70, 2002; Linder et al., *Mol. Genet. Metab.* 73:104-106, 2001; Spaapen et al., *Mol. Genet. and Metabolism*, 78:93-99, 2003; Trefz et al., 2001). These subjects have plasma Phe levels that are typical of moderate PKU, i.e., less than 1000 µmol/L and typically less than 600 µmol/L. Patients that have severe classical PKU are not responsive to typical 24 hour BH4 loading tests (Ponzone et al., *N. Engl. J. Med* 348(17):1722-1723, 2003).

It has been suggested that individuals that are responsive to BH4 do not require dietary intervention, but rather should be treated with BH4. Likewise, the converse has been suggested for subjects that have been diagnosed as non-responsive to the BH4 loading test, i.e., these subjects should be treated with dietary restriction and not BH4 therapy. Ponzone et al. particularly noted that individuals that have severe phenylketonuria will not respond to BH4 therapy and such therapy should not be used on these patients (Ponzone et al., *N. Engl. J. Med* 348(17):1722-1723, 2003). Thus, presently there are divergent therapeutic regimens for treatment of HPA depending on whether or not the individual is responsive to BH4. Moreover, it has been suggested that very few patients will benefit from BH4 therapy. In fact, it is thought that the only individuals with a PAH-deficient form of HPA that will benefit from BH4 therapy are those with mild PKU. As these individuals will typically have Phe levels in the safe range (i.e., less than 600 µM), the disease state can be controlled using moderate dietary restriction (see Hanley, *N. Engl. J. Med* 348(17):1723, 2003). Thus, BH4 therapy either alone, or in combination with any other therapeutic intervention, has not being considered as a viable therapeutic intervention for the vast majority of individuals with HPA.

BH4 is a biogenic amine of the naturally-occurring pterin family. Pterins are present in physiological fluids and tissues in reduced and oxidized forms, however, only the 5,6,7,8, tetrahydrobiopterin is biologically active. This is a chiral molecule and the 6R enantiomer of the cofactor is known to be the biologically active enantiomer. For a detailed review of the synthesis and disorders of BH4 see Blau et al., 2001 (*Disorders of tetrahydrobiopterin and related biogenic amines.* In: Scriver C R, Beaudet A L, Sly W S, Valle D, Childs B, Vogelstein B, eds. The Metabolic and Molecular Bases of Inherited Disease. 8th ed. New York: McGraw-Hill, 2001: 1275-1776). Despite the elucidation of the role of BH4 deficiency in HPA, treatment with BH4 has not been suggested because such treatment is very expensive, as high as $30,000 per year for an adolescent or adult, as compared with $6,000 for phenylalanine-restricted dietary therapy (Hanley, *N. Engl. J. Med* 348(17):1723, 2003). Another significant problem with BH4 is that this compound is unstable and readily undergoes aerobic oxidation at room temperature (Davis et al., *Eur. J. Biochem.,* Vol 173, 345-351, 1988; U.S. Pat. No. 4,701,455) and has a shelf-life of less 8 hours at room temperature (Berneggar and Blau, *Mol. Genet. Metabol.* 77:304-313, 2002).

Thus, to date, dietary intervention is the typical therapeutic intervention used for all patients with severe classical PKU and in many patients with moderate PKU. Such dietary intervention typically entails restricting the patient to foodstuff that is composed of natural foods which are free from, or low in, Phe. However, in addition to eliminating Phe, such a dietary regimen eliminates many sources of other essential amino acids, vitamins and minerals. Consequently, without supplementation, such a diet provides inadequate protein, energy, vitamins and minerals to support normal growth and development. As PKU is a manifestation of a lack of tyrosine, which arises due to the lack of hydroxylation of phenylalanine, tyrosine becomes an essential amino acid and dietary supplements for PKU must contain a tyrosine supplement. Therefore, it is common to use nutritional formulas to supplement the diets of PKU patients. Also, for babies, it is common to use infant formulas which have a low Phe content as the sole or primary food source.

However, dietary protein restriction is at best an ineffective way of controlling PKU in many classes of patients. For example, treatment is of paramount importance during pregnancy because high Phe levels may result in intrauterine retardation of brain development. However, a low protein diet during pregnancy may result in retarded renal development and is thought to produce a subsequent reduction in the number of nephrons and potentially leads to hypertension in adulthood. (D'Agostino, *N. Engl. J. Med.* 348(17)1723-1724, 2003).

Poor patient compliance with a protein-restricted diet also is a problem. The Phe-free protein formulae available are bitter tasting making it difficult to ensure that the patient consumes sufficient quantities of the protein to maintain the required daily intakes of protein, amino acids, vitamins, minerals, and the like. This is particularly a problem with older children who may require up to 70 g, dry weight, of the formulas per day. For example, Schuett, V. E.; 1990; DHHS Publication No HRS-MCH-89-5, reports that more than 40% of PKU patients in the US of eight years or older no longer adhere to the dietary treatment. (U.S. Pat. No. 6,506,422). Many adolescent patients fail to rigorously follow the protein-restricted diet due to fears of peer attitude.

Thus, there remains a need for a therapeutic medicament to replace or supplement and alleviate the dietary restrictions under which a PKU patient is placed. The present invention is directed to addressing such a need.

SUMMARY OF THE INVENTION

The invention describes intervention in metabolic disorders, particularly those involving amino acid metabolism. More particularly, the present invention is directed to methods and compositions for the treatment of subjects exhibiting elevated phenylalanine levels, for example, subjects suffering from hyperphenylalanemia, mild phenylketonuria or classic severe phenylketonuria; and methods and compositions for the treatment of subjects suffering from conditions that would benefit from enhancement of nitric oxide synthase activity; and methods and compositions for treatment of subjects suffering from vascular diseases, ischemic or inflammatory diseases, diabetes, or insulin resistance.

In one aspect, the invention describes methods of treating classic severe phenylketonuria (PKU) in a subject comprising administering to the subject a protein-restricted diet in combination with a composition comprising tetrahydrobiopterin (BH4) or a precursor or derivative thereof, wherein the combined administration of the protein-restricted diet and BH4 is effective to lower the phenylalanine concentration in the plasma of the subject as compared to the concentration in the absence of the combined administration. In specific embodiments, the subject is one who does not manifest a deficiency in BH4 homeostasis. The subject may be an individual that does not manifest symptoms of L-dopa neurotransmitter deficiency.

A subject selected from treatment according to the methods of the invention will have an elevated plasma Phe concentration, such a concentration may be greater than 1800 µM/L in the absence of the therapeutic. Other embodiments contemplate that has a plasma phenylalanine concentration of greater than 1000 µM in the absence of a therapeutic regimen. In preferred embodiments, the combined administration methods of the invention decrease the plasma phenylalanine concentration of the subject to less than 600 µM. More preferably, it is decreased to less than 500 µM. Even more preferably, the combined administration decreases the plasma phenylalanine concentration of the subject to 360 µM±15 µM.

The BH4 is preferably administered in an amount of between about 1 mg/kg to about 30 mg/kg, more preferably between about 5 mg/kg to about 30 mg/kg. The BH4 may be administered in a single daily dose or in multiple doses on a daily basis. In some embodiments, the BH4 therapy is not continuous, but rather BH4 is administered on a daily basis until the plasma phenylalanine concentration of the subject is decreased to less than 360 μM. Preferably, wherein the plasma phenylalanine concentration of the subject is monitored on a daily basis and the BH4 is administered when a 10% increase in plasma phenylalanine concentration is observed. Preferably, the BH4 being administered is a stabilized crystallized form of BH4 that has greater stability than non-crystallized stabilized BH4. More preferably, the stabilized crystallized form of BH4 comprises at least 99.5% pure 6R BH4. Precursors such as dihydrobiopterin (BH2), and sepiapterin also may be administered. BH4 may be administered orally The protein-restricted diet administered in the methods herein is one that is a phenylalanine-restricted diet wherein the total phenylalanine intake of the subject is restricted to less than 600 mg per day. In other embodiments, the protein-restricted diet is a phenylalanine-restricted diet wherein the total phenylalanine is restricted to less than 300 mg per day. In still other embodiments, the protein-restricted diet is one which is supplemented with amino acids, such as tyrosine, valine, isoleucine and leucine. In certain embodiments, protein-restricted diet comprises a protein supplement and the BH4 is provided in the same composition as the protein supplement.

In specific embodiments, the subject is one which has been diagnosed as having a mutant phenylalanine hydroxylase (PAH). The mutant PAH may comprise a mutation in the catalytic domain of PAH. Exemplary such mutations include one or more mutations selected from the group consisting of F39L, L48S, I65T, R68S, A104D, S110C, D129G, E178G, V190A, P211T, R241C, R261Q, A300S, L308F, A313T, K320N, A373T, V388M E390G, A395P, P407S, and Y414C.

Also contemplated herein is a method for the treating a pregnant female having hyperphenylalaninemia (HPA) comprising administering to the subject a protein-restricted diet in combination with a composition comprising tetrahydrobiopterin (BH4) or a precursor or derivative thereof, wherein the combined administration of the protein-restricted diet and BH4 is effective to lower the phenylalanine concentration in the plasma of the subject as compared to the concentration in the absence of the combined administration. In certain embodiments, the subject has an unrestricted plasma phenylalanine concentration of greater than 180 μM but less than 600 μM. In other embodiments, the subject has an unrestricted plasma phenylalanine concentration of greater than 500 μM but less than 1200 μM. In still other embodiments, the subject has an unrestricted plasma phenylalanine concentration of greater than 1000 μM.

Also contemplated is a method of treating a patient having above normal concentration of plasma phenylalanine (e.g., greater than 180 μM/L and more preferably, greater than 360 μM/L) comprising administering to the patient a stabilized BH4 composition in an amount effective to produce a decrease in the plasma phenylalanine concentration of the patient. Preferably, the stabilized BH4 composition is stable at room temperature for more than 8 hours. The patient will likely have a plasma phenylalanine concentration greater than 180 μM prior to administration of the BH4. More particularly, the patient has a plasma phenylalanine concentration of between 120 μM and 200 μM. In other embodiments, the patient has a plasma phenylalanine concentration of between 200 μM and 600 μM. In still other embodiments, the patient has a plasma phenylalanine concentration of between 600 μM and 1200 μM. Yet another class of patients to be treated are those that have an unrestricted plasma phenylalanine concentration greater than 1200 μM. In specific embodiments, the patient is an infant, more particularly, an infant having a plasma phenylalanine concentration greater than 1200 μM. In other embodiments, the patient is pregnant and pregnant patient has a plasma phenylalanine concentration of between about 200 μM to about 600 μM. Pregnant patients with a plasma phenylalanine concentration greater than 1200 μM are particularly attractive candidates for this type of therapy, as are patient who are females of child-bearing age that are contemplating pregnancy. In those embodiments, in which the patient has a plasma phenylalanine concentration greater than 1200 μM, and the method further comprises administering a protein-restricted diet to the patient.

The invention also contemplates a method of treating a patient having phenylketonuria, comprising administering to the patient a stabilized BH4 composition in an amount effective to produce a decrease in the plasma phenylalanine concentration of the patient wherein the patient has been diagnosed as unresponsive to a single-dose BH4 loading test. Preferably, the patient is unresponsive within 24 hours of the BH4 load.

Another related aspect of the invention provides a multiple dose loading test that involves administration of more than one dose of BH4. The data described herein demonstrates that subjects who are considered "unresponsive" to a single dose BH4 loading test can respond to multiple doses of BH4 with a significant reduction in phenylalanine levels. In one embodiment, at least two doses of BH4 which may be between about 5 mg to 40 mg are administered to a subject over a time period of more than one day, preferably 7 days.

The treatment methods according to the invention may comprise administering between about 10 mg BH4/kg body weight to about 200 mg BH4/kg body weight. The BH4 may be administered through any route commonly used in practice, e.g., orally, subcutaneously, sublingually, parenterally, per rectum, per and nares. The BH4 may be administered daily or at some other interval, e.g., every alternative day or even weekly. The BH4 is preferably administered in combination with a protein-restricted diet, and optionally concurrently with folates, including folate precursors, folic acids, and folate derivatives.

It is contemplated that that BH4 will be administered as part of a component of a therapeutic protein formulation. The protein-restricted diet may comprise a normal diet of low-protein containing foodstuff. Alternatively, the protein-restricted diet comprises an intake of protein formula that is phenylalanine-free protein diet, and the subject obtains his essential amount of Phe from remaining components of a very low protein diet. In certain embodiments, the protein-restricted diet is supplemented with non-phenylalanine containing protein supplements. More particularly, the non-phenylalanine containing protein supplements comprise tyrosine or other essential amino acids. In other embodiments, the protein supplements may also comprise folates, including folate precursors, folic acids, and folate derivatives.

The invention contemplates methods of treating an infant having phenylketonuria, comprising administering a stabilized BH4 composition to the patient in an amount effective to produce a decrease in the plasma phenylalanine concentration of the infant wherein the infant is between 0 and 3 years of age and the infant has a plasma phenylalanine concentration of between about 360 μM to about 4800 μM. Prior to the administering of BH4, the infant has a phenylalanine concentration of about 1200 μM and the administering of BH4 decreases the plasma phenylalanine concentration to about 1000 μM. In other embodiments, prior to the administering of BH4 the infant has a phenylalanine concentration of about 800 μM and the administering of BH4 decreases the plasma phenylalanine concentration to about 600 μM. In still further embodiments, prior to the administering of BH4 the infant has a phenylalanine concentration of about 400 μM and the administering of BH4 decreases the plasma phenylalanine concentration to about 300 μM. The therapeutic methods contemplated herein should preferably reduce the plasma phenylalanine concentration of the infant to 360±15 μM.

Also contemplated is a composition comprising a stabilized, crystallize form of BH4 that is stable at room temperature for more than 8 hours and a pharmaceutically acceptable carrier, diluent or excipient. The composition may further comprise a medical protein supplement. In other embodiments, the BH4 composition is part of an infant formula. In still other embodiments, the protein supplement is phenylalanine free. The protein supplement preferably is fortified with L-tyrosine, L-glutamine, L-carnitine at a concentration of 20 mg/100 g supplement, L-taurine at a concentration of 40 mg/100 g supplement and selenium. It may further comprise the recommended daily doses of minerals, e.g., calcium, phosphorus and magnesium. The supplement further may comprise the recommended daily dose of one or more amino acids selected from the group consisting of L-leucine, L-proline, L-lysine acetate, L-valine, L-isoleucine, L-arginine, L-alanine, glycine, L-asparagine monohydrate, L-tryptophan, L-serine, L-threonine, L-histidine, L-methionine, L-glutamic acid, and L-aspartic acid. In addition, the supplement may be fortified with the recommended daily dosage of vitamins A, D and E. The supplement preferably comprises a fat content that provides at least 40% of the energy of the supplement. Such a supplement may be provided in the form of a powder supplement or in the form of a protein bar.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

DESCRIPTION OF THE PREFERRED EMBODIMENTS

Figure 1:
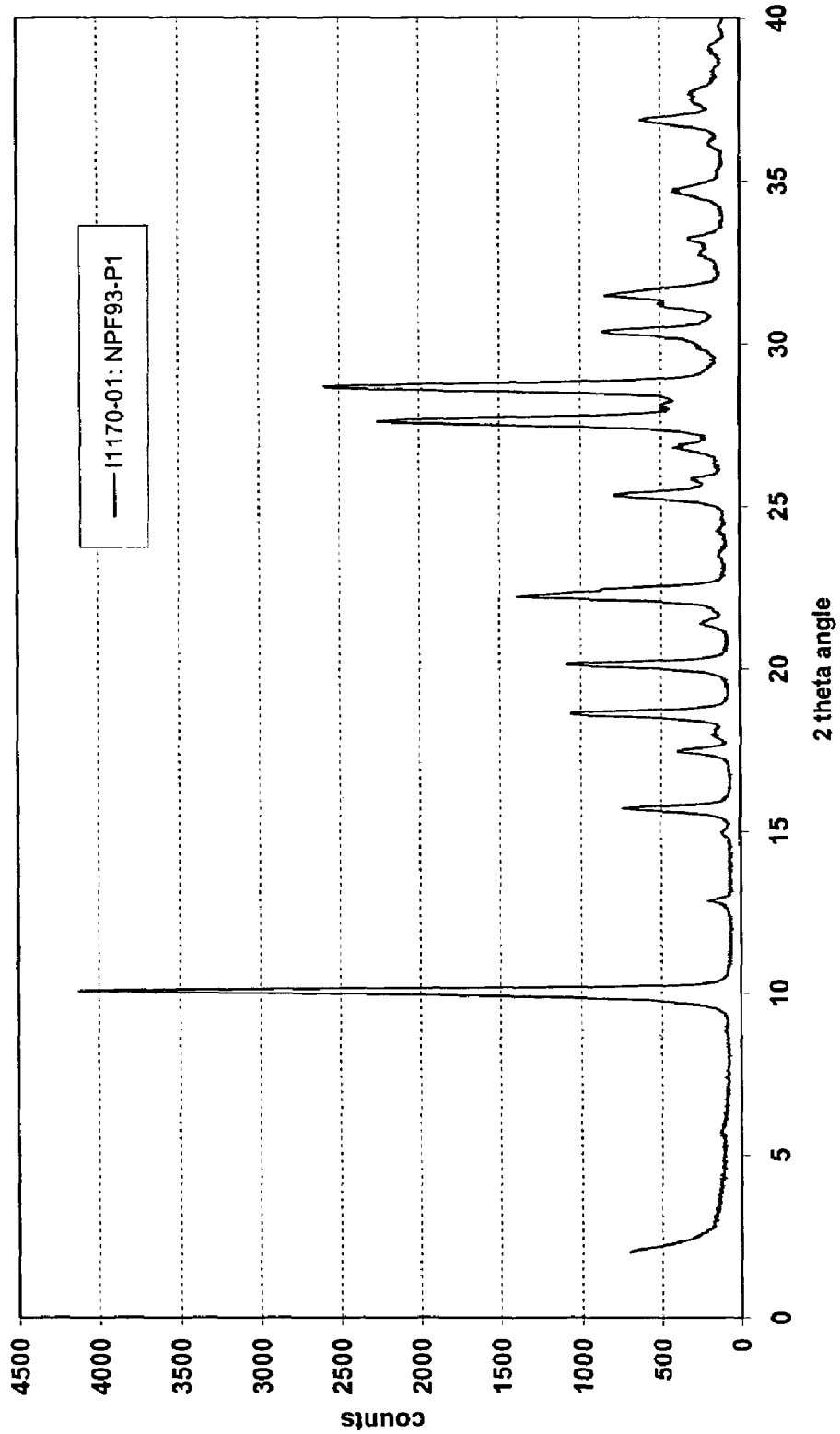
FIG. 1 is a powder X-ray diffraction pattern of (6R)-BH4 Form B.

Dietary intervention is the therapeutic intervention used for all patients with severe classical PKU and in many patients with moderate PKU. However, such dietary protein restriction leads to an inadequate supply of protein, energy, vitamins and minerals to support normal growth and development. Thus, dietary protein restriction is at best an ineffective way of controlling the PKU in many classes of patients, especially in pregnant women and in young children, both categories of subjects that require elevated amounts of protein as compared to normal adult individuals. Use of dietary restriction also is hampered by poor patient compliance with a protein-restricted diet. In October 2000, the National Institutes of Health issued a consensus statement on PKU screening and management in which "research on nondietary alternatives to treatment of PKU [was] strongly encouraged." Thus, there is an art-recognized need for a therapeutic medicament to replace and/or supplement and alleviate the dietary restrictions under which a PKU patient is placed.

The present application for the first time describes a pharmaceutical intervention of PKU based on the administration of a stabilized form of BH4. The methods and compositions for producing such a stabilized BH4 compositions are described in further detail in Example 2. The stabilized BH4 compositions of the present invention comprise BH4 crystals that are stable at room temperature for longer than 8 hours. The methods and compositions of the present invention contemplate pharmaceutical compositions of the stabilized BH4 alone that may be delivered through any conventional route of administration, including but not limited to oral, intramuscular injection, subcutaneous injection, intravenous injection and the like. The compositions of the present invention may further comprise BH4 compositions in combination with an antioxidant that aids in prolonging the stability of the BH4 composition. In addition, discussed in greater below, the present invention further comprises foodstuffs that comprise BH4. For example, the invention contemplates conventional protein powder compositions such as PHENEX, LOFENALAC, PHENYL-FREE and the like that have been modified by the addition of BH4.

The present invention further contemplates the therapeutic intervention of various PKU phenotypes by administration of BH4 in combination with a protein-restricted diet. The BH4 to be administered in combination with the diet may, but need not necessarily, be a stabilized BH4 composition described herein. Those of skill in the art are aware of methods of producing a BH4 composition that is unstable at room temperature and in light. While therapies using such a composition are hindered by the instability of the BH4 composition, its use is still contemplated in certain combination therapies where BH4 non-responsive patients suffering from severe classical PKU are treated with a course of BH4 treatment and dietary protein restriction.

Methods and compositions for effecting the treatment of metabolic disorders, including PKU, are described in further detail herein below.

I. Patients to be Treated

The present invention is directed to the treatment of a variety of HPA patient populations with methods that comprise the use of stabilized BH4 compositions, or unstabilized BH4 compositions, either alone or in combination with other therapeutic regimens, for managing HPA and/or PKU. In particular, it is contemplated that any type of BH4, in a stabilized or other form may be used to treat that patient population that has phenylalanine concentrations that are low enough that dietary intervention is not normally used (i.e., patients with mild HPA). Such patients that are amenable to all forms treatment with BH4 compositions to ameliorate the effects of mild HPA, include pregnant women and infants with serum concentrations of less than 200 µM. The various patient populations, and their different therapeutic needs, are discussed in further detail in the present section.

Certain embodiments of the present invention are directed to treating classic severe PKU by administering to the subject a protein-restricted diet in combination with a composition comprising BH4 or a precursor or derivative thereof, wherein the combined administration of the protein-restricted diet and BH4 is effective to lower the phenylalanine concentration in the plasma of said subject as compared to said concentration in the absence of said combined administration. In addition, the invention also contemplates treating a pregnant female that has HPA by administering to the female a protein-restricted diet in combination with BH4 or a precursor or derivative thereof, such that the combined administration of the protein-restricted diet and BH4 is effective to lower the phenylalanine concentration in the plasma of the pregnant woman as compared to such a concentration in the absence of said combined administration. In specific embodiments, therapy is contemplated for patient who manifest Phe levels greater than 420 µM Other embodiments of the invention entail administering a stabilized BH4 composition to any individual that has HPA, characterized by a plasma Phe concentration greater than 180 µM prior to the administration of the BH4, in an amount effective to produce a decrease in such a plasma Phe concentration of the patient. The methods of the invention also may be used in the treatment of PKU patients that that have been diagnosed as unresponsive to a BH4 loading test. The methods of the invention will be useful in treating an infant having PKU characterized by an elevated Phe concentrations of between greater than 300 µM/L with the stabilized BH4 compositions described herein. By "infant" the present application refers to a patient that is between the ages of 0 to about 36 months.

The data described herein demonstrates that subjects who are considered "unresponsive" to the single dose BH4 loading test may in fact respond to multiple doses of BH4 with a significant reduction in phenylalanine levels. Thus, another aspect of the invention provides a multiple dose loading test that involves administration of more than one dose of BH4. Exemplary multiple dose loading tests include administration of between 5 and 40 mg/kg tetrahydrobiopterin, or more preferably 10 to 20 mg/kg, over a time period of at least 1 day, or at least 2 days, or at least 3, 4, 5, 6, 7, 10 or 14 days, preferably 2-14, 3-14, or 5-10 days, and most preferably 7 days.

The invention provides methods of using any of the tetrahydrobiopterin polymorphs described herein, or stable pharmaceutical preparations comprising any of such polymorphs, for treatment of conditions associated with elevated phenylalanine levels or decreased tyrosine levels, which may be caused, for example, by reduced phenylalanine hydroxylase, tyrosine hydroxylase, or tryptophan hydroxylase activity. Conditions associated with elevated phenylalanine levels specifically include phenylketonuria, both mild and classic, and hyperphenylalaninemia as described elsewhere herein, and exemplary patient populations include the patient subgroups described herein as well as any other patient exhibiting phenylalanine levels above normal.

The invention further provides methods of using any of the polymorphs described herein, or stable pharmaceutical preparations comprising any of such polymorphs, for treatment of subjects suffering from conditions that would benefit from enhancement of nitric oxide synthase activity and patients suffering from vascular diseases, ischemic or inflammatory diseases, or insulin resistance. The treatment may, for example alleviate a deficiency in nitric oxide synthase activity or may, for example provide an increase in nitric oxide synthase activity over normal levels. It has been suggested that a patient suffering from a deficiency in nitric oxide synthase activity would benefit from treatment with folates, including folate precursors, folic acids, or folate derivatives. Thus, it is also contemplated, that compositions and methods disclosed herein include the concurrent treatment with folates, including folate precursors, folic acids, or folate derivatives. Exemplary folates are disclosed in U.S. Pat. Nos. 6,011,040 and 6,544,994, both of which are incorporated herein by reference, and include folic acid (pteroylmonoglutamate), dihydrofolic acid, tetrahydrofolic acid, 5-methyltetrahydrofolic acid, 5,10-methylenetetrahydrofolic acid, 5,10-methenyltetrahydrofolic acid, 5,10-formiminotetrahydrofolic acid, 5-formyltetrahydrofolic acid (leucovorin), 10-formyltetrahydrofolic acid, 10-methyltetrahydrofolic acid, one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or pharmaceutically compatible salts thereof, or a combination of two or more thereof. Exemplary tetrahydrofolates include 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid, and salts thereof as is treatment with a pharmaceutical composition or foodstuff that comprises both a tetrahydrobiopterin polymorph and a folate.

Nitric oxide is constitutively produced by vascular endothelial cells where it plays a key physiological role in the regulation of blood pressure and vascular tone. It has been suggested that a deficiency in nitric oxide bioactivity is involved in the pathogenesis of vascular dysfunctions, including coronary artery disease, atherosclerosis of any arteries, including coronary, carotid, cerebral, or peripheral vascular arteries, ischemia-reperfusion injury, hypertension, diabetes, diabetic vasculopathy, cardiovascular disease, peripheral vascular disease, or neurodegenerative conditions stemming from ischemia and/or inflammation, such as stroke, and that such pathogenesis includes damaged endothelium, insufficient oxygen flow to organs and tissues, elevated systemic vascular resistance (high blood pressure), vascular smooth muscle proliferation, progression of vascular stenosis (narrowing) and inflammation. Thus, treatment of any of these conditions is contemplated according to methods of the invention.

It has also been suggested that the enhancement of nitric oxide synthase activity also results in reduction of elevated superoxide levels, increased insulin sensitivity, and reduction in vascular dysfunction associated with insulin resistance, as described in U.S. Pat. No. 6,410,535, incorporated herein by reference. Thus, treatment of diabetes (type I or type II), hyperinsulinemia, or insulin resistance is contemplated according to the invention. Diseases having vascular dysfunction associated with insulin resistance include those caused by insulin resistance or aggravated by insulin resistance, or those for which cure is retarded by insulin resistance, such as hypertension, hyperlipidemia, arteriosclerosis, coronary vasoconstrictive angina, effort angina, cerebrovascular constrictive lesion, cerebrovascular insufficiency, cerebral vasospasm, peripheral circulation disorder, coronary arteriorestenosis following percutaneous transluminal coronary angioplasty (PTCA) or coronary artery bypass grafting (CABG), obesity, insulin-independent diabetes, hyperinsulinemia, lipid metabolism abnormality, coronary arteriosclerotic heart diseases or the like so far as they are associated with insulin resistance. It is contemplated that when administered to patients with these diseases, BH4 can prevent or treat these diseases by activating the functions of NOS, increasing NO production and suppressing the production of active oxygen species to improve disorders of vascular endothelial cells.

A. Characteristics of Severe Classical PKU and Methods of Treatment thereof According to the Present Invention.

As indicated herein above in the background section, severe PKU manifests in a plasma Phe concentration greater than 1200 µM/L and may be found to be as high as 4800 µM/L. Patients that have this disorder must be treated with a Phe-free diet in order to bring their plasma Phe concentrations down to a level that is clinically acceptable (typically, less than 600 µM/L, and preferably less than 300 µM/L). These patients are only able to tolerate a maximum of between 250-350 mg dietary Phe per day (Spaapen et al., *Mol. Genet and Metab.* 78:93-99, 2003). As such, these patients are started on a Phe-restricted formula diet between 7-10 days after birth and are burdened with this dietary restriction for the remainder their lifespan. Any alleviation of the strict dietary restrictions that these individuals are encumbered with would be beneficial.

The tests used for the diagnosis of individuals with classical Phe are described in further detail below in Section III. These tests have revealed that patients with classical severe PKU are non-responsive to BH4 and require a low phenylalanine diet (Lucke et al., *Pediatr. Neurol.* 28:228-230, 2003). In the present invention however, it is contemplated that this class of PKU patients should be treated with BH4 in order that the need for a strict phenylalanine-free diet may be alleviated.

Thus, it is contemplated that the methods of the invention will entail determining that the patient is suffering from classical PKU by monitoring the plasma Phe concentration of the individual. The patient is then treated by administering a combined regimen of a low protein diet and BH4 such that there is produced at least a 25% decrease in the plasma Phe concentrations of the patient. Preferably, the method will produce a 30% decrease in the plasma Phe concentration. Even more preferably, the method will produce a 40%, 50%, 60%, 70%, 80%, 90% or greater decrease in the plasma Phe concentration of the individual (for example, where a patient with severe classical PKU has a Phe concentration of 4800 µM/L, a 90% decrease in the Phe concentration will produce a plasma Phe concentration of 480 µM/L, a concentration that is sufficiently low to require little dietary restriction). Of course, it should be understood that the treatment methods of the present invention (whether for treating severe classical PKU or any other HPA described herein), should attempt to lower the plasma Phe concentrations of the patient to levels as close to 360 µM/L±15 µM/L as possible.

In preferred embodiments the plasma Phe concentrations of the classical PKU patient being treated is reduced from any amount of unrestricted plasma Phe concentration that is greater than 1000 µM/L to any plasma Phe level that is less than 600 µM/L. Of course, even if the combined treatment with the BH4 and the protein-restricted diet produces a lesser decrease in plasma Phe concentration, e.g., to a level of between 800 µM/L to about 1200 µM/L, this will be viewed as a clinically useful outcome of the therapy because patients that have a plasma Phe concentration in this range can manage the disease by simply restricting the amount of protein in the diet as opposed to eating a Phe-restricted formula, thereby resulting in a marked improvement in the quality of life of the individual, as well as leading to greater patient compliance with the dietary restriction.

Any increase in the amount of dietary Phe levels that can be tolerated by the patient as a result of the treatment will be considered to be a therapeutically effective outcome. For example, it is contemplated that as a result of administering the BH4-based therapy, the patient will be able to increase his/her intake of dietary Phe from 250-350 mg/day to 350-400 mg/day (i.e., the Phe tolerance phenotype of the patient is altered from that of a classic PKU patient to a moderate PKU patient). Of course, it would be preferable that the therapeutic intervention taught herein would allow the patient to increase his/her intake of dietary Phe from 250-350 mg/day to 400-600 mg/day (i.e., the Phe tolerance phenotype of the patient is altered from that of a classic PKU patient to a mild PKU patient), or even more preferably, to allow the patient to have an intake of greater than 600 mg Phe/day (i.e., normal dietary intake).

B. Characteristics of BH4-Non Responsive PKU Patients and Methods of Treatment thereof According to the Present Invention.

A second group of patients that can be treated with the methods of the present invention are those individuals that have a been determined to have an elevated plasma Phe concentrations i.e., any concentration that is greater than 200 µM/L, but have been diagnosed to be non-responsive to BH4 therapy (as determined by the BH4 loading test described below). Such patients may include those individuals that have mild PKU (i.e., plasma Phe concentrations of up to 600 µM/L), individuals that have moderate PKU (i.e., plasma Phe concentrations of between 600 µM/L to about 1200 µM/L), as well as patients that have classic severe PKU (i.e., plasma Phe concentrations that are greater than 1200 µM/L).

The patients that are non-responsive to BH4 therapy are given BH4 in combination with a reduced amount of protein in their diet in order to decrease the plasma Phe concentrations of the patient. The methods of the present invention are such that the administration of the BH4 therapy produces a greater decrease in the plasma Phe concentrations of the patient as compared to the decrease that is produced with the same dietary protocol administered in the absence of the BH4 therapy.

In preferred embodiments, the patients are administered a composition that comprises a stabilized, crystallized form of BH4 characterized in Example 2 described herein below. This BH4 composition differs from those previously available in the art in that it is more stable at room temperature than the preparations previously known to those of skill in the art, e.g., those available in the BH4 loading kits (Schircks Laboratories, Jona, Switzerland.) Thus, the BH4 formulation may be stored at either room temperature or refrigerated and retain greater potency than the previously available BH4 compositions. As such, it is contemplated that this form of BH4 will have a greater therapeutic efficacy than a similar concentration the previously available BH4 compositions. This greater efficacy may be used to produce a therapeutically effective outcome even in patients that were previously identified as being non-responsive to BH4.

As with the subset of patients described in Section IA above, the BH4 non-responsive patients described in the present section may be treated by the stabilized BH4 compositions either alone or in combination with dietary restrictions. The dietary restrictions may be as a diet that restricts the Phe intake by providing a synthetic medical protein formula that has a diminished amount of Phe or alternatively, the dietary restriction may be one which simply requires that the patient limit his/her overall protein intake but nevertheless allows the patient to eat normal foodstuffs in limited quantities.

The preferred therapeutic outcomes discussed for classical PKU patients in Section IA above are incorporated into the present section by reference. Preferred therapeutic outcomes for patients with moderate PKU (i.e., patients that has an unrestricted plasma Phe concentration of 600 µM/L to 1200 µM/L) include at least a 25% decrease in the plasma Phe concentrations of the patient. Preferably, the method will produce a 30% decrease in the plasma Phe concentration. Even more preferably, the method will produce a 40%, 50%, 60%, 70%, 80%, 90% or greater decrease in the plasma Phe concentration of the individual (for example, where a patient with moderate classical PKU has a Phe concentration of 1000 µM/L, a 90% decrease in the Phe concentration will produce a plasma Phe concentration of 100 µM/L, a concentration that is sufficiently low to require little dietary restriction).

In preferred embodiments, the plasma Phe concentrations of the moderate PKU patient being treated is reduced from any amount of unrestricted plasma Phe concentration that is between 600 µM/L to 1200 µM/L to any plasma Phe level that is less than 300 µM/L. A particularly preferred treatment with the BH4 (either alone or in combination with a dietary restriction) produces a decrease in plasma Phe concentration, e.g., to a level of between 200 µM/L to about 400 µM/L, which will be viewed as a clinically useful outcome of the therapy because patients that have a plasma Phe concentration in this range can manage the disease by simply restricting the amount of protein in the diet as opposed to eating a Phe-restricted formula. Indeed, in many studies, it is taught that such patients may even eat a normal diet.

Any increase in the amount of dietary Phe levels that can be tolerated by the patient as a result of the treatment will be considered to be a therapeutically effective outcome. For example, it is contemplated that as a result of administering the BH4-based therapy (either alone or in combination with other therapeutic intervention), the patient will be able to increase his/her intake of dietary Phe from 350-400 mg/day to 400-600 mg/day (i.e., the Phe tolerance phenotype of the patient is altered from that of a moderate PKU patient to a mild PKU patient). Of course, it would be preferable that the therapeutic intervention taught herein would allow the patient to increase his/her intake of dietary Phe from 350-400 mg/day to 400 to allow the patient to have an intake of greater than 600 mg Phe/day (i.e., normal dietary intake).

Even if the patient being treated is one who manifests only mild PKU, i.e., has a dietary allowance of 400-600 mg Phe intake/day) will benefit from the BH4-based therapies of the present invention because it is desirable to produce a normalized plasma Phe concentration that is as close to 360 µM/L±15 µM/L as possible. For such patients, a preferred therapeutic outcomes will include at least a 25% decrease in the plasma Phe concentrations of the patient. Preferably, the method will produce a 30% decrease in the plasma Phe concentration. Even more preferably, the method will produce a 40%, 50%, 60%, or greater decrease in the plasma Phe concentration of the individual (for example, where a patient with mild PKU has a Phe concentration of 600 µM/L, a 60% decrease in the Phe concentration will produce a plasma Phe concentration of 360 µM/L, i.e., an acceptable, normal concentration of plasma Phe).

In preferred embodiments, the plasma Phe concentrations of the mild PKU patient being treated is reduced from any amount of non-restricted plasma Phe concentration that is between 400 µM/L to 600 µM/L to any plasma Phe level that is less than 100 µM/L. Of course, even if the treatment with the BH4 (either alone or in combination with a dietary restriction) produces a lesser decrease in plasma Phe concentration, e.g., to a level of between 200 µM/L to about 400 µM/L, this will be viewed as a clinically useful outcome of the therapy.

Any increase the amount of dietary Phe levels that can be tolerated by the patient as a result of the treatment will be considered to be a therapeutically effective outcome. For example, it is contemplated that as a result of administering the BH4-based therapy (either alone or in combination with other therapeutic intervention), the patient will be able to increase his/her intake of dietary Phe from 400-600 mg/day (i.e., the Phe tolerance phenotype of the patient is altered from that of a mild PKU patient to a mild HPA patient) to allow the patient to have an intake of greater than 600 mg Phe/day (i.e., normal dietary intake).

Furthermore, even if the patient is one who only manifests the symptoms of non PKU HPA, i.e., has an elevated plasma Phe concentration of up to 600 µM/L, but is otherwise allowed to eat a normal protein diet will benefit from the BH4 therapies of the invention because it has been shown that elevated Phe concentrations have significant effects on the IQ of such individuals. Moreover, as discussed below, BH4-based therapeutic intervention of subjects with special needs, e.g., pregnant women and infants, is particularly important even if that patient's plasma Phe levels are within the perceived "safe" level of less than 200 µM/L.

C. Maternal PKU and Methods of Treatment thereof According to the Present Invention.

Metabolic control of plasma Phe levels in PKU women planning conception and those who are pregnant is important because of the serious consequences to the fetus exposed to even moderately elevated Phe levels in utero, regardless of the PAH status of the fetus. Therapeutic control of plasma Phe concentration is especially important in the first trimester of pregnancy, as failure to achieve adequate control will result in disorders including microcephaly, mental deficiency and congenital heart disease.

For example, the NIH Consensus Statement (vol 17 #3, October 2000) on Phenylketonuria reported that exposure of a fetus to maternal Phe levels of 3-10 mg/dL produced a 24% incidence of microcephaly, whilst those exposed to greater than 20 mg/dL (i.e., greater than 1200 µM/L) had a 73% incidence of microcephaly. Likewise congenital heart disease was found in over 10% of children exposed to maternal Phe levels that were greater than 20 mg/dL. Importantly, it has been noted that levels of Phe greater than 6 mg/dL significantly decrease the IQ of the child. Thus, it is imperative to ensure that the plasma Phe concentration of women with all forms of phenylketonuria, even those manifesting the mildest HPA, must be tightly controlled in order to avoid the risk of maternal PKU syndrome. However, the acceptable target levels for the plasma Phe concentrations of PKU women that have been used in U.S. clinics have ranged between 10 mg/dL and 15 mg/dL, which are much higher than the 2-6 mg/dL levels recommended for pregnant women or the 1-4 mg/dL that are used in British and German clinics to diminish the risks of developing maternal PKU syndrome.

Another important consideration for pregnant women is their overall protein intake. During pregnancy, it is important that women eat sufficient protein because it has been suggested that a low protein diet during pregnancy will result in retarded renal development and subsequent reduction in the number of nephrons and potentially leads to hypertension in adulthood. (D'Agostino, *N. Engl. J. Med.* 348(17)1723-1724, 2003). The following table provides exemplary guidelines for the recommended total dietary protein intake for various individuals.

TABLE

United States Guidelines for dietary protein requirements

| | Age | Recommended Total Protein Intake (g) |
|---|---|---|
| Infant | 6 months or less | 13 |
| | 6 months-1 year | 14 |
| | 1-3 years | 16 |
| Children | 4-6 years | 24 |
| | 7-10 years | 28 |
| Males | 11-14 years | 45 |
| | 15-18 years | 59 |
| | 19-24 | 58 |
| | 25-50 | 63 |
| | 51+ | 63 |
| Females | 11-14 years | 46 |
| | 15-18 years | 44 |
| | 19-24 | 46 |
| | 25-50 | 50 |
| | 51+ | 50 |
| Pregnant | | 60 |
| Lactating | | 65 |

The actual amount of protein ingested depends on the Phe content of the protein. The amino acid profiles of plant proteins is different from animal proteins. For example, with a focus on starches and vegetables, a general rule of 45-50 mg/Phe per gram of protein may suffice. However, an accepted standard for evaluating the constituents amino acids of a protein is an egg white, which contains 3.5 grams of protein of which 204 mg is Phe.

As can be seen from the above exemplary guidelines, in the United States, the recommended protein intake for women of child-bearing age (e.g., less than 51) is from about 44 to 50 g/day, whereas pregnant women require are recommended an intake of about 60 g/day. In Canada and the United Kingdom, the recommended protein intake for pregnant women is in the order of about 70 g/day and 52 g/day. Thus, the need to ensure that the plasma Phe concentration levels of pregnant women are tightly controlled is further complicated by the fact that this group of PKU patient requires more protein than non-pregnant PKU females of comparable age.

In view of the above, it is contemplated that BH4-based therapies of the present invention will be particularly useful in pregnant women. It is contemplated that a woman suffering from any form of HPA who is pregnant or is contemplating pregnancy will be placed on a course of BH4 therapy to ensure that her plasma Phe concentration levels are maintained as close to 180 µM/L to about 360 µM/L as possible. Such a course of therapy will preferably allow that woman to increase her level of normal protein intake.

The discussion of levels of plasma Phe concentrations and the degrees to which such Phe concentrations should be decreased discussed herein above in Sections IA and IB are incorporated into the present section for pregnant women.

D. Managing PKU in Infants and Methods of Treatment thereof According to the Present Invention.

As discussed herein throughout, it has been determined that an elevation in the plasma Phe concentration in infants (ages zero to 3 years old) results in significant drop in IQ of the child. However, as has been discussed elsewhere in the specification, patients that have an elevated plasma Phe concentration of anywhere up to 400 µM/L do not normally receive any dietary intervention. Thus, infants at the age of zero to 3 years in age suffer from significant deleterious effects from the present therapies. The instant application contemplates treating any infant having an unrestricted plasma Phe concentration that is greater than 360 µM/L±15 µM/L with a therapeutic composition that comprises BH4 in order to produce a beneficial decrease the plasma Phe concentration of that subject.

In preferred embodiments, the infant is aged between zero and 3 years of age and has an unrestricted plasma Phe concentration of about 1200 µM/L prior to the administration of BH4 and said administration decreases the plasma Phe concentration. Preferably, the plasma Phe concentration is decreased to from greater than 1800 to about 1500 µM/L, about 1200 µM/L, about 1100 µM/L, about 1000 µM/L, about 900 µM/L, about 800 µM/L, about 700 µM/L, about 600 µM/L, about 550 µM/L, about 500 µM/L, about 450 µM/L, 400 µM/L, about 350 µM/L, about 300 µM/L, about 275 µM/L, about 250 µM/L upon administration. In other embodiments, the infant is aged between zero and 3 years of age and has an unrestricted plasma Phe concentration of greater than 1200 µM/L and preferably, this plasma Phe concentration is decreased to about 800 µM/L, or more preferably to about 500 µM/L or even more preferably to about 360 µM/L upon administration of BH4, either alone or in combination with diet. Those of skill in the art would understand that the invention contemplates treating infants with unrestricted plasma Phe concentrations of greater than 360 µM/L with BH4 to produce decreases in such plasma Phe concentrations. The discussion of therapeutic reductions of plasma Phe concentrations in Sections IA and IB above are incorporated herein by reference. Further, any decrease over 10% of the initial unrestricted plasma Phe concentration will be considered a therapeutic outcome for the therapeutic regimens for the infants. It should be understood that the BH4 therapies may be combined with dietary restrictions to effect the therapeutic decrease in plasma Phe concentrations in such infants.

II. Compositions for Use in the Treatment

The present invention contemplates therapeutic intervention of PKU/HPA. Such intervention is based initially on the use of BH4. The BH4 may be used alone or in combination with dietary restrictions. Further the BH4 and/or dietary restrictions may further be combined with other therapeutic compositions that are designed, for example to combat other manifestations of PKU, such as for example, large neutral amino acids to prevent Phe accumulation in the brain (see Koch et al., Mol. Genet. Metabol. 79:110-113, 2003) or tyrosine supplementation. The present section provides a discussion of the compositions that may be used in the treatments contemplated herein.

A. BH4 Compositions

BH4 is a cofactor in Phe hydroxylation and prior to the present invention, it was shown that less than 2% of patients having an elevated Phe at birth have defects in BH4 synthesis. With those individuals that were identified as being BH4 responsive, it was suggested that the patients would be non-responsive to dietary intervention and hence, those individuals were fed a normal diet but given BH4 therapy alone. Thus, prior to the present invention, there was much skepticism in the art as to the therapeutic benefits of BH4 administration to PKU/HPA patients. However, as discussed herein throughout, BH4 may be administered for a therapeutic intervention of patients that have been diagnosed as non-BH4 responsive. Moreover, the present inventors show that BH4 therapy can be combined with dietary restrictions to produce a therapeutic outcome in both individuals that are responsive to a BH4 loading test as well as individuals that are non-responsive to BH4 loading.

U.S. Pat. Nos. 5,698,408; 2,601,215; 3,505,329; 4,540,783; 4,550,109; 4,587,340; 4,595,752; 4,649,197; 4,665,182; 4,701,455; 4,713,454; 4,937,342; 5,037,981; 5,198,547; 5,350,851; 5,401,844; 5,698,408 and Canadian application CA 2420374 (each incorporated herein by reference) each describe methods of making dihydrobiopterins, BH4 and derivative thereof that may be used as compositions for the present invention. Any such methods may be used to produce BH4 compositions for use in the therapeutic methods of the present invention.

U.S. Pat. Nos. 4,752,573; 4,758,571; 4,774,244; 4,920,122; 5,753,656; 5,922,713; 5,874,433; 5,945,452; 6,274,581; 6,410,535; 6,441,038; 6,544,994; and U.S. Patent Publications US 20020187958; US 20020106645; US 2002/0076782; US 20030032616(each incorporated herein by reference) each describe methods of administering BH4 compositions for non-PKU treatments. Each of those patents is incorporated herein by reference as providing a general teaching of methods of administering BH4 compositions known to those of skill in the art, that may be adapted for the treatment of PKU/HPA as described herein.

In addition to the above general methods of making BH4, the present invention particularly contemplates making and using a BH4 composition which is a stabilized BH4 composition. Preferably the stabilized BH4 composition is in crystalline form. Methods of making the stabilized BH4 compositions for use in the present invention are described in Example 2. Such a crystalline form may prove useful as an additive to conventional protein formulas for the treatment of PKU. The crystalline form also may conveniently be formed into a tablets, powder or other solid for oral administration.

The forms and routes of administration of BH4 are discussed in further detail in the Pharmaceutical Compositions section below.

In preferred embodiments, it is contemplated that the methods of the present invention will provide to a patient in need thereof, a daily dose of between about 10 mg/kg to about 20 mg/kg of BH4. Of course, one skilled in the art may adjust this dose up or down depending on the efficacy being achieved by the administration. The daily dose may be administered in a single dose or alternatively may be administered in multiple doses at conveniently spaced intervals. In exemplary embodiments, the daily dose may be 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg, 24 mg/kg, 26 mg/kg, 28 mg/kg, 30 mg/kg, 32 mg/kg, 34 mg/kg, 36 mg/kg, 38 mg/kg, 40 mg/kg, 42 mg/kg, 44 mg/kg, 46 mg/kg, 48 mg/kg, 50 mg/kg, or more mg/kg.

Regardless of the amount of BH4 administered, it is desirable that the administration decreases the plasma Phe concentration of the patients to the concentrations discussed in Section I for the various types of patients.

B. Dietary Protein

In addition to administering BH4 and related analogs to HPA/PKU patients, it is contemplated that the dietary protein of the patients also may be restricted or modified. Those of skill in the art are aware of various commercially available protein formulas for use in the treatment of PKU. Such formulas include MAXIMAID, PHENEX 1, PHENEX 2 (Ross Laboratories, Liverpool, UK), LOFENALAC, PHENYL-FREE (Mead-Johnson), and the like.

Those of skill in the art may use the referenced protein formulas, which are generally free of Phe concentrations. The protein formulas often are supplemented with amino acids that are deficient in PKU patients. Such amino acids include, for example, L-tyrosine, and L-glutamine. It has been suggested that it may be desirable to supplement the diet of PKU patients with valine, isoleucine and leucine (see U.S. Pat. No. 4,252,822). In certain clinical manifestations, the toxic effects of PKU are caused by Phe blocking the brain uptake of other amino acids such as tyrosine and tryptophan. It has been found that supplementing the diet of a PKU patient with excess of such large neutral amino acids blocks Phe uptake into the brain and lowers brain Phe levels. Thus, it is contemplated that for the methods of the present invention, the dietary regimen may further be supplemented with compositions that comprise one or more of these amino acids (Koch et al., Mol. Genet. Metabol. 79:110-113, 2003).

Further, as it is known that L-carnitine and taurine which are normally found in human milk and other foodstuffs of animal origin also should be supplied in addition to the protein restriction. In certain embodiments, the L-carnitine may be supplied as 20 mg/100 g of protein supplement, and the taurine may be supplied as 40 mg/100 g protein supplement in order to help supply amounts of these factors normally found in human milk and foods of animal origin.

In addition, those of skill in the art are by reference to the 2000 National Academy of Sciences-National Research Council Dietary Reference Intakes for a further listing of other components, such as essential vitamins and minerals that should be supplied to the patient to ensure that other supplements are being provided despite the dietary protein restriction.

Referring to the Table presented in Section IC above for total protein amounts and the figures presented in Section I in general for the desirable plasma Phe concentrations, one of skill in the art will be able to determine the amount of dietary protein restriction that is required and thus adjust the diet of the patient accordingly. Taking for example, a male of about 11-14 years of age, that individual should preferably receive 45 g protein/day. In the event that the individual is one that has severe classic PKU, his unrestricted plasma Phe concentration will likely be greater than 1200 µM/L, and most, if not all of the dietary protein source for that individual is likely to be from a powdered protein supplement, which preferably lowers his plasma Phe concentrations to less than 600 µM/L. By administering BH4 to that subject, a therapeutic outcome would be one which produces greater decrease in the plasma Phe concentrations of patient or alternatively, the therapeutic outcome is one in which the individual's plasma Phe concentrations is lowered to a similar degree, but that individual is able to tolerate protein from a normal diet rather than from a dietary formula.

Similarly, a male of about 11-14 years of age, is one who has moderate PKU, it may be possible using the methods of the present invention to give him the allotted 45 g protein/day through a normal protein intake rather than a restricted formula. Determining whether the methods of the invention are effective will entail determining the plasma Phe concentrations of the patient on a regular basis to ensure that the plasma Phe concentrations remain below at least 400 µM/L. Tests for determining such concentrations are described below. Preferably, concentrations of less than or about 360 µM/L are achieved.

III. Identifying and Monitoring Patient Populations

As discussed herein throughout, it will be necessary in various embodiments of the present invention to determine whether a given patient is responsive to BH4 therapy, and to determine the phenylalanine concentrations of the patient both initially to identify the class of PKU patient being treated and during an ongoing therapeutic regimen to monitor the efficacy of the regimen. Exemplary such methods are described herein below.

A. BH4 Loading Test

In order to identify a patient as being responsive to BH4, those of skill in the art perform a "BH4 loading" test. Two types of loading tests have been used to achieve the differential diagnosis of HPA. The first is a simple oral BH4 loading test and the second is a combined phenylalanine/BH4 loading test.

The simplest BH4 loading test is one in which exogenous BH4 is administered and the effects of the administration on lowering of plasma Phe concentrations is determined. Intravenous loading of 2 mg/kg BH4 was initially proposed by Danks et al., (*Lancet* 1:1236, 1976), as BH4 of greater purity has become available it has become possible to perform the test using an oral administration of BH4 in amounts of about 2.5 mg/kg body weight. Ultimately, a standardized approach was proposed by Niederwieser et al. in which a 7.5 mg/kg single oral dose of BH4 is administered (*Eur. J. Pediatr.* 138:441, 1982), although some laboratories do still use upwards of 20 mg BH4/kg body weight. This test allows discrimination between patients that have HPA due to a deficit in BH4 or through a deficiency in PAH.

In order for the simple BH4 loading test to produce reliable results, the blood Phe levels of the patient need to be higher than 400 µM/L. Therefore, it is often customary for the patient to be removed from the PKU diet for 2 days prior to performing the loading test. A BH4 test kit is available and distributed by Dr. Schircks Laboratories (Jona, Switzerland). This kit recommends a dosage of 20 mg BH4/kg body weight about 30 minutes after intake of a normal meal.

As indicated above, the Phe concentration of a patient ideally needs to be higher than 400 µM/L in order to obtain an accurate BH4 reading. In the combined Phenylalanine/BH4 loading test, an oral administration of Phe (100 mg/kg body weight) plus BH4 (20 mg/kg body weight) allows selective screening of all BH4 deficiencies. Typically, the Phe is administered in an oral dose and it is followed approximately one hour later with BH4. The plasma Phe levels are monitored before and at convenient time intervals (e.g., 1, 3, 5, 9, 13 and 25 hours) post-Phe administration.

In either the simple BH4 loading test or the combined Phe/BH4 loading test, it has been suggested that a decrease in plasma Phe of more than 30% of the plasma Phe value prior to BH4 challenge within 24 hours post-load is indicative of BH4 responsiveness (Spaapen et al, *Mol. Genet. and Metabol.*, 78:93-99, 2003).

Other methods of performing BH4 loading tests also may be used. Exemplary such tests are described in e.g., Muntau et al., (N. Engl. J. Med. 347(26):2002) and Berneggar and Blau (Mol. Genet. Metabol. 77:304-313, 2002).

In Berneggar and Blau, the BH4 loading test uses 20 mg/kg BH4 and blood sampling for phenylalanine and tyrosine is performed at 0, 4, 8, and 24 hours to differentiate between BH4-responders and non-responders. The test us carried out after at least 3 hours of fasting. Urine samples of neopterin and biopterin are tested before the test. After an oral application of 6R BH4 (20 mg·kg body weight), normal food intake is allowed during the etire testing period. Blood samples are assayed for Phe and Tyr measurements at 0, 4, 8 and 24 hours. Another urine sample is collected between 4-8 hours. Dihydropteridine reductase activity also may be measured anytime during the test. In patients that have plasma phenylalanine levels less than 400 µM/L or patients already on a low-phenylalanine diet, Berneggar and Blau recommend a combined phenylalanine-BH4 test in which 100 mg Phe/kg body weight is administered orally 3 hours before the BH4 administration.

Berneggar and Blau calculated BH4-responsiveness as "phenyalanine hydroxylation" at 4 and 8 hours after loading and was expressed as a percentage of the phenylalanine eliminated. The slope (S) of the graphs of "hydroxylation rates" at 0, 4 abd 8 hours are compared fro different BH4 products and different groups of patient. The slop discriminates between non-responders, slow responders and responders. The slow responders (see FIG. 5 in Berneggar and Blau) need more time to reach the cut-off values of 360 µM/L and that the effectiveness of administered BH4 depends on the initial phenylalanine levels. These authors recommend that for some patients with plasma Phe of less than 800 µM/L and for most patients with a plasma Phe greater than 1200 µM/L, a Phe measurement should be taken at 21 hours. A plot of Phe/S vs. time can be used to estimate the time needed to reach the therapeutic "safe" plasma Phe values of less than 360 µM/L.

Muntau et al. (2002) also provide exemplary BH4 loading tests that can be used to calculate the times and concentrations of BH4 administration. Again these authors employed a combined PHE/BH4 loading test in which patients are give a meal that contains 100 mg Phe/kg body weight. One hour after the meal, the patients are given an oral dose of 20 mg/kg BH4 (Schirks Laboratories). Blood phenylalanine concentrations are determined by electrospray ionization mass spectrometry before Phe loading as well as before, and at 4, 8, and 15 hours after BH4 loading. Newborns may be breast fed, whereas older patients are give a standardized protein intake (10 mg Phe/kg) between 6-8 hours after BH4 loading. Muntau also describe methods for Phe oxidation. After a 4-hour fast and an overnight fast a total of 6 mg/kg 13C labeled Phe dissolved in dextrose solution is administered orally. Breath samples are then collected over a period of 180 minutes and stored in evacuated glass tubes. The samples are then analysed using isotope ration mass spectrometry and the recovery of carbon 13 is calculated (Treacy et al., *Pediat. Res.* 42:430-5, 1997)

Muntau et al. classify patients as BH4 responsive when the blood Phe levels 15 hours post-BH4 challeng have decreased by more than 30% from the value obtained prior to the BH4 administration. An improvement in the rate of Phe oxidation, as determined by measurements of carbon dioxide obtained during the 180 minutes of testing, was considered significant when the supplementation with BH4 increased the value of Phe oxidation by at least 15%.

Those of skill in the art will be able to use any of the above-referenced methods to determine whether an individual will be responsiveness to BH4. However, other equivalent and related methods for determining BH4 responsiveness also may be known to those of skill in the art and may be used instead of the methods described above.

B. Determination of Phe Concentrations

There are numerous methods for determining the presence of Phe in blood (Shaw et al., *Analytical Methods in Phenylketonuria-Clinical Biochemistry, InBickett et al. Eds. Phenylketonuria and Some Other Inborn Errors of Amino Acid Metabolism*, Stuttgart, Georg Thiem Verlag, 47-561971,). Typically, phenylalanine and tyrosine concentrations are determined from the serum of a patient using a fluorometric assay. This assay relies on the formation of fluorescent substance when phenylalanine is heated with ninhydrin in the presence of leucylalanine (McCaman et al., *J. Lab. Clin. Med.* 59:885-890, 1962.)

The most popular method for determining Phe concentrations is the Guthrie test in which discs are punctured from filter paper that has been saturated with a blood sample from the patient. The uniform discs are incubated in a tray of agar that has been seeded with *Bacillus subtilis* and contains a specific inhibitor of *Bacillus subtilis* growth. As the phenylalanine transfers from the uniform discs onto the agar, the Phe reverse the inhibition of bacterial growth thereby yielding an area of bacterial growth that can be correlated to phenylalanine concentration by comparison to similar assays performed using discs containing known amounts of Phe.

Other methods of quantifying Phe concentration include HPLC, mass spectrometry, thin layer chromatography and the like. Such methods can be used to determine the plasma Phe concentration of a patient before the therapy and to monitor the Phe concentration during the therapeutic regimen to determine the efficacy thereof.

It is contemplated that the plasma Phe levels of the patients will be monitored at convenient intervals (e.g., daily, every other day or weekly) throughout the time course of the therapeutic regimen. By monitoring the plasma Phe levels with such regularity, the clinician will be able to assess the efficacy of the treatment and adjust the BH4 and/or dietary protein requirements accordingly.

IV. Combination Therapy

Certain methods of the invention involve the combined use of BH4 and dietary protein restriction to effect a therapeutic outcome in patients with various forms of HPA. To achieve the appropriate therapeutic outcome in the combination therapies contemplated herein, one would generally administer to the subject the BH4 composition and the dietary restriction in a combined amount effective to produce the desired therapeutic outcome (i.e., a lowering of plasma Phe concentration and/or the ability to tolerate greater amounts of Phe/protein intake without producing a concomitant increase in plasma Phe concentrations). This process may involve administering the BH4 composition and the dietary protein therapeutic composition at the same time. This may be achieved by administering a single composition or pharmacological protein formulation that includes all of the dietary protein requirements and also includes the BH4 within said protein formulation. Alternatively, the dietary protein (supplement or normal protein meal) is taken at about the same time as a pharmacological formulation (tablet, injection or drink) of BH4. The BH4 also may be formulated into a protein bar or other foodstuff such as brownies, pancakes, cake, suitable for ingestion.

In other alternatives, the BH4 treatment may precede or follow the dietary protein therapy by intervals ranging from minutes to hours. In embodiments where the protein and the BH4 compositions are administered separately, one would generally ensure that a significant period of time did not expire between the time of each delivery, such that the BH4 will still be able to exert an advantageously effect on the patient. In such instances, it is contemplated that one would administer the BH4 within about 2-6 hours (before or after) of the dietary protein intake, with a delay time of only about 1 hour being most preferred. In certain embodiments, it is contemplated that the BH4 therapy will be a continuous therapy where a daily dose of BH4 is administered to the patient indefinitely. In other situations, e.g., in pregnant women having only the milder forms of PKU and HPA, it may be that the BH4 therapy is only continued for as long as the woman is pregnant and/or breast feeding.

Further, in addition to therapies based solely on the delivery of BH4 and dietary protein regulation, the methods of the present invention also contemplate combination therapy with a third composition that specifically targets one or more of the symptoms of HPA. For example, it is known that the deficit in tyrosine caused by HPA results in a deficiency in neurotransmitters dopamine and serotonin. Thus, in the context of the present invention, it is contemplated that BH4 and dietary protein based methods could be further combined with administration of L-dopa, carbidopa and 5-hydroxytryptophan neurotransmitters to correct the defects that result from decreased amounts of tyrosine in the diet.

In addition, gene therapy with both PAH (Christensen et al., *Mol. Gent. And Metabol.* 76: 313-318, 2002; Christensen et al., Gene Therapy, 7:1971-1978, 2000) and phenylalanine ammonia-lyase (PAL Liu et al., *Arts. Cells. Blood. Subs and Immob. Biotech.* 30(4)243-257, 2002) has been contemplated by those of skill in the art. Such gene therapy techniques could be used in combination with the combined BH4/dietary protein restriction based therapies of the invention. In further combination therapies, it is contemplated that phenylase may be provided as an injectable enzyme to destroy lower Phe concentrations in the patient. As the administration of phenylase would not generate tyrosine (unlike administration of PAH), such treatment will still result in tyrosine being an essential amino acid for such patients. Therefore dietary supplementation with tyrosine may be desirable for patients receiving phenylase in combination with the BH4 therapy.

V. Pharmaceutical Compositions

Pharmaceutical compositions for administration according to the present invention can comprise a first composition comprising BH4 in a pharmaceutically acceptable form optionally combined with a pharmaceutically acceptable carrier. These compositions can be administered by any means that achieve their intended purposes. Amounts and regimens for the administration of a composition according to the present invention can be determined readily by those with ordinary skill in the art for treating PKU. As discussed above, those of skill in the art could initially employ amounts and regimens of BH4 currently being proposed in a medical context, e.g., those compositions that are being proposed for modulating NOS activity, or for use in the treatment of pain or depression as discussed in the patents listed in Section II above. Any of the protocols, formulations, routes of administration and the like described that have been used for administering BH4 for loading tests can readily be modified for use in the present invention.

The compositions and methods described herein are not limited to the use of a particular form of BH4, or form of an analog or derivative of BH4. Indeed, it is contemplated that the compositions and methods within the scope of this invention include all compositions comprising any form BH4, and any form of an analog or derivative thereof in an amount effective to achieve its intended purpose. Nonlimiting examples of analogs for use in the compositions and methods described herein include pteridine, pterin, neopterin, biopterin, 7,8-Dihydrobiopterin, 6-methyltetrahydropterin, and other 6-substituted tetrahydropterin and other 6-substituted tetrahydropterins, sepiapterin, 6,7-Dimethyltetrahydropterin, 6-methyl biopterin and other 6-substituted biopterins, and other analogs that are described in the art. Nonlimiting examples of derivatives for use in the compositions and methods described herein include the derivatives described in U.S. Pat. Nos. 4,758,571; 4,774,244; 6,162,806; 5,902,810; 2,955,110; 2,541,717; 2,603,643; and 4,371,514, the disclosures of which are hereby incorporated herein.

Certain therapeutic methods of the present invention contemplate a combination therapy in which BH4-based compositions are administered in addition to a modified protein diet, the pharmaceutical compositions of the invention also contemplate all compositions comprising at least BH4-based therapeutic agent, analog or homologue thereof in an amount effective to achieve the amelioration of one or more of the symptoms of PKU when administered in combination with the modified protein diet. Of course, the most obvious symptom that may be alleviated is that the combined therapy produces a decrease in the plasma Phe concentration, however, other symptoms such as changes in IQ, executive function, concentration, mood, behavioral stability job performance and the like also may be monitored. Such indicia are monitored using techniques known to those of skill in the art.

Crystalh Polymorphs of (6R) L-Tetrahydrobiopterin Dihydrochloride Salt

It has been found that BH4, and in particular, the dihydrochloride salt of BH4, exhibits crystal polymorphism. The structure of BH4 is shown below:

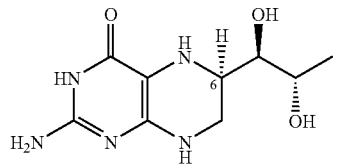

The (6R) form of BH4 is the known biologically active form, however, BH4 is also known to be unstable at ambient temperatures. It has been found that one crystal polymorph of BH4 is more stable, and is stable to decomposition under ambient conditions.

BH4 is difficult to handle and it is therefore produced and offered as its dihydrochloride salt (Schircks Laboratories, Jona, Switzerland) in ampoules sealed under nitrogen to prevent degradation of the substance due to its hygroscopic nature and sensitivity to oxidation. U.S. Pat. No. 4,649,197 discloses that separation of (6R)- and 6(S)-L-erythro-tetrahydrobiopterin dihydrochloride into its diastereomers is difficult due to the poor crystallinity of 6(R,S)-L-erythro-tetrahydrobiopterin dihydrochloride. The European patent number 0 079 574 describes the preparation of tetrahydrobiopterin, wherein a solid tetrahydrobiopterin dihydrochloride is obtained as an intermediate. S. Matsuura et al. describes in Chemistry Letters 1984, pages 735-738 and Heterocycles, Vol. 23, No. 12, 1985 pages 3115-3120 6(R)-tetrahydrobiopterin dihydrochloride as a crystalline solid in form of colorless needles, which are characterized by X-ray analysis disclosed in J. Biochem. 98, 1341-1348 (1985). An optical rotation of 6.81° was found the crystalline product, which is quite similar to the optical rotation of 6.51° reported for a crystalline solid in form of white crystals in example 6 of EP-A2-0 191 335.

Results obtained during development of (6R)-L-erythro-tetrahydrobiopterin dihydrochloride indicated that the compound may exist in different crystalline forms, including polymorphic forms and solvates. The continued interest in this area requires an efficient and reliable method for the preparation of the individual crystal forms of (6R)-L-erythro-tetrahydrobiopterin dihydrochloride and controlled crystallization conditions to provide crystal forms, that are preferably stable and easy to handle and to process in the manufacture and preparation of formulations, and that provide a high storage stability in substance form or as formulated product, or which provide less stable forms suitable as intermediates for controlled crystallization for the manufacture of stable forms.

Polymorph Form B

The crystal polymorph that has been found to be the most stable is referred to herein as "form B," or alternatively as "polymorph B." Results obtained during investigation and development of (6R)-L-erythro-tetrahydrobiopterin dihydrochloride development revealed that there are several known crystalline solids have been prepared, but none have recognized the polymorphism and its effect on the stability of the BH4 crystals.

Polymorph B is a slightly hygroscopic anhydrate with the highest thermodynamic stability above about 20° C. Furthermore, form B can be easily processed and handled due to its thermal stability, possibility for preparation by targeted conditions, its suitable morphology and particle size. Melting point is near 260° C. ($\Delta Hf > 140$ J/g), but no clear melting point can be detected due to decomposition prior and during melting. These outstanding properties renders polymorph form B especially feasible for pharmaceutical application, which are prepared at elevated temperatures. Polymorph B can be obtained as a fine powder with a particle size that may range from 0.2 μm to 500 μm.

Form B exhibits an X-ray powder diffraction pattern, expressed in d-values (Å) at: 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), 2.44 (w). FIG. 1 is a graph of the characteristic X-ray diffraction pattern exhibited by form B of (6R)-L-erythro-tetrahydrobiopterin dihydrochloride.

As used herein, the following the abbreviations in brackets mean: (vs)=very strong intensity; (s)=strong intensity; (m)=medium intensity; (w)=weak intensity; and (vw)=very weak intensity. A characteristic X-ray powder diffraction pattern is exhibited in FIG. 1.

It has been found that other polymorphs of BH4 have a satisfactory chemical and physical stability for a safe handling during manufacture and formulation as well as providing a high storage stability in its pure form or in formulations. In addition, it has been found that form B, and other polymorphs of BH4 can be prepared in very large quantities (e.g., 100 kilo scale) and stored over an extended period of time.

All crystal forms (polymorphs, hydrates and solvates), inclusive crystal form B, can be used for the preparation of the most stable polymorph B. Polymorph B may be obtained by phase equilibration of suspensions of amorphous or other forms than polymorph form B, such as polymorph A, in suitable polar and non aqueous solvents. Thus, the pharmaceutical preparations described herein refers to a preparation of polymorph form B of (6R)-L-erythro-tetrahydrobiopterin dihydrochloride.

Other forms of BH4 can be converted for form B by dispersing the other form of BH4 in a solvent at room temperature, stirring the suspension at ambient temperatures for a time sufficient to produce polymorph form B, thereafter isolating crystalline form B and removing the solvent from the isolated form B. Ambient temperatures, as used herein, mean temperatures in a range from 0° C. to 60° C., preferably 15° C. to 40° C. The applied temperature may be changed during treatment and stirring by decreasing the temperature stepwise or continuously. Suitable solvents for the conversion of other forms to form B include but are not limited to, methanol, ethanol, isopropanol, other C3- and C4-alcohols, acetic acid, acetonitrile, tetrahydrofurane, methy-t-butyl ether, 1,4-dioxane, ethyl acetate, isopropyl acetate, other C3-C6-acetates, methyl ethyl ketone and other methyl-C3-C5 alkyl-ketones. The time to complete phase equilibration may be up to 30 hours and preferably up to 20 hours or less than 20 hours.

Polymorph B may also be obtained by crystallisation from solvent mixtures containing up to about 5% water, especially from mixtures of ethanol, acetic acid and water. It has been found that polymorph form B of (6R)-L-erythro-tetrahydrobiopterin dihydrochloride can be prepared by dissolution, optionally at elevated temperatures, preferably of a solid lower energy form than form B or of form B of (6R)-L-erythro-tetrahydrobiopterin dihydrochloride in a solvent mixture comprising ethanol, acetic acid and water, addition of seeds to the solution, cooling the obtained suspension and isolation of the formed crystals. Dissolution may be carried out at room temperature or up to 70° C., preferably up to 50° C. There may be used the final solvent mixture for dissolution or the starting material may be first dissolved in water and the other solvents may than be added both or one after the other solvent. The composition of the solvent mixture may comprise a volume ratio of water: acetic acid: tetrahydrofuran of 1:3:2 to; 1:9:4 and preferably 1:5:4. The solution is preferably stirred. Cooling may mean temperatures down to −40° C. to 0° C., preferably down to 10° C. to 30° C. Suitable seeds are polymorph form B from another batch or crystals having a similar or identical morphology. After isolation, the crystalline form B can be washed with a non-solvent such as acetone or tetrahydrofurane and dried in usual manner.

Polymorph B may also be obtained by crystallisation from aqueous solutions through the addition of non-solvents such as methanol, ethanol and acetic acid. The crystallisation and isolation procedure can be advantageously carried out at room temperature without cooling the solution. This process is therefore very suitable to be carried out at an industrial scale.

In one embodiment of the compositions and methods described herein, a composition including polymorph form B of (6R)-L-erythro-tetrahydrobiopterin dihydrochloride is prepared by dissolution of a solid form other than form B or of form B of (6R)-L-erythro-tetrahydrobiopterin dihydrochloride in water at ambient temperatures, adding a non-solvent in an amount sufficient to form a suspension, optionally stirring the suspension for a certain time, and thereafter isolation of the formed crystals. The composition is further modified into a pharmaceutical composition as described below.

The concentration of (6R)-L-erythro-tetrahydrobiopterin dihydrochloride in the aqueous solution may be from 10 to 80 percent by weight, more preferably from 20 to 60 percent by weight, by reference to the solution. Preferred non-solvents (i.e., solvents useful in preparing suspensions of BH4) are methanol, ethanol and acetic acid. The non-solvent may be added to the aqueous solution. More preferably, the aqueous solution is added to the non-solvent. The stirring time after formation of the suspension may be up to 30 hours and preferably up to 20 hours or less than 20 hours. Isolation by filtration and drying is carried out in known manner as described above.

Polymorph form B is a very stable crystalline form, that can be easily filtered off, dried and ground to particle sizes desired for pharmaceutical formulations. These outstanding properties renders polymorph form B especially feasible for pharmaceutical application.

Polymorph Form A

It has been found that another crystal polymorph of (6R)-L-erythro-tetrahydrobiopterin dihydrochloride is a stable prefered form of BH4 for use in a pharmaceutical preparation described herein, which shall be referred to herein as "form A," or "polymorph A." Polymorph A is slightly hygroscopic and adsorbs water to a content of about 3 percent by weight, which is continuously released between 50° C. and 200° C., when heated at a rate of 10° C./minute. The polymorph A is a hygroscopic anhydrate which is a meta-stable form with respect to form B; however, it is stable over several months at ambient conditions if kept in a tightly sealed container. Form A is especially suitable as intermediate and starting material to produce stable polymorph forms. Polymorph form A can be prepared as a solid powder with desired medium particle size range which is typically ranging from 1 μm to about 500 μm.

Figure 2:
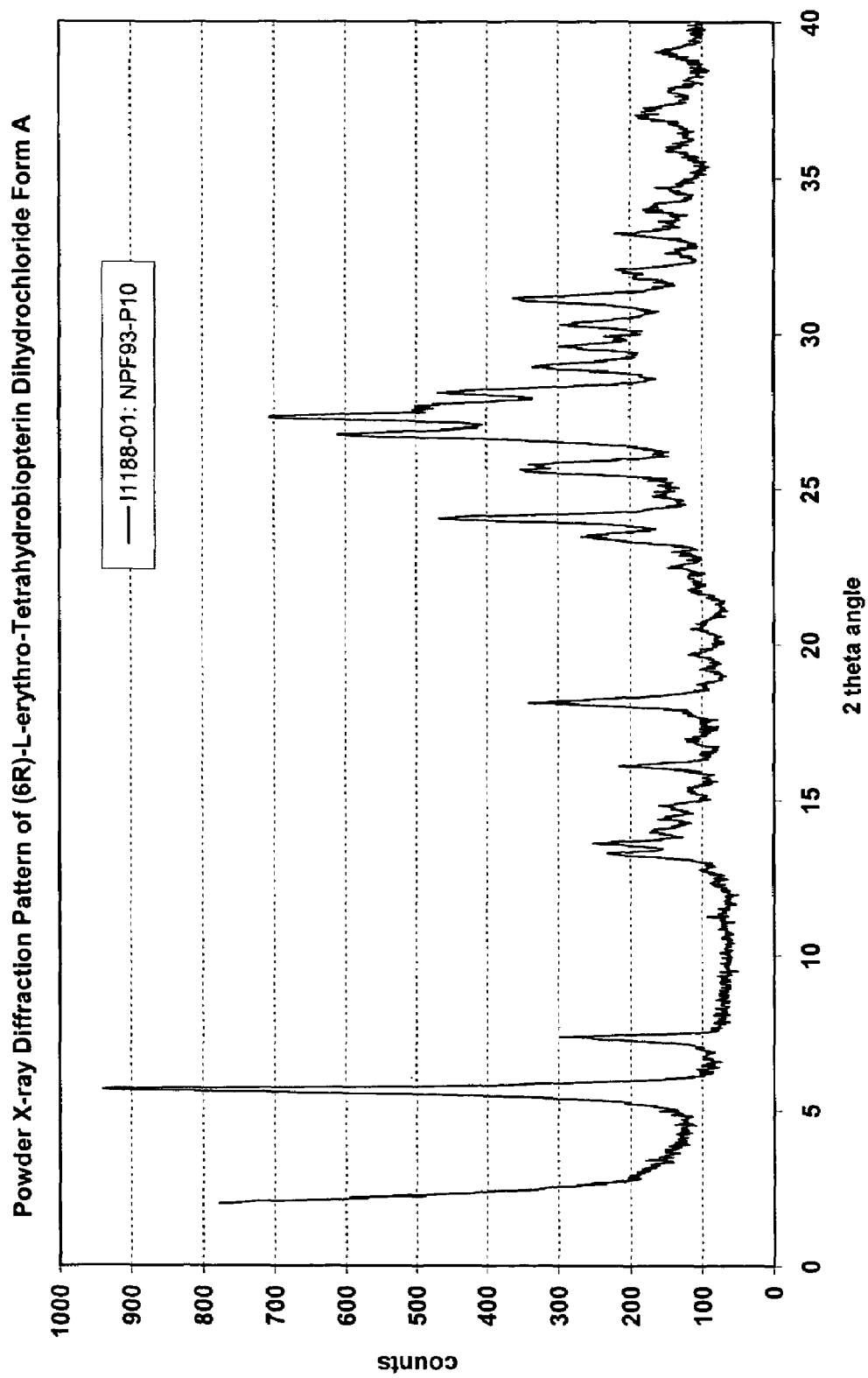
FIG. 2 is a powder X-ray diffraction pattern of (6R)-BH4 Form A.

Polymorph A which exhibits a characteristic X-ray powder diffraction pattern with characteristic peaks expressed in d-values (Å) of: 15.5 (vs), 12.0 (m), 6.7 (m), 6.5 (m), 6.3 (w), 6.1 (w), 5.96 (w), 5.49 (m), 4.89 (m), 3.79 (m), 3.70 (s), 3.48 (m), 3.45 (m), 3.33 (s), 3.26 (s), 3.22 (m), 3.18 (m), 3.08 (m), 3.02 (w), 2.95 (w), 2.87 (m), 2.79 (w), 2.70 (w). FIG. 2 is a graph of the characteristic X-ray diffraction pattern exhibited by form A of (6R)-L-erythro-tetrahydrobiopterin dihydrochloride.

Polymorph A exhibits a characteristic Raman spectra bands, expressed in wave numbers (cm-1) at: 2934 (w) 2880 (w), 1692 (s), 1683 (m), 1577 (w), 1462 (m), 1360 (w), 1237 (w), 1108 (w), 1005 (vw), 881 (vw), 813 (vw), 717 (m), 687 (m), 673 (m), 659 (m), 550 (w), 530 (w), 492 (m), 371 (m), 258 (w), 207 (w), 101 (s), 87 (s) cm-1.

Polymorph form A may be obtained by freeze drying or water removal of solutions of (6R)-L-erythro-tetrahydrobiopterin dihydrochloride in water. Polymorph form A of (6R)-L-erythro-tetrahydrobiopterin dihydrochloride can be prepared by dissolving (6R)-L-erythro-tetrahydrobiopterin dihydrochloride at ambient temperatures in water, (1) cooling the solution to low temperatures for solidifying the solution, and removing water under reduced pressure, or (2) removing water from said aqueous solution.

The crystalline form A can be isolated by filtration and then dried to evaporate absorbed water from the product. Drying conditions and methods are known and drying of the isolated product or water removal pursuant to variant (2) described herein may be carried out in applying elevated temperatures, for example up to 80° C., preferably in the range from 30° C. to 80° C., under vacuum or elevated temperatures and vacuum. Prior to isolation of a precipitate obtained in variant (2), the suspension may be stirred for a certain time for phase equilibration. The concentration of (6R)-L-erythro-tetrahydrobiopterin dihydrochloride in the aqueous solution may be from 5 to 40 percent by weight, by reference to the solution.

A fast cooling is preferred to obtain solid solutions as starting material. A reduced pressure is applied until the solvent is completely removed. Freeze drying is a technology well known in the art. The time to complete solvent removal is dependent on the applied vacuum, which may be from 0.01 to 1 mbar, the solvent used and the freezing temperature.

Polymorph form A is stable at room temperature or below room temperature under substantially water free conditions, which is demonstrated with phase equilibration tests of suspensions in tetrahydrofuran or tertiary-butyl methyl ether stirred for five days and 18 hours respectively under nitrogen at room temperature. Filtration and air drying at room temperature yields unchanged polymorph form A.

Polymorph Form F

It has been found that another crystal polymorph of (6R)-L-erythro-tetrahydrobiopterin dihydrochloride is a stable prefered form of BH4 for use in a pharmaceutical preparation described herein, which shall be referred to herein as "form F," or "polymorph F." Polymorph F is slightly hygroscopic and adsorbs water to a content of about 3 percent by weight, which is continuously released between 50° C. and 200° C., when heated at a rate of 10° C./minute. The polymorph F is a meta-stable form and a hygroscopic anhydrate, which is more stable than form A at ambient lower temperatures and less stable than form B at higher temperatures and form F is especially suitable as intermediate and starting material to produce stable polymorph forms. Polymorph form F can be prepared as a solid powder with desired medium particle size range which is typically ranging from 1 μm to about 500 μm.

Figure 3:
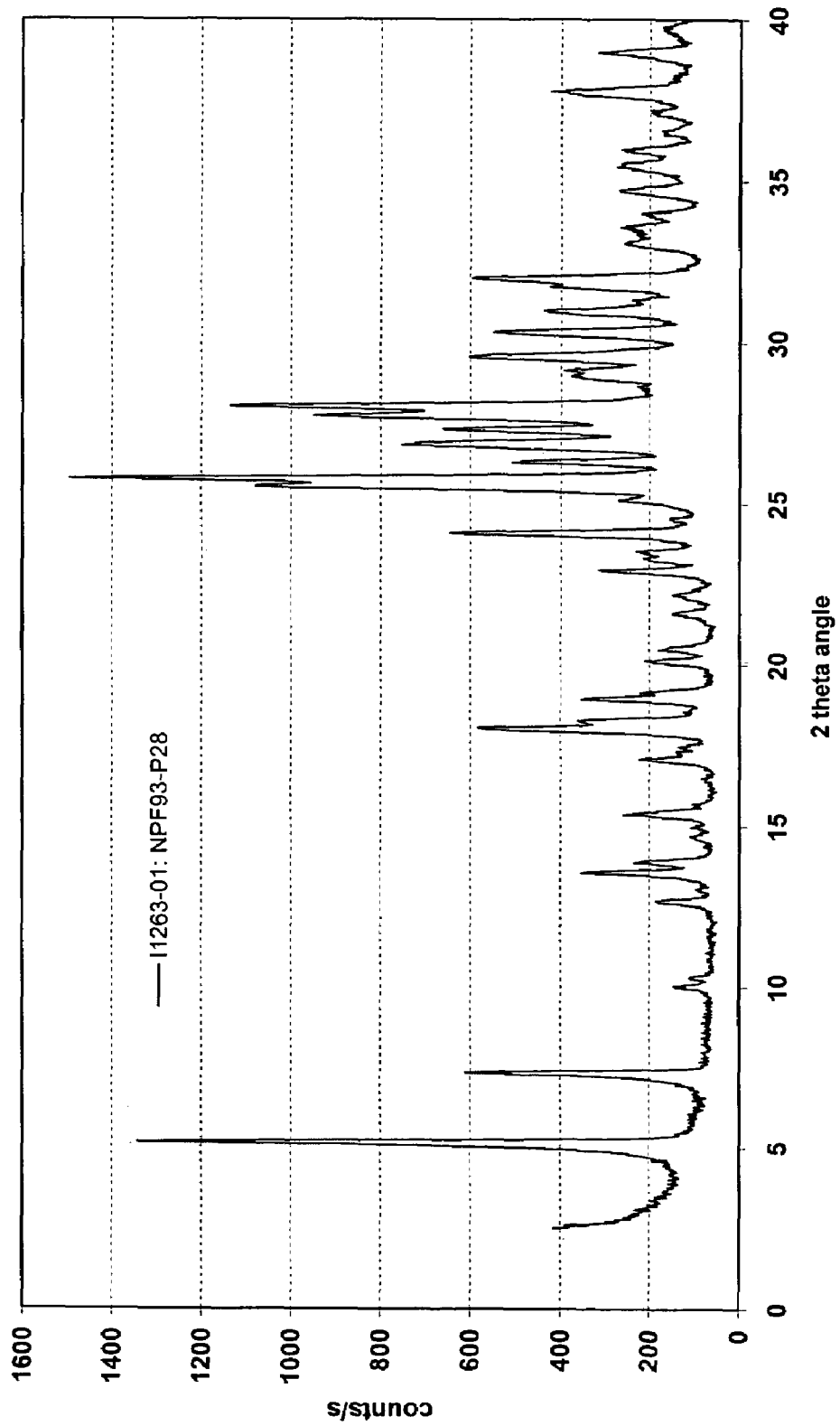
FIG. 3 is a powder X-ray diffraction pattern of (6R)-BH4 Form F.

Polymorph F exhibits a characteristic X-ray powder diffraction pattern with characteristic peaks expressed in d-values (Å) at: 17.1 (vs), 12.1 (w), 8.6 (w), 7.0 (w), 6.5 (w), 6.4 (w), 5.92 (w), 5.72 (w), 5.11 (w), 4.92 (m), 4.86 (w), 4.68 (m), 4.41 (w), 4.12 (w), 3.88 (w), 3.83 (w), 3.70 (m), 3.64 (w), 3.55 (m), 3.49 (s), 3.46 (vs), 3.39 (s), 3.33 (m), 3.31 (m), 3.27 (m), 3.21 (m), 3.19 (m), 3.09 (m), 3.02 (m), and 2.96 (m). FIG. 3 is a graph of the characteristic X-ray diffraction pattern exhibited by form F of (6R)-L-erythro-tetrahydrobiopterin dihydrochloride.

Polymorph F may be obtained by phase equilibration of suspensions of polymorph form A in suitable polar and non-aqueous solvents, which scarcely dissolve said lower energy forms, especially alcohols such as methanol, ethanol, propanol and isopropanol. Polymorph form F of (6R)-L-erythro-tetrahydrobiopterin dihydrochloride can also be prepared by dispersing particles of solid form A of (6R)-L-erythro-tetrahydrobiopterin dihydrochloride in a non-aqueous solvent that scarcely dissolves said (6R)-L-erythro-tetrahydrobiopterin dihydrochloride below room temperature, stirring the suspension at said temperatures for a time sufficient to produce polymorph form F, thereafter isolating crystalline form F and removing the solvent from the isolated form F. Removing of solvent and drying may be carried out under air, dry air or a dry protection gas such as nitrogen or noble gases and at or below room temperature, for example down to 0° C. The temperature during phase equilibration is preferably from 5 to 15° C. and most preferably about 10° C.

Polymorph Form J

It has been found that another crystal polymorph of (6R)-L-erythro-tetrahydrobiopterin dihydrochloride is a stable prefered form of BH4 for use in a pharmaceutical preparation described herein, which shall be referred to herein as "form J," or "polymorph J." The polymorph J is slightly hygroscopic and adsorbs water when handled at air humidity. The polymorph J is a meta-stable form and a hygroscopic anhydrate, and it can be transformed back into form E described below, from which it is obtained upon exposure to high relative humidity conditions such as above 75% relative humidity. Form J is especially suitable as intermediate and starting material to produce stable polymorph forms. Polymorph form J can be prepared as a solid powder with desired medium particle size range which is typically ranging from 1 μm to about 500 μm.

Figure 4:
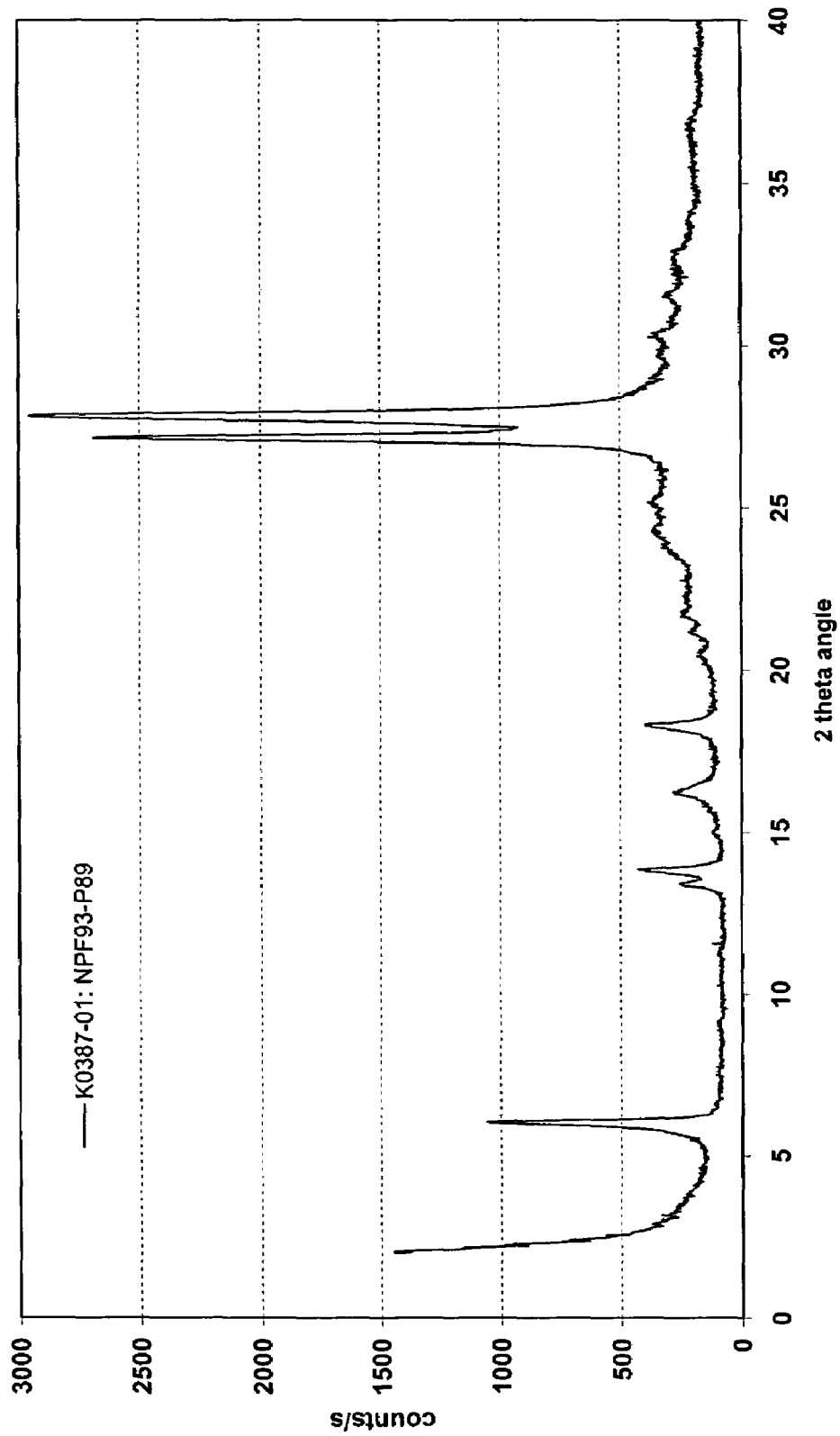
FIG. 4 is a powder X-ray diffraction pattern of (6R)-BH4 Form J.

Form J exhibits a characteristic X-ray powder diffraction pattern with characteristic peaks expressed in d-values (Å) at: 14.6 (m), 6.6 (w), 6.4 (w), 5.47 (w), 4.84 (w), 3.29 (vs), and 3.21 (vs). FIG. 4 is a graph of the characteristic X-ray diffraction pattern exhibited by form J of (6R)-L-erythro-tetrahydrobiopterin dihydrochloride.

Polymorph J may be obtained by dehydration of form E at moderate temperatures under vacuum. In particular, polymorph form J of (6R)-L-erythro-tetrahydrobiopterin dihydrochloride can be prepared by taking form E and removing the water from form E by treating form E in a vacuum drier to obtain form J at moderate temperatures which may mean a temperature in the range of 25 to 70° C., and most preferably 30 to 50° C.

Polymorph Form K

It has been found that another crystal polymorph of (6R)-L-erythro-tetrahydrobiopterin dihydrochloride is a stable prefered form of BH4 for use in a pharmaceutical preparation described herein, which shall be referred to herein as "form K," or "polymorph K." Polymorph K is slightly hygroscopic and adsorbs water to a content of about 2.0 percent by weight, which is continuously released between 50° C. and 100° C., when heated at a rate of 10° C./minute. The polymorph K is a meta-stable form and a hygroscopic anhydrate, which is less stable than form B at higher temperatures and form K is especially suitable as intermediate and starting material to produce stable polymorph forms, in particular form B. Polymorph form K can be prepared as a solid powder with desired medium particle size range which is typically ranging from 1 μm to about 500 μm.

Figure 5:
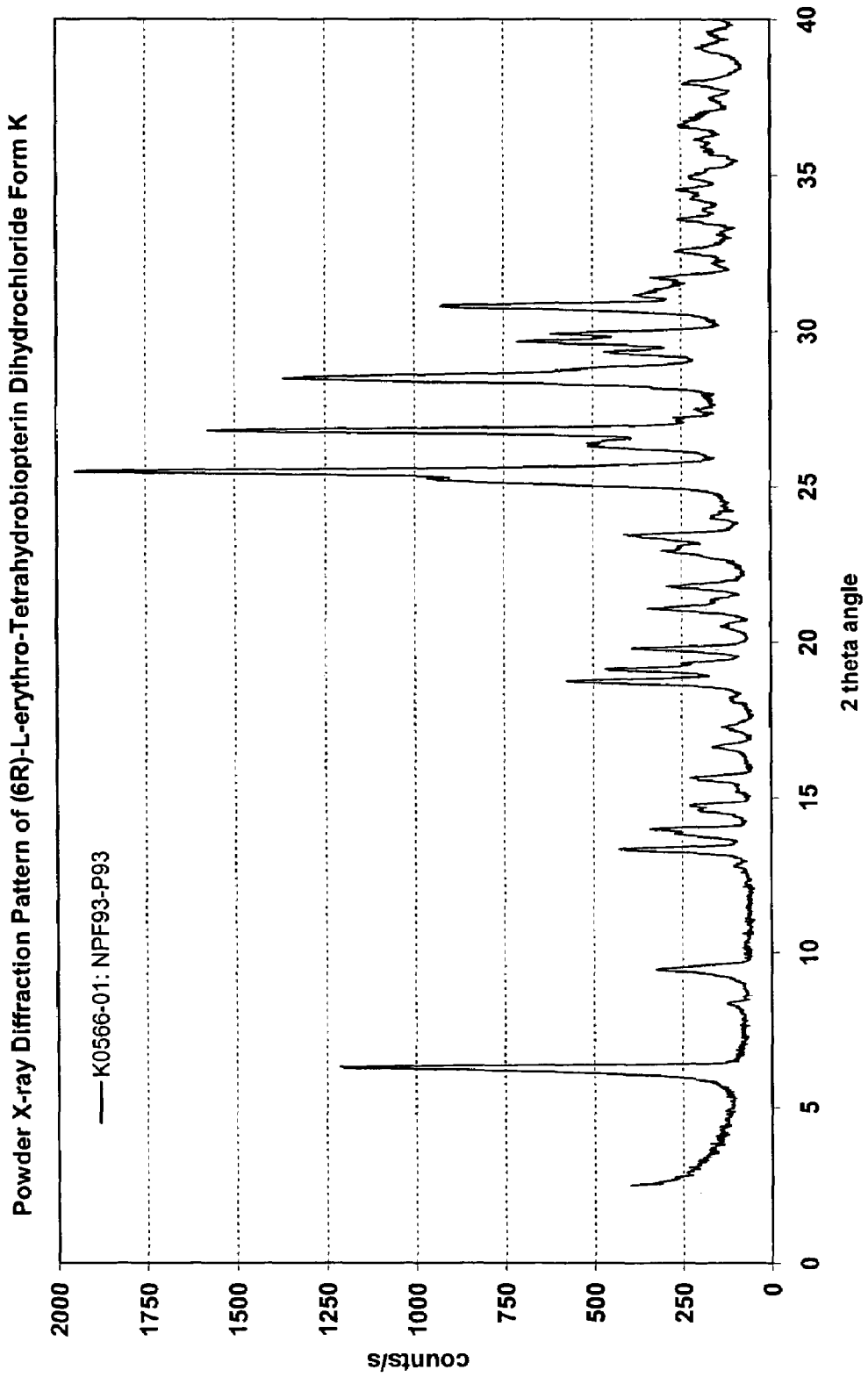
FIG. 5 is a powder X-ray diffraction pattern of (6R)-BH4 Form K.

Form K exhibits a characteristic X-ray powder diffraction pattern with characteristic peaks expressed in d-values (Å) at: 14.0 (s), 9.4 (w), 6.6 (w), 6.4 (w), 6.3 (w), 6.1 (w), 6.0 (w), 5.66 (w), 5.33 (w), 5.13 (vw), 4.73 (m), 4.64 (m), 4.48 (w), 4.32 (vw), 4.22 (w), 4.08 (w), 3.88 (w), 3.79 (w), 3.54 (m), 3.49 (vs), 3.39 (m), 3.33 (vs), 3.13 (s), 3.10 (m), 3.05 (m), 3.01 (m), 2.99 (m), and 2.90 (m). FIG. 5 is a graph of the characteristic X-ray diffraction pattern exhibited by form K of (6R)-L-erythro-tetrahydrobiopterin dihydrochloride.

Polymorph K may be obtained by crystallization from mixtures of polar solvents containing small amounts of water and in the presence of small amounts of ascorbic acid. Solvents for the solvent mixture may be selected from acetic acid and an alcohol such as methanol, ethanol, n- or isopropanol. In particular, polymorph form K of (6R)-L-erythro-tetrahydrobiopterin dihydrochloride can be prepared by dissolving (6R)-L-erythro-tetrahydrobiopterin dihydrochloride in a mixture of acetic acid and an alcohol or tetrahydrofuran containing small amounts of water and a small amount of ascorbic acid at elevated temperatures, lowering temperature below room temperature to crystallize said dihydrochloride, isolating the precipitate and drying the isolated precipitate at elevated temperature optionally under vacuum. Suitable alcohols are for example methanol, ethanol, propanol and isopropanol, whereby ethanol is preferred. The ratio of acetic acid to alcohol or tetrahydrofuran may be from 2:1 to 1:2 and preferably about 1:1. Dissolution of (6R)-L-erythro-tetrahydrobiopterin dihydrochloride can be carried out in presence of a higher water content and more of the anti-solvent mixture can be added to obtain complete precipitation. The amount of water in the final composition may be from 0.5 to 5 percent by weight and the amount of ascorbic acid may be from 0.01 to 0.5 percent by weight, both by reference to the solvent mixture. The temperature for dissolution may be in the range from 30 to 100 and preferably 35 to 70° C. and the drying temperature may be in the range from 30 to 50° C. The precipitate may be washed with an alcohol such as ethanol after isolation, e.g., filtration. The polymorph K can easily be converted in the most stable form B by phase equilibration in e.g. isopropanol and optionally seeding with form B crystals at above room temperature such as temperatures from 30 to 40° C.

Hydrate Forms of (6R) L-Tetrahydrobiopterin Dihydrochloride Salt

As further described below, it has been found that (6R)-L-erythro-tetrahydrobiopterin dihydrochloride exists as a number of crystalline hydrate, which shall be described and defined herein as forms C, D, E, H, and O. These hydrate forms are useful as a stable form of BH4 for the pharmaceutical preparations described herein and in the preparation of compositions including stable crystal polymorphs of BH4.

Hydrate Form C

It has been found that a hydrate crystal form of (6R)-L-erythro-tetrahydrobiopterin dihydrochloride is a stable prefered form of BH4 for use in a pharmaceutical preparation described herein, which shall be referred to herein as "form C," or "hydrate C." The hydrate form C is slightly hygroscopic and has a water content of approximately 5.5 percent by weight, which indicates that form C is a monohydrate. The hydrate C has a melting point near 94° C. ($\Delta H_f$ is about 31 J/g) and hydrate form C is especially suitable as intermediate and starting material to produce stable polymorphic forms. Polymorph form C can be prepared as a solid powder with desired medium particle size range which is typically ranging from 1 µm to about 500 µm.

Figure 6:
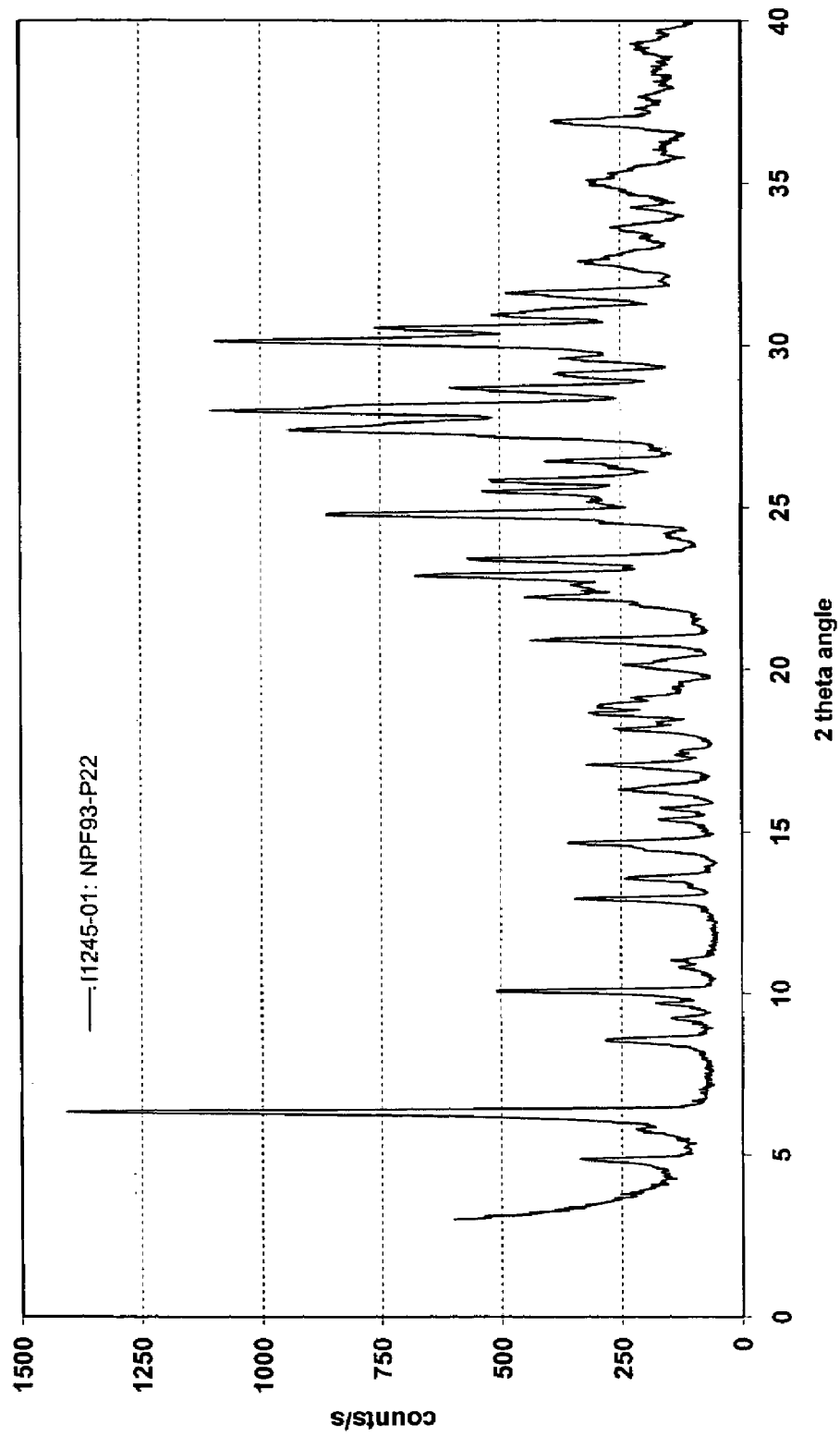
FIG. 6 is a powder X-ray diffraction pattern of (6R)-BH4 Form C.

Form C exhibits a characteristic X-ray powder diffraction pattern with characteristic peaks expressed in d-values (Å) at: 18.2 (m), 15.4 (w), 13.9 (vs), 10.4 (w), 9.6 (w), 9.1 (w), 8.8 (m), 8.2 (w), 8.0 (w), 6.8 (m), 6.5 (w), 6.05 (m), 5.77 (w), 5.64 (w), 5.44 (w), 5.19 (w), 4.89 (w), 4.76 (w), 4.70 (w), 4.41 (w), 4.25 (m), 4.00 (m), 3.88 (m), 3.80 (m), 3.59 (s), 3.50 (m), 3.44 (m), 3.37 (m), 3.26 (s), 3.19 (vs), 3.17 (s), 3.11 (m), 3.06 (m), 3.02 (m), 2.97 (vs), 2.93 (m), 2.89 (m), 2.83 (m), and 2.43 (m). FIG. 6 is a graph of the characteristic X-ray diffraction pattern exhibited by hydrate form C of (6R)-L-erythro-tetrahydrobiopterin dihydrochloride.

Hydrate form C may be obtained by phase equilibration at ambient temperatures of a polymorph form such as polymorph B suspension in a non-solvent which contains water in an amount of preferably about 5 percent by weight, by reference to the solvent. Hydrate form C of (6R)-L-erythro-tetrahydrobiopterin dihydrochloride cab be prepared by suspending (6R)-L-erythro-tetrahydrobiopterin dihydrochloride in a non-solvent such as, heptane, C1-C4-alcohols such as methanol, ethanol, 1- or 2-propanol, acetates, such as ethyl acetate, acetonitrile, acetic acid or ethers such as terahydrofuran, dioxane, tertiary-butyl methyl ether, or binary or ternary mixtures of such non-solvents, to which sufficient water is added to form a monohydrate, and stirring the suspension at or below ambient temperatures (e.g., 0 to 30° C.) for a time sufficient to form a monohydrate. Sufficient water may mean from 1 to 10 and preferably from 3 to 8 percent by weight of water, by reference to the amount of solvent. The solids may be filtered off and dried in air at about room temperature. The solid can absorb some water and therefore possess a higher water content than the theoretical value of 5.5 percent by weight. Hydrate form C is unstable with respect to forms D and B, and easily converted to polymorph form B at temperatures of about 40° C. in air and lower relative humidity. Form C can be transformed into the more stable hydrate D by suspension equilibration at room temperature.

Hydrate Form D

It has been found that another hydrate crystal form of (6R)-L-erythro-tetrahydrobiopterin dihydrochloride is a stable prefered form of BH4 for use in a pharmaceutical preparation described herein, which shall be referred to herein as "form D," or "hydrate D." The hydrate form D is slightly hygroscopic and may have a water content of approximately 5.0 to 7.0 percent by weight, which suggests that form D is a monohydrate. The hydrate D has a melting point near 153° C. ($\Delta H_f$ is about 111 J/g) and is of much higher stability than form C and is even stable when exposed to air humidity at ambient temperature. Hydrate form D can therefore either be used to prepare formulations or as intermediate and starting material to produce stable polymorph forms. Polymorph form D can be prepared as a solid powder with desired medium particle size range which is typically ranging from 1 µm to about 500 µm.

Figure 7:
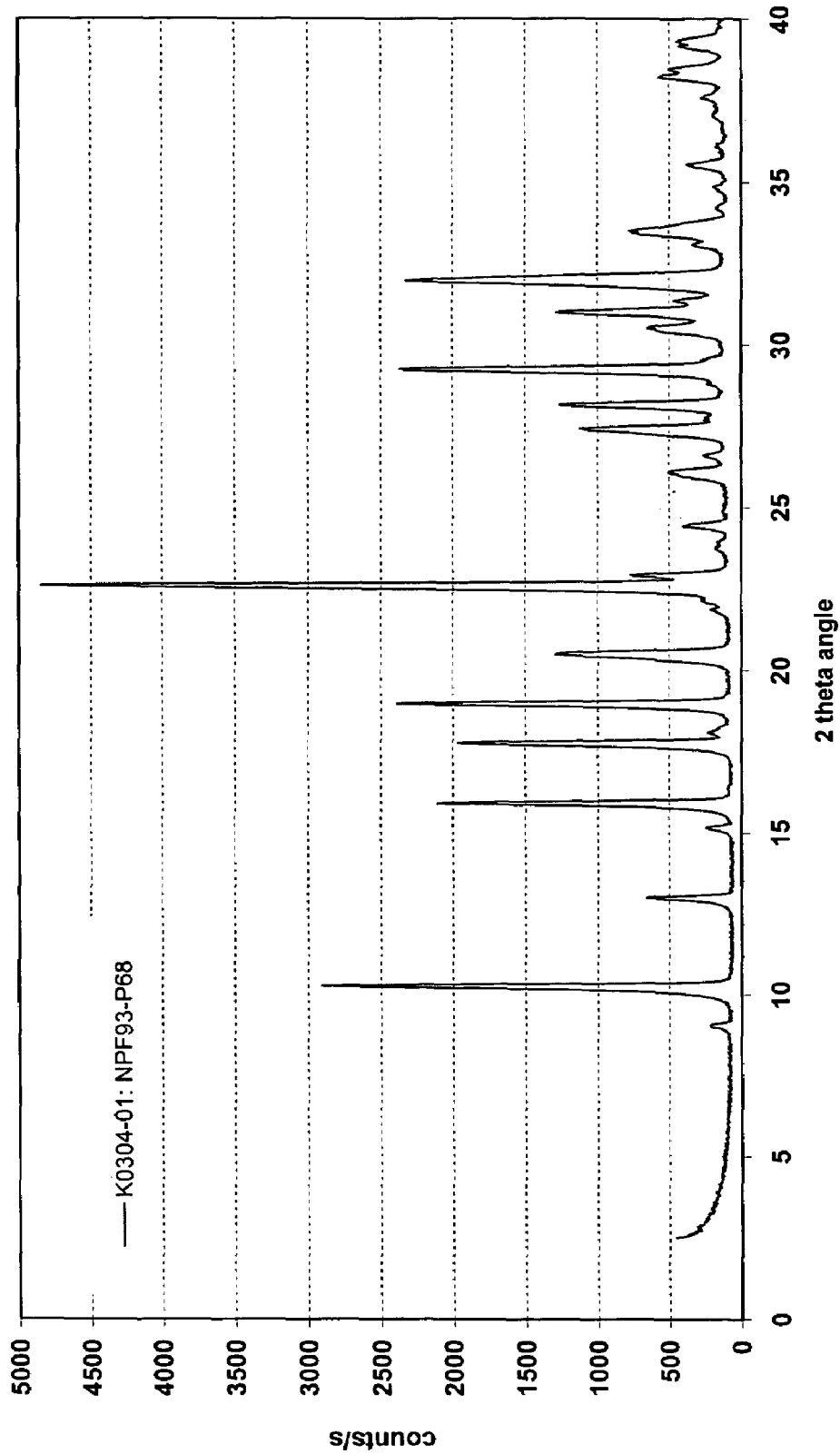
FIG. 7 is a powder X-ray diffraction pattern of (6R)-BH4 Form D.

Form D exhibits a characteristic X-ray powder diffraction pattern with characteristic peaks expressed in d-values (Å) at: 8.6 (s), 6.8 (w), 5.56 (m), 4.99 (m), 4.67 (s), 4.32 (m), 3.93 (vs), 3.88 (w), 3.64 (w), 3.41 (w), 3.25 (w), 3.17 (m), 3.05 (s), 2.94 (w), 2.92 (w), 2.88 (m), 2.85 (w), 2.80 (w), 2.79 (m), 2.68 (w), 2.65 (w), 2.52 (vw), 2.35 (w), 2.34 (w), 2.30 (w), and 2.29 (w). FIG. 7 is a graph of the characteristic X-ray diffraction pattern exhibited by hydrate form D of (6R)-L-erythro-tetrahydrobiopterin dihydrochloride.

Hydrate form D may be obtained by adding at about room temperature concentrated aqueous solutions of (6R)-L-erythro-tetrahydrobiopterin dihydrochloride to an excess of a non-solvent such as hexane, heptane, dichloromethane, 1- or 2-propanol, acetone, ethyl acetate, acetonitrile, acetic acid or ethers such as terahydrofuran, dioxane, tertiary-butyl methyl ether, or mixtures of such non-solvents, and stirring the suspension at ambient temperatures. The crystalline solid can be filtered off and then dried under dry nitrogen at ambient temperatures. A preferred non-solvent is isopropanol. The addition of the aqueous solution may carried out drop-wise to avoid a sudden precipitation. Hydrate form D of (6R)-L-erythro-tetrahydrobiopterin dihydrochloride can be prepared by adding at about room temperature a concentrated aqueous solutions of (6R)-L-erythro-tetrahydrobiopterin dihydrochloride to an excess of a non-solvent and stirring the suspension at ambient temperatures. Excess of non-solvent may mean a ratio of aqueous to the non solvent from 1:10 to 1:1000. Form D contains a small excess of water, related to the monohydrate, and it is believed that it is absorbed water due to the slightly hygroscopic nature of this crystalline hydrate. Hydrate form D is deemed to be the most stable one under the known hydrates at ambient temperatures and a relative humidity of less than 70%. Hydrate form D may be used for formulations prepared under conditions, where this hydrate is stable. Ambient temperature may mean 20 to 30° C.

Hydrate Form E

It has been found that another hydrate crystal form of (6R)-L-erythro-tetrahydrobiopterin dihydrochloride is a stable prefered form of BH4 for use in a pharmaceutical preparation described herein, which shall be referred to herein as "form E," or "hydrate E." The hydrate form E has a water content of approximately 10 to 14 percent by weight, which suggests that form E is a dihydrate. The hydrate E is formed at temperatures below room temperature. Hydrate form E is especially suitable as intermediate and starting material to produce stable polymorph forms. It is especially suitable to produce the water-free form J upon drying under nitrogen or optionally under vacuum. Form E is non-hygroscopic and stable under rather high relative humidities, i.e., at relative humidities above about 60% and up to about 85%. Polymorph form E can be prepared as a solid powder with desired medium particle size range which is typically ranging from 1 µm to about 500 µm.

Figure 8:
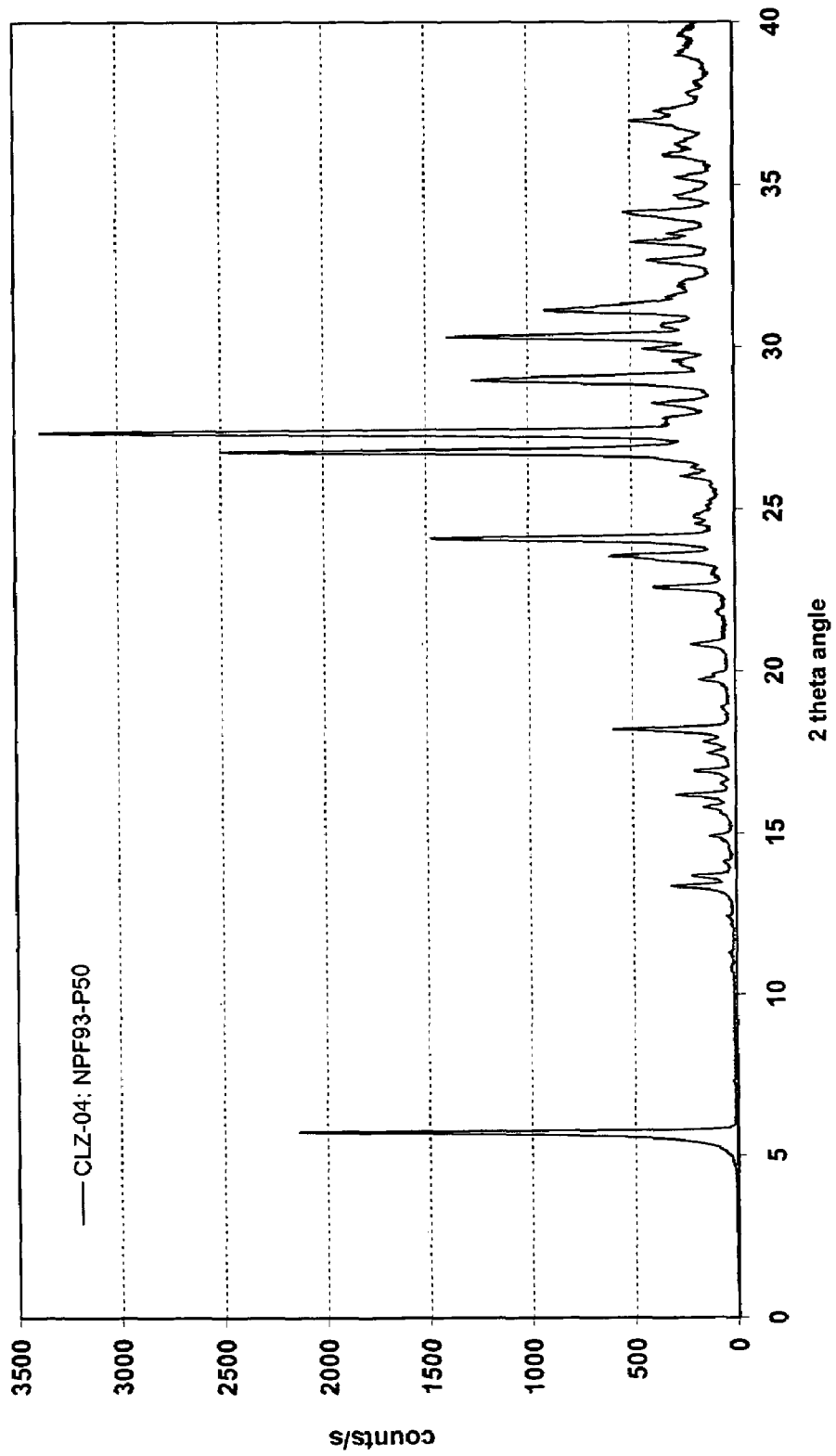
FIG. 8 is a powder X-ray diffraction pattern of (6R)-BH4 Form E.

Form E exhibits a characteristic X-ray powder diffraction pattern with characteristic peaks expressed in d-values (Å) at: 15.4 (s), 6.6 (w), 6.5 (w), 5.95 (vw), 5.61 (vw), 5.48 (w), 5.24 (w), 4.87 (w), 4.50 (vw), 4.27 (w), 3.94 (w), 3.78 (w), 3.69 (m), 3.60 (w), 3.33 (s), 3.26 (vs), 3.16 (w), 3.08 (m), 2.98 (w), 2.95 (m), 2.91 (w), 2.87 (m), 2.79 (w), 2.74 (w), 2.69 (w), and 2.62 (w). FIG. 8 is a graph of the characteristic X-ray diffraction pattern exhibited by hydrate form E of (6R)-L-erythro-tetrahydrobiopterin dihydrochloride.

Hydrate form E may be obtained by adding concentrated aqueous solutions of (6R)-L-erythro-tetrahydrobiopterin dihydrochloride to an excess of a non-solvent cooled to temperatures from about 10 to −10° C. and preferably between 0 to 10° C. and stirring the suspension at said temperatures. The crystalline solid can be filtered off and then dried under dry nitrogen at ambient temperatures. Non-solvents are for example such as hexane, heptane, dichloromethane, 1- or 2-propanol, acetone, ethyl acetate, acetonitrile, acetic acid or ethers such as terahydrofuran, dioxane, tertiary-butyl methyl ether, or mixtures of such non-solvents. A preferred non-solvent is isopropanol. The addition of the aqueous solution may carried out drop-wise to avoid a sudden precipitation. Hydrate form E of (6R)-L-erythro-tetrahydrobiopterin dihydrochloride can be prepared by adding a concentrated aqueous solutions of (6R)-L-erythro-tetrahydrobiopterin dihydrochloride to an excess of a non-solvent which is cooled to temperatures from about 10 to −10° C., and stirring the suspension at ambient temperatures. Excess of non-solvent may mean a ratio of aqueous to the non solvent from 1:10 to 1:1000. A preferred non-solvent is tetrahydrofuran. Another preparation process comprises exposing polymorph form B to an air atmosphere with a relative humidity of 70 to 90%, preferably about 80%. Hydrate form E is deemed to be a dihydrate, whereby some additional water may be absorbed. Polymorph form E can be transformed into polymorph J upon drying under vacuum at moderate temperatures, which may mean between 20° C. and 50° C. at pressures between 0 and 100 mbar. Form E is especially suitable for formulations in semi solid forms because of its stability at high relative humidities.

Hydrate Form H

It has been found that another hydrate crystal form of (6R)-L-erythro-tetrahydrobiopterin dihydrochloride is a stable prefered form of BH4 for use in a pharmaceutical preparation described herein, which shall be referred to herein as "form H," or "hydrate H." The hydrate form H has a water content of approximately 5.0 to 7.0 percent by weight, which suggests that form H is a hygroscopic monohydrate. The hydrate form H is formed at temperatures below room temperature. Hydrate form H is especially suitable as intermediate and starting material to produce stable polymorph forms. Polymorph form H can be prepared as a solid powder with desired medium particle size range which is typically ranging from 1 µm to about 500 µm.

Figure 9:
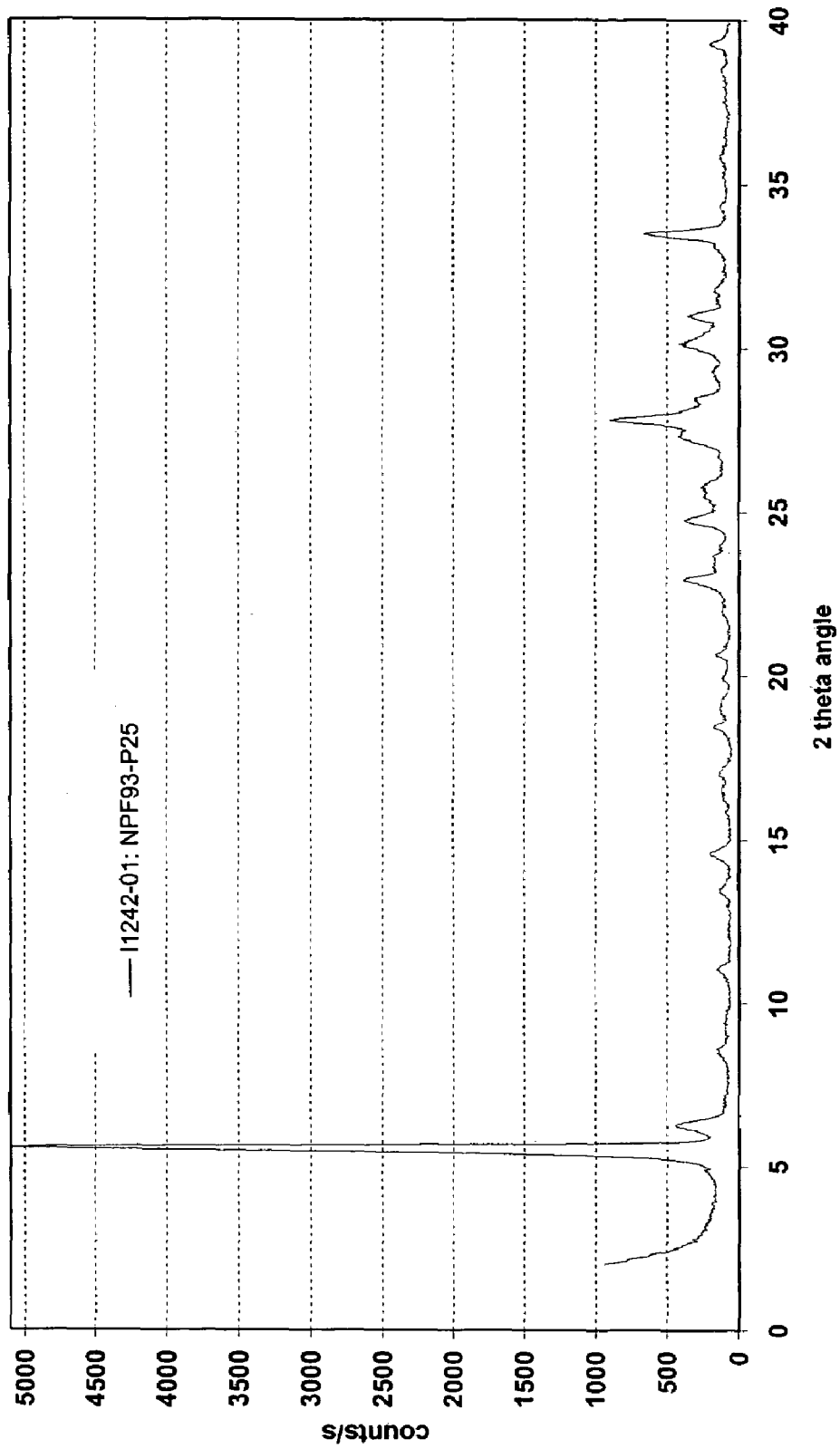
FIG. 9 is a powder X-ray diffraction pattern of (6R)-BH4 Form H.

Form H exhibits a characteristic X-ray powder diffraction pattern with characteristic peaks expressed in d-values (Å) at: 8.6 15.8 (vs), 10.3 (w), 8.0 (w), 6.6 (w), 6.07 (w), 4.81 (w), 4.30 (w), 3.87 (m), 3.60 (m), 3.27 (m), 3.21 (m), 3.13 (w), 3.05 (w), 2.96 (m), 2.89 (m), 2.82 (w), and 2.67 (m). FIG. 9 is a graph of the characteristic X-ray diffraction pattern exhibited by hydrate form H of (6R)-L-erythro-tetrahydrobiopterin dihydrochloride.

Hydrate form H may be obtained by dissolving at ambient temperatures (6R)-L-erythro-tetrahydrobiopterin dihydrochloride in a mixture of acetic acid and water, adding then a non-solvent to precipitate a crystalline solid, cooling the obtained suspension and stirring the cooled suspension for a certain time. The crystalline solid is filtered off and then dried under vacuum at ambient temperatures. Non-solvents are for example such as hexane, heptane, dichloromethane, 1- or 2-propanol, acetone, ethyl acetate, acetonitril, acetic acid or ethers such as terahydrofuran, dioxane, tertiary-butyl methyl ether, or mixtures of such non-solvents. A preferred non-solvent is tetrahydrofuran. Hydrate form H of (6R)-L-erythro-tetrahydrobiopterin dihydrochloride can be by prepared by dissolving at ambient temperatures (6R)-L-erythro-tetrahydrobiopterin dihydrochloride in a mixture of acetic acid and a less amount than that of acetic acid of water, adding a non-solvent and cooling the obtained suspension to temperatures in the range of −10 to 10° C., and preferably −5 to 5° C., and stirring the suspension at said temperature for a certain time. Certain time may mean 1 to 20 hours. The weight ratio of acetic acid to water may be from 2:1 to 25:1 and preferably 5:1 to 15:1. The weight ratio of acetic acid/water to the non-solvent may be from 1:2 to 1:5. Hydrate form H seems to be a monohydrate with a slight excess of water absorbed due to the hygroscopic nature.

Hydrate Form O

It has been found that another hydrate crystal form of (6R)-L-erythro-tetrahydrobiopterin dihydrochloride is a stable prefered form of BH4 for use in a pharmaceutical preparation described herein, which shall be referred to herein as "form O," or "hydrate O." The hydrate form O is formed at temperatures near room temperature. Hydrate form O is especially suitable as intermediate and starting material to produce stable polymorph forms. Polymorph form O can be prepared as a solid powder with desired medium particle size range which is typically ranging from 1 µm to about 500 µm.

Figure 10:
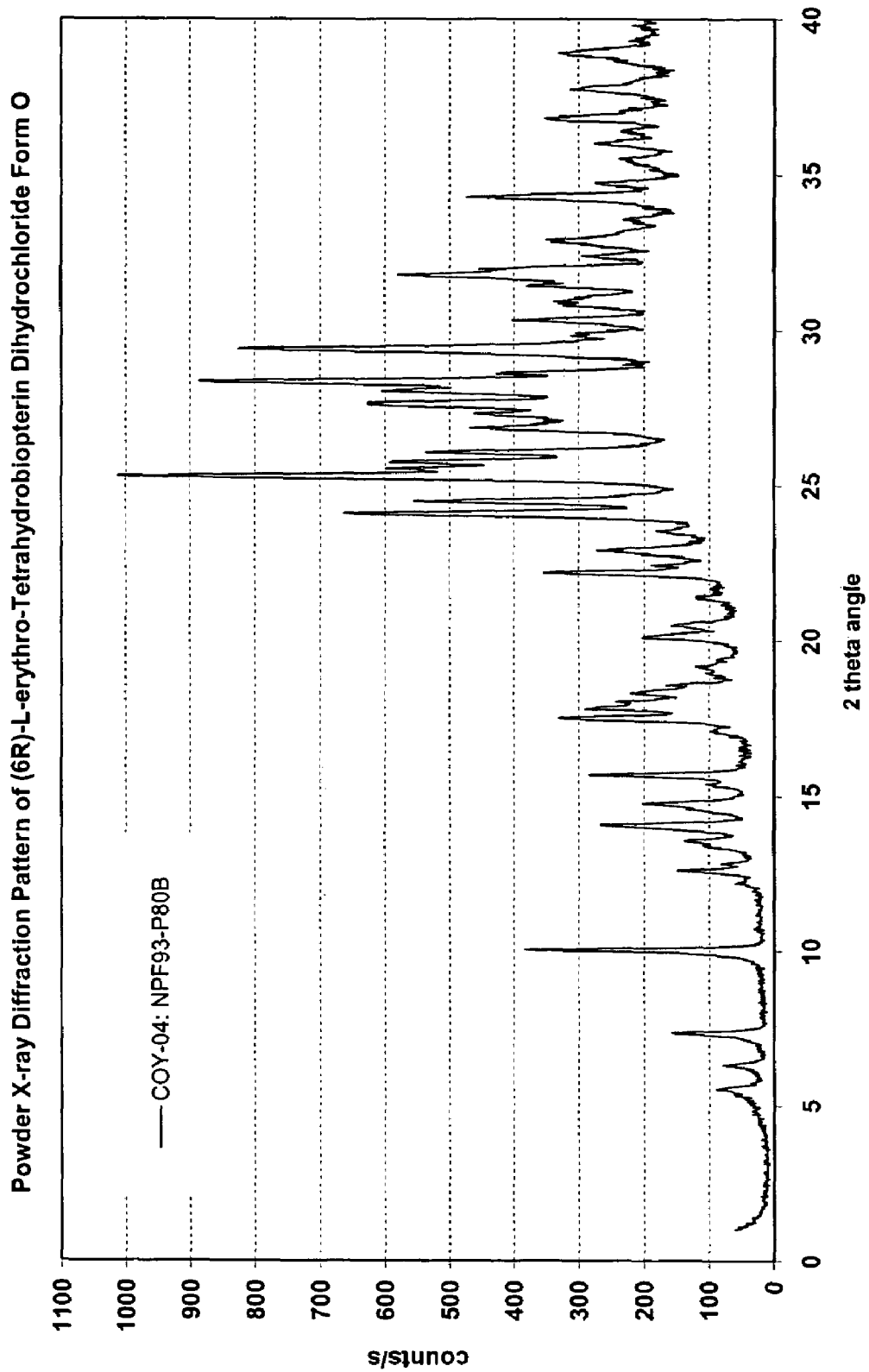
FIG. 10 is a powder X-ray diffraction pattern of (6R)-BH4 Form O.

Form O exhibits a characteristic X-ray powder diffraction pattern with characteristic peaks expressed in d-values (Å) at: 15.9 (w), 14.0 (w), 12.0 (w), 8.8 (m), 7.0 (w), 6.5 (w), 6.3 (m), 6.00 (w), 5.75 (w), 5.65 (m), 5.06 (m), 4.98 (m), 4.92 (m), 4.84 (w), 4.77 (w), 4.42 (w), 4.33 (w), 4.00 (m), 3.88 (m), 3.78 (w), 3.69 (s), 3.64 (s), 3.52 (vs), 3.49 (s), 3.46 (s), 3.42 (s), 3.32 (m), 3.27 (m), 3.23 (s), 3.18 (s), 3.15 (vs), 3.12 (m), 3.04 (vs), 2.95 (m), 2.81 (s), 2.72 (m), 2.67 (m), and 2.61 (m). FIG. 10 is a graph of the characteristic X-ray diffraction pattern exhibited by hydrate form O of (6R)-L-erythro-tetrahydrobiopterin dihydrochloride.

Hydrate form O can be prepared by exposure of polymorphic form F to a nitrogen atmosphere containing water vapor with a resulting relative humidity of about 52% for about 24 hours. The fact that form F, which is a slightly hygroscopic anhydrate, can be used to prepare form O under 52% relative humidity suggests that form O is a hydrate, which is more stable than form F under ambient temperature and humidity conditions.

Solvate-Forms of (6R) L-Tetrahydrobiopterin Dihydrochloride Salt

As further described below, it has been found that (6R)-L-erythro-tetrahydrobiopterin dihydrochloride exists as a number of crystalline solvate forms, which shall be described and defined herein as forms G, I, L, M, and N. These solvate forms are useful as a stable form of BH4 for the pharmaceutical preparations described herein and in the preparation of compositions including stable crystal polymorphs of BH4.

Solvate Form G

It has been found that an ethanol solvate crystal form of (6R)-L-erythro-tetrahydrobiopterin dihydrochloride is a stable preferred form of BH4 for use in a pharmaceutical preparation described herein, which shall be referred to herein as "form G," or "hydrate G." The ethanol solvate form G has a ethanol content of approximately 8.0 to 12.5 percent by weight, which suggests that form G is a hygroscopic mono ethanol solvate. The solvate form G is formed at temperatures below room temperature. Form G is especially suitable as intermediate and starting material to produce stable polymorph forms. Polymorph form G can be prepared as a solid powder with a desired medium particle size range which is typically ranging from 1 μm to about 500 μm.

Figure 11:
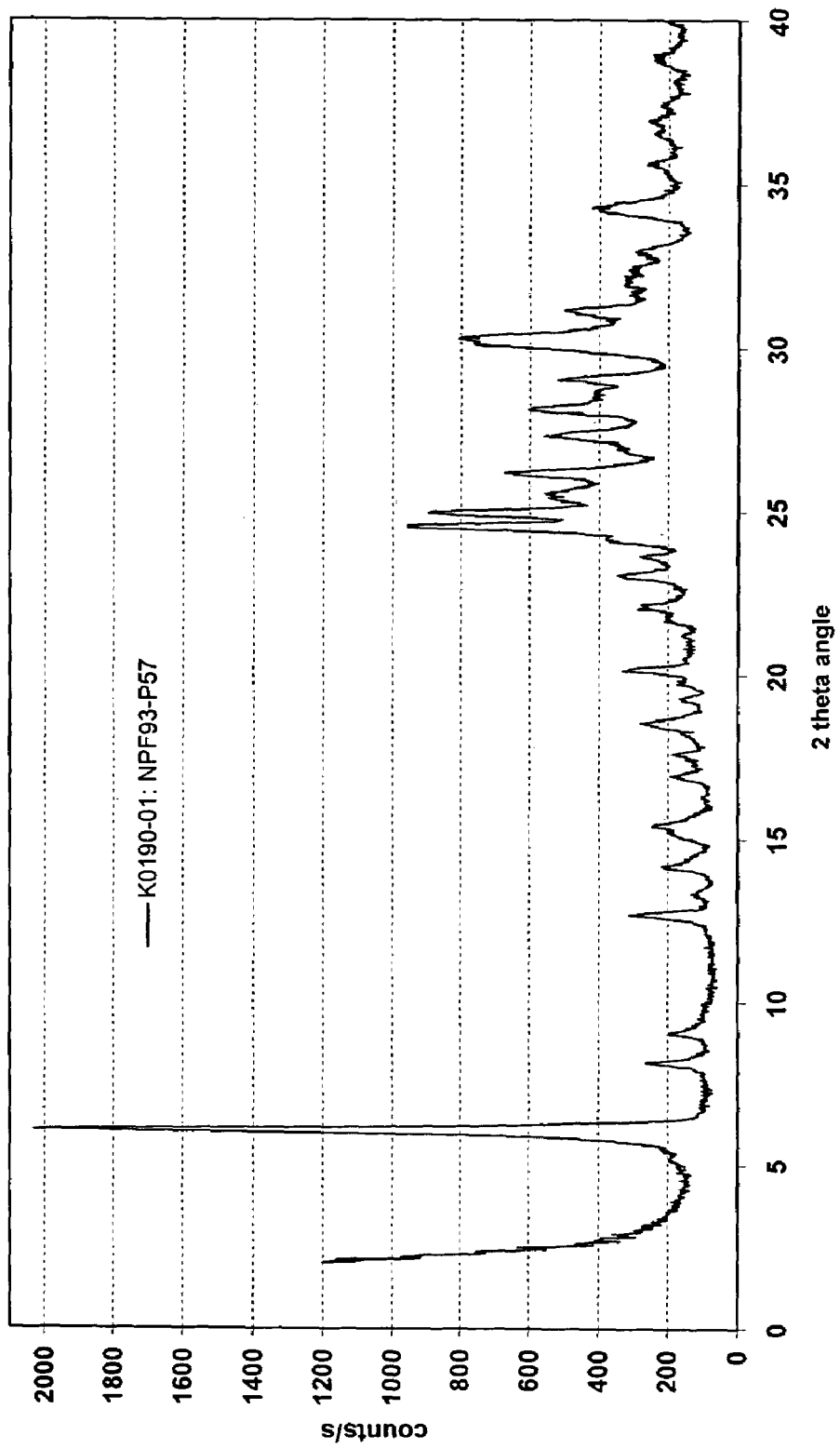
FIG. 11 is a powder X-ray diffraction pattern of (6R)-BH4 Form G.

Form G exhibits a characteristic X-ray powder diffraction pattern with characteristic peaks expressed in d-values (Å) at: 14.5 (vs), 10.9 (w), 9.8 (w), 7.0 (w), 6.3 (w), 5.74 (w), 5.24 (vw), 5.04 (vw), 4.79 (w), 4.41 (w), 4.02 (w), 3.86 (w), 3.77 (w), 3.69 (w), 3.63 (m), 3.57 (m), 3.49 (m), 3.41 (m), 3.26 (m), 3.17 (m), 3.07 (m), 2.97 (m), 2.95 (m), 2.87 (w), and 2.61 (w). FIG. 11 is a graph of the characteristic X-ray diffraction pattern exhibited by solvate form G of (6R)-L-erythro-tetrahydrobiopterin dihydrochloride.

Ethanol solvate form G may be obtained by crystallization of L-erythro-tetrahydrobiopterin dihydrochloride dissolved in water and adding a large excess of ethanol, stirring the obtained suspension at or below ambient temperatures and drying the isolated solid under air or nitrogen at about room temperature. Here, a large excess of ethanol means a resulting mixture of ethanol and water with less than 10% water, preferably about 3 to 6%. Ethanolate form G of (6R)-L-erythro-tetrahydrobiopterin dihydrochloride can be prepared by dissolving at about room temperature to temperatures of 75° C. (6R)-L-erythro-tetrahydrobiopterin dihydrochloride in water or in a mixture of water and ethanol, cooling a heated solution to room temperature and down to 5 to 10° C., adding optionally ethanol to complete precipitation, stirring the obtained suspension at temperatures of 20 to 5° C., filtering off the white, crystalline solid and drying the solid under air or a protection gas such as nitrogen at temperatures about room temperature. The process may be carried out in a first variant in dissolving (6R)-L-erythro-tetrahydrobiopterin dihydrochloride at about room temperature in a lower amount of water and then adding an excess of ethanol and then stirring the obtained suspension for a time sufficient for phase equilibration. In a second variant, (6R)-L-erythro-tetrahydrobiopterin dihydrochloride may be suspended in ethanol, optionally adding a lower amount of water, and heating the suspension and dissolute (6R)-L-erythro-tetrahydrobiopterin dihydrochloride, cooling down the solution to temperatures of about 5 to 15° C., adding additional ethanol to the suspension and then stirring the obtained suspension for a time sufficient for phase equilibration.

Solvate Form I

It has been found that an acetic acid solvate crystal form of (6R)-L-erythro-tetrahydrobiopterin dihydrochloride is a stable preferred form of BH4 for use in a pharmaceutical preparation described herein, which shall be referred to herein as "form I," or "hydrate I." The acetic acid solvate form I has an acetic acid content of approximately 12.7 percent by weight, which suggests that form I is a hygroscopic acetic acid mono solvate. The solvate form I is formed at temperatures below room temperature. Acetic acid solvate form I is especially suitable as intermediate and starting material to produce stable polymorph forms. Polymorph form I can be prepared as a solid powder with desired medium particle size range which is typically ranging from 1 μm to about 500 μm.

Figure 12:
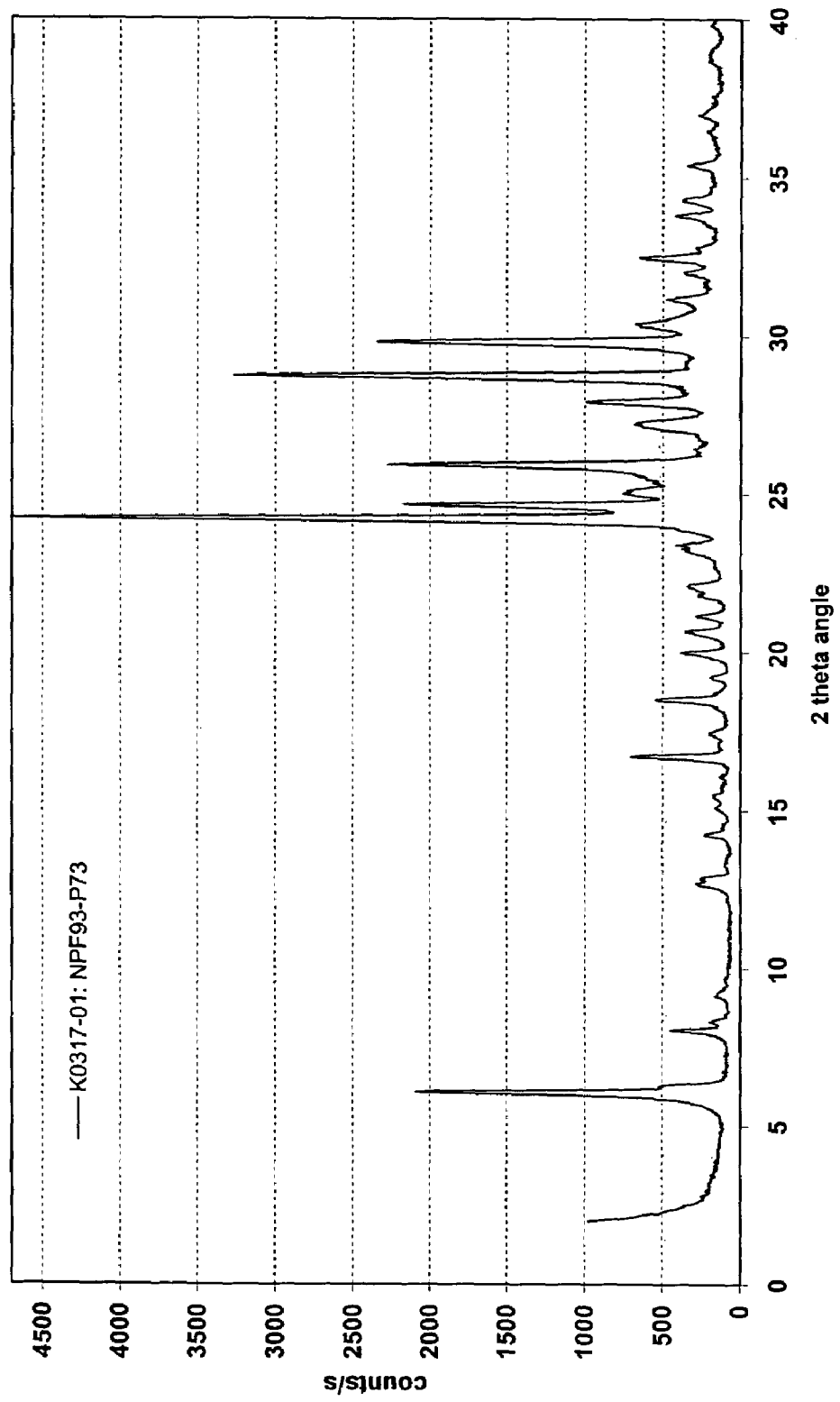
FIG. 12 is a powder X-ray diffraction pattern of (6R)-BH4 Form I.

Form I exhibits a characteristic X-ray powder diffraction pattern with characteristic peaks expressed in d-values (Å) at: 14.5 (m), 14.0 (w), 11.0 (w), 7.0 (vw), 6.9 (vw), 6.2 (vw), 5.30 (w), 4.79 (w), 4.44 (w), 4.29 (w), 4.20 (vw), 4.02 (w), 3.84 (w), 3.80 (w), 3.67 (vs), 3.61 (m)+3.56 (w), 3.44 (m), 3.27 (w), 3.19 (w), 3.11 (s), 3.00 (m), 2.94 (w), 2.87 (w), and 2.80 (w). FIG. 12 is a graph of the characteristic X-ray diffraction pattern exhibited by solvate form I of (6R)-L-erythro-tetrahydrobiopterin dihydrochloride.

Acetic acid solvate form I may be obtained by dissolution of L-erythro-tetrahydrobiopterin dihydrochloride in a mixture of acetic acid and water at elevated temperature, adding further acetic acid to the solution, cooling down to a temperature of about 10° C., then warming up the formed suspension to about 15° C., and then stirring the obtained suspension for a time sufficient for phase equilibration, which may last up to 3 days. The crystalline solid is then filtered off and dried under air or a protection gas such as nitrogen at temperatures about room temperature.

Solvate Form L

It has been found that a mixed ethanol solvate/hydrate crystal form of (6R)-L-erythro-tetrahydrobiopterin dihydrochloride is a stable prefered form of BH4 for use in a pharmaceutical preparation described herein, which shall be referred to herein as "form L," or "hydrate L." Form L may contain 4% but up to 13% ethanol and 0% to about 6% of water. Form L may be transformed into form G when treated in ethanol at temperatures from about 0° C. to 20° C. In addition form L may be transformed into form B when treated in an organic solvent at ambient temperatures (10° C. to 60° C.). Polymorph form L can be prepared as a solid powder with desired medium particle size range which is typically ranging from 1 μm to about 500 μm.

Figure 13:
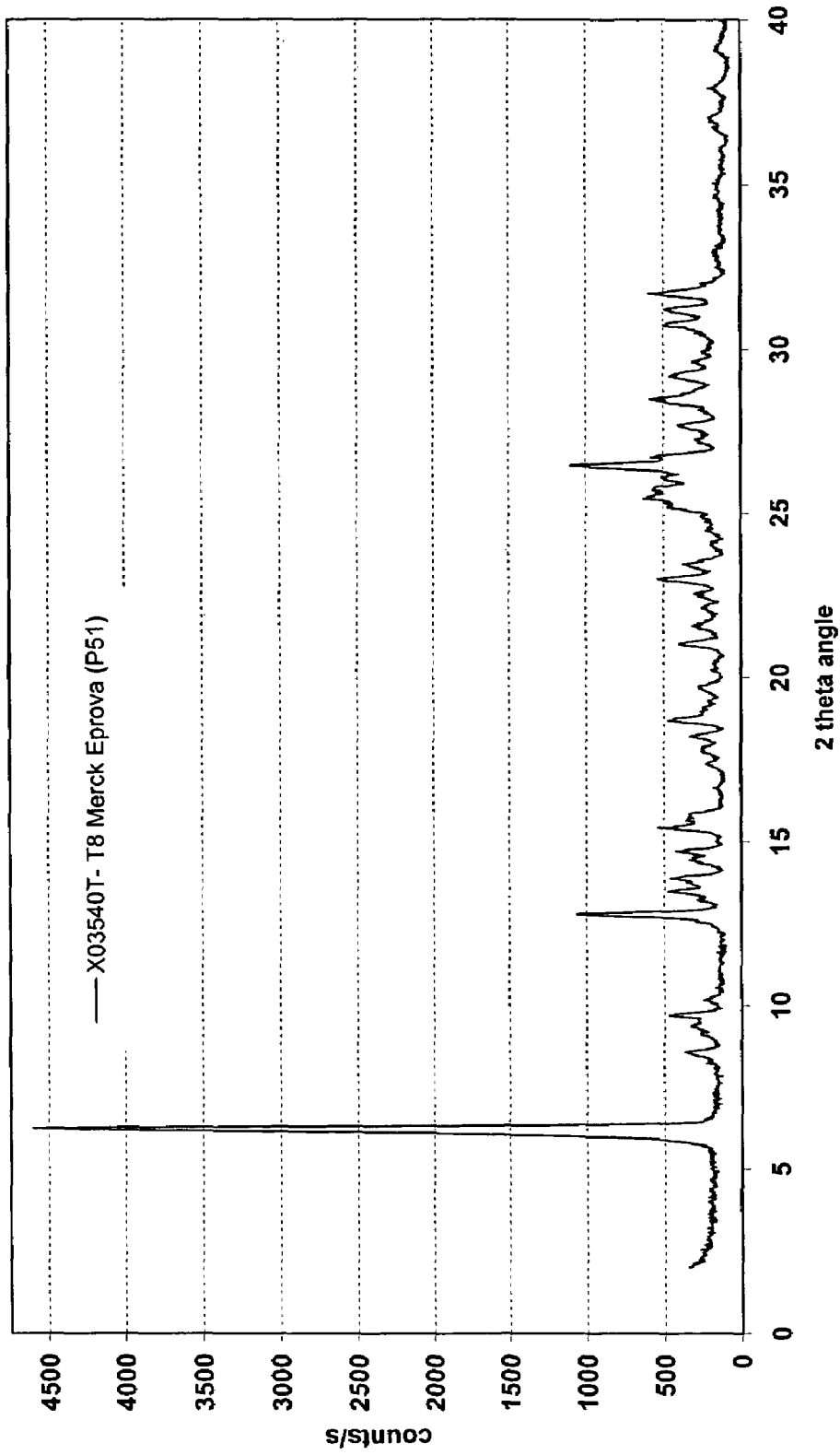
FIG. 13 is a powder X-ray diffraction pattern of (6R)-BH4 Form L.

Form L exhibits a characteristic X-ray powder diffraction pattern with characteristic peaks expressed in d-values (Å) at: 14.1 (vs), 10.4 (w), 9.5 (w), 9.0 (vw), 6.9 (w), 6.5 (w), 6.1 (w), 5.75 (w), 5.61 (w), 5.08 (w), 4.71 (w), 3.86 (w), 3.78 (w), 3.46 (m), 3.36 (m), 3.06 (w), 2.90 (w), and 2.82 (w). FIG. 13 is a graph of the characteristic X-ray diffraction pattern exhibited by solvate form L of (6R)-L-erythro-tetrahydrobiopterin dihydrochloride.

Form L may be obtained by suspending hydrate form E at room temperature in ethanol and stirring the suspension at temperatures from 0 to 10° C., preferably about 5° C., for a time sufficient for phase equilibration, which may be 10 to 20 hours. The crystalline solid is then filtered off and dried preferably under reduced pressure at 30° C. or under nitrogen. Analysis by TG-FTIR suggests that form L may contain variable amounts of ethanol and water, i.e., it can exist as an polymorph (anhydrate), as a mixed ethanol solvate/hydrate, or even as a hydrate.

Solvate Form M

It has been found that an ethanol solvate crystal form of (6R)-L-erythro-tetrahydrobiopterin dihydrochloride is a stable prefered form of BH4 for use in a pharmaceutical preparation described herein, which shall be referred to herein as "form M," or "hydrate M." Form M may contain 4% but up to 13% ethanol and 0% to about 6% of water, which suggests that form M is a slightly hygroscopic ethanol solvate. The solvate form M is formed at room temperature. Form M is especially suitable as intermediate and starting material to produce stable polymorph forms, since form M can be transformed into form G when treated in ethanol at temperatures between about −10° to 15° C., and into form B when treated in organic solvents such as ethanol, C3 and C4 alcohols, or cyclic ethers such as THF and dioxane. Polymorph form M can be prepared as a solid powder with desired medium particle size range which is typically ranging from 1 μm to about 500 μm.

Figure 14:
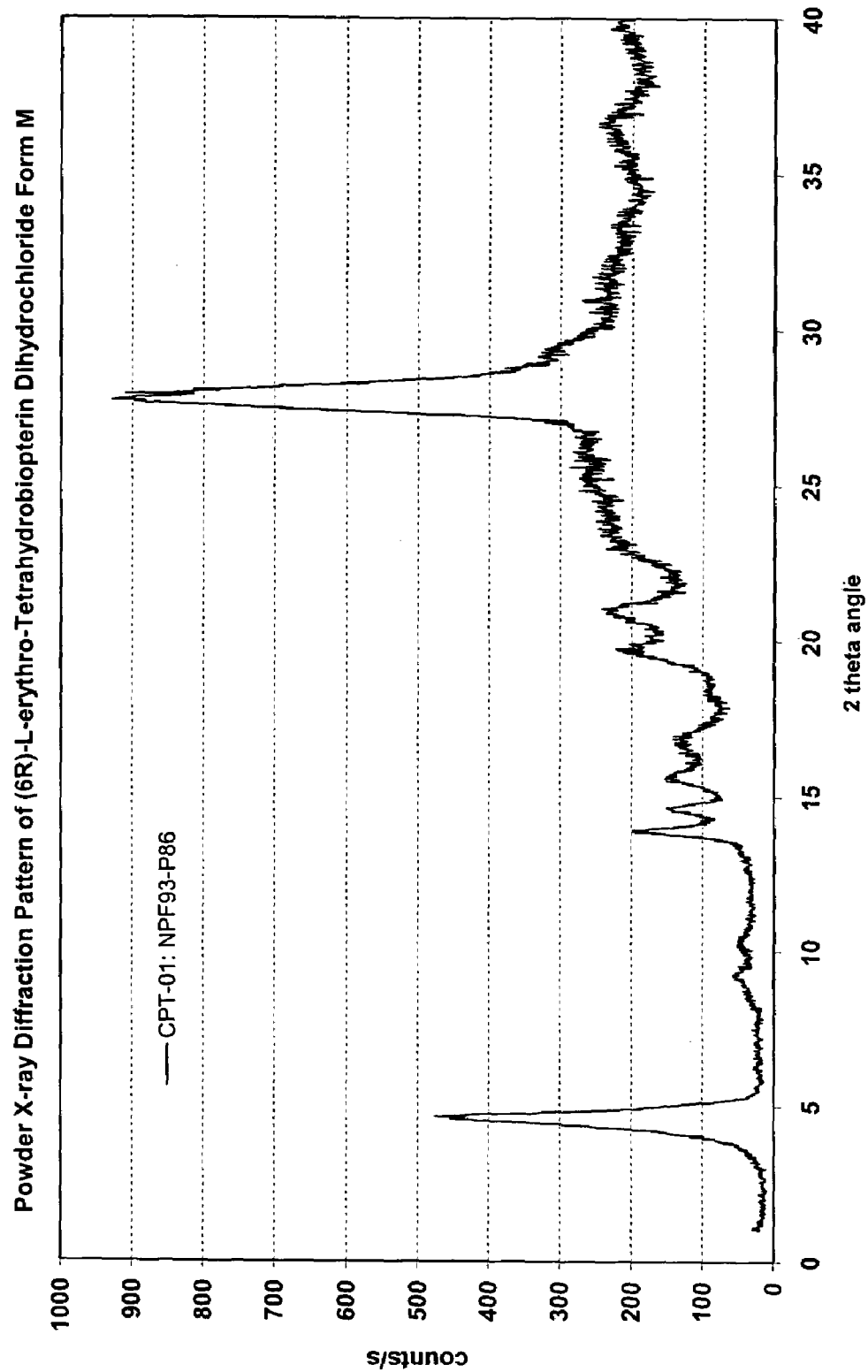
FIG. 14 is a powder X-ray diffraction pattern of (6R)-BH4 Form M.

Form M exhibits a characteristic X-ray powder diffraction pattern with characteristic peaks expressed in d-values (Å) at: 18.9 (s), 6.4 (m), 6.06 (w), 5.66 (w), 5.28 (w), 4.50 (w), 4.23 (w), and 3.22 (vs). FIG. 14 is a graph of the characteristic X-ray diffraction pattern exhibited by solvate form M of (6R)-L-erythro-tetrahydrobiopterin dihydrochloride.

Ethanol solvate form M may be obtained by dissolution of L-erythro-tetrahydrobiopterin dihydrochloride in ethanol and evaporation of the solution under nitrogen at ambient temperature, i.e., between 10° C. and 40° C. Form M may also be obtained by drying of form G under a slight flow of dry nitrogen at a rate of about 20 to 100 ml/min. Depending on the extent of drying under nitrogen, the remaining amount of ethanol may be variable, i.e., from about 3% to 13%.

Solvate Form N

It has been found that another solvate crystal form of (6R)-L-erythro-tetrahydrobiopterin dihydrochloride is a stable prefered form of BH4 for use in a pharmaceutical preparation described herein, which shall be referred to herein as "form N," or "hydrate N." Form N may contain in total up to 10% of isopropanol and water, which suggests that form N is a slightly hygroscopic isopropanol solvate. Form N may be obtained through washing of form D with isopropanol and subsequent drying in vacuum at about 30° C. Form N is especially suitable as intermediate and starting material to produce stable polymorph forms. Polymorph form N can be prepared as a solid powder with desired medium particle size range which is typically ranging from 1 μm to about 500 μm.

Figure 15:
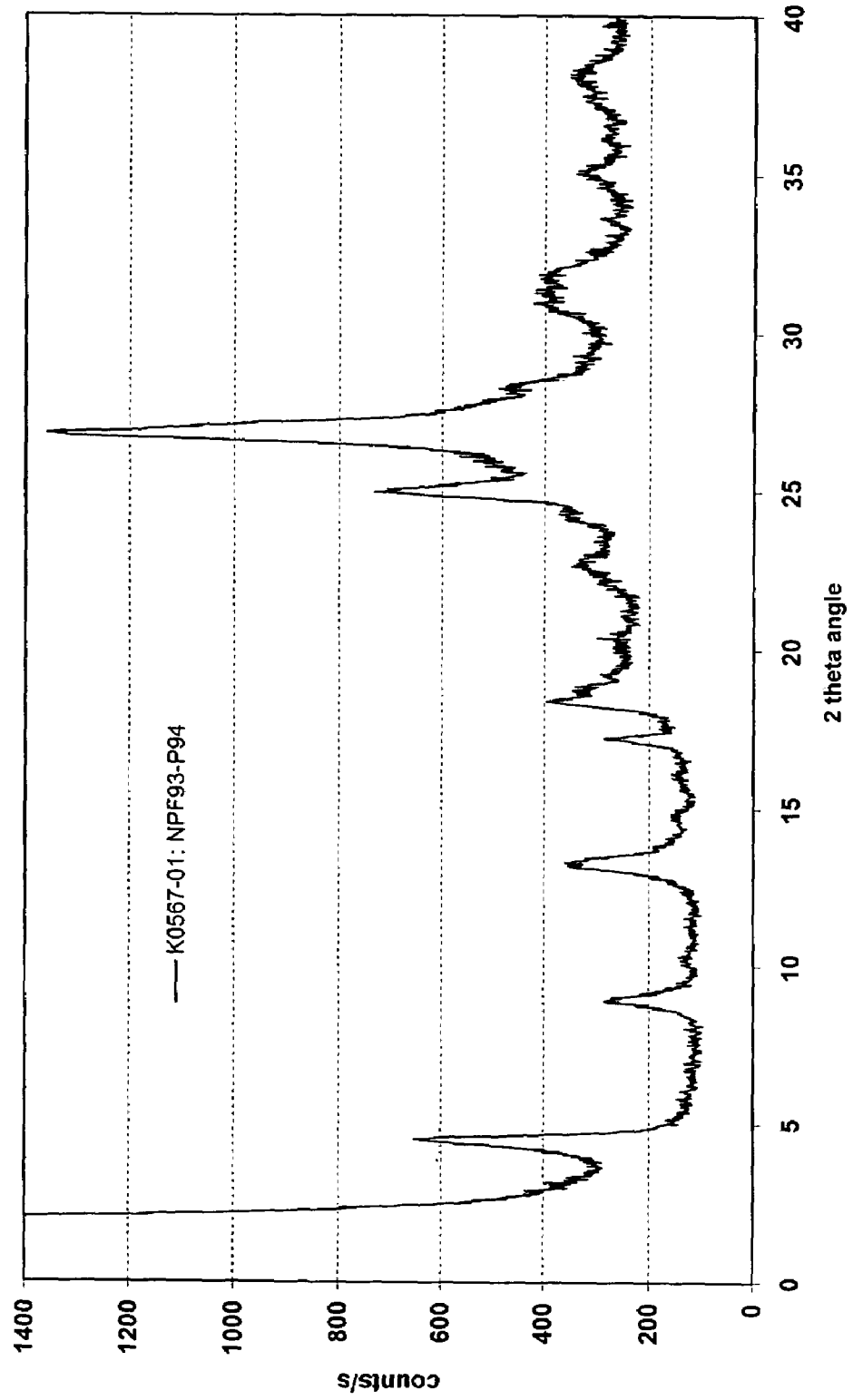
FIG. 15 is a powder X-ray diffraction pattern of (6R)-BH4 Form N.

Form N exhibits a characteristic X-ray powder diffraction pattern with characteristic peaks expressed in d-values (Å) at: 19.5 (m), 9.9 (w), 6.7 (w), 5.15 (w), 4.83 (w), 3.91 (w), 3.56 (m), 3.33 (vs), 3.15 (w), 2.89 (w), 2.81 (w), 2.56 (w), and 2.36 (w). FIG. 15 is a graph of the characteristic X-ray diffraction pattern exhibited by solvate form N of (6R)-L-erythro-tetrahydrobiopterin dihydrochloride.

The isopropanol form N may be obtained by dissolution of L-erythro-tetrahydrobiopterin dihydrochloride in 4.0 ml of a mixture of isopropanol and water (mixing volume ratio for example 4:1). To this solution is slowly added isopropanol (IPA, for example about 4.0 ml) and the resulting suspension is cooled to 0° C. and stirred for several hours (e.g., about 10 to 18 hours) at this temperature. The suspension is filtered and the solid residue washed with isopropanol at room temperature. The obtained crystalline material is then dried at ambient temperature (e.g., about 20 to 30° C.) and reduced pressure (about 2 to 10 mbar) for several hours (e.g., about 5 to 20 hours). TG-FTIR shows a weight loss of 9.0% between 25 to 200° C., which is attributed to both isopropanol and water. This result suggests that form N can exist either in form of an isopropanol solvate, or in form of mixed isopropanol solvate/hydrate, or as an non-solvated form containing a small amount of water.

For the preparation of the polymorph forms, there may be used crystallization techniques well known in the art, such as stirring of a suspension (phase equilibration in), precipitation, re-crystallization, evaporation, solvent like water sorption methods or decomposition of solvates. Diluted, saturated or super-saturated solutions may be used for crystallization, with or without seeding with suitable nucleating agents. Temperatures up to 100° C. may be applied to form solutions. Cooling to initiate crystallization and precipitation down to −100° C. and preferably down to −30° C. may be applied. Meta-stable polymorphs or pseudo-polymorphic forms can be used to prepare solutions or suspensions for the preparation of more stable forms and to achieve higher concentrations in the solutions.

It was surprisingly found that hydrate form D is the most stable form under the hydrates and forms B and D are especially suitable to be used in pharmaceutical formulations. Forms B and D presents some advantages like an aimed manufacture, good handling due to convenient crystal size and morphology, very good stability under production conditions of various types of formulation, storage stability, higher solubility, and high bio-availability. Accordingly, in a method and/or a composition disclosed herein the form of BH4 present in a mixture is preferably a stabilized crystal form of BH4 an is selected from the group consisting of crystal polymorph form A, crystal polymorph form B, crystal polymorph form F, crystal polymorph form J, crystal polymorph form K, crystal hydrate form C, crystal hydrate form D, crystal hydrate form E, crystal hydrate form H, crystal hydrate form O, solvate crystal form G, solvate crystal form I, solvate crystal form L, solvate crystal form M, solvate crystal form N, and combinations thereof. More preferably, the form of BH4 is for use in a composition and method disclosed herein is pharmaceutical composition including polymorph form B and/or hydrate form D of (6R)-L-erythro-tetrahydrobiopterin dihydrochloride and a pharmaceutically acceptable carrier or diluent.

The crystal forms of (6R)-L-erythro-tetrahydrobiopterin dihydrochloride may be used together with folic acid or tetrahydrofolic acid or their pharmaceutically acceptable salts such as sodium, potassium, calcium or ammonium salts, each alone or additionally with arginine. The weight ratio of crystal forms:folic acids or salts thereof:arginine may be from about 1:10:10 to about 10:1:1.

VI. Pharmaceutical Formulations

The formulations described herein are preferably administered as oral formulations. Oral formulations are preferably solid formulations such as capsules, tablets, pills and troches, or liquid formulations such as aqueous suspensions, elixirs and syrups. The various form of BH4 described herein can be directly used as powder (micronized particles), granules, suspensions or solutions, or it may be combined together with other pharmaceutically acceptable ingredients in admixing the components and optionally finely divide them, and then filling capsules, composed for example from hard or soft gelatin, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents, antioxidants and carriers for the various formulation types. Nonlimiting examples of binders useful in a composition described herein include gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,1-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan.

Nonlimiting examples of excipients useful in a composition described herein include phosphates such as dicalcium phosphate. Nonlimiting examples of lubricants use in a composition described herein include natural or synthetic oils, fats, waxes, or fatty acid salts such as magnesium stearate.

Surfactants for use in a composition described herein can be anionic, anionic, amphoteric or neutral. Nonlimiting examples of surfactants useful in a composition described herein include lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid; 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Nonlimiting examples of sweetening agents useful in a composition described herein include sucrose, fructose, lactose or aspartame. Nonlimiting examples of flavoring agents for use in a composition described herein include peppermint, oil of wintergreen or fruit flavors such as cherry or orange flavor. Nonlimiting examples of coating materials for use in a composition described herein include gelatin, wax, shellac, sugar or other biological degradable polymers. Nonlimiting examples of preservatives for use in a composition described herein include methyl or propylparabens, sorbic acid, chlorobutanol, phenol and thimerosal.

The hydrate form D described herein may also be formulated as effervescent tablet or powder, which disintegrate in an aqueous environment to provide a drinking solution. A syrup or elixir may contain the polymorph described herein, sucrose or fructose as sweetening agent a preservative like methylparaben, a dye and a flavoring agent.

Slow release formulations may also be prepared from the polymorph described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

While individual needs vary, determination of optimal ranges of effective amounts of each component is within the skill of the art. Typical dosages of the BH4 comprise about 1 to about 20 mg/kg body weight per day, which will usually amount to about 5 (1 mg/kg×5 kg body weight) to 3000 mg/day (30 mg/kg×100 kg body weight). Such a dose may be administered in a single dose or it may be divided into multiple doses. While continuous, daily administration is contemplated, it may be desirable to ceases the BH4 therapy when the symptoms of Phe levels are reduced to below a certain threshold level. Of course, the therapy may be reinitiated in the event that Phe levels rise again.

It is understood that the suitable dose of a composition according to the present invention will depend upon the age, health and weight of the recipient, kind of concurrent treatment, if any, frequency of treatment, and the nature of the effect desired (i.e., the amount of decrease in plasma Phe concentration desired). The frequency of dosing also is dependent on pharmacodynamic effects on Phe levels. If the effect lasts for 24 hours from a single dose. However, the most preferred dosage can be tailored to the individual subject, as is understood and determinable by one of skill in the art, without undue experimentation. This typically involves adjustment of a standard dose, e.g., reduction of the dose if the patient has a low body weight.

As discussed above, the total dose required for each treatment may be administered in multiple doses or in a single dose. The BH4 and the protein compositions may be administered alone or in conjunction with other therapeutics directed to the disease or directed to other symptoms thereof.

As is apparent from the disclosure presented herein, in a broad aspect the present application contemplates clinical application of a combination therapy comprising a first composition that contains a crystallized BH4 formulation, and a second composition that contains a medical protein formulation (e.g., PHENEX or the like). Therefore, the compositions should be formulated into suitable pharmaceutical compositions, i.e., in a form appropriate for in vivo applications in such combination therapies. Generally, this will entail preparing compositions that are essentially free of pyrogens, as well as other impurities that could be harmful to humans or animals. Preferably, the crystallized BH4 composition may be such that it can be added directly to the preexisting protein formulations used for the treatment of PKU.

One will generally desire to employ appropriate salts and buffers to render the BH4 suitable for uptake. Aqueous compositions of the present invention comprise an effective amount of the BH4 dissolved or dispersed in a pharmaceutically acceptable carrier or aqueous medium. Such compositions may be administered orally or via injection.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the medical protein formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin. The amino acids, minerals and vitamins in the supplement should be provided in amounts that provide the recommended daily doses of each of the components.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The active compositions of the present invention include classic pharmaceutical preparations of BH4 which have been discussed herein as well as those known to those of skill in the art. Protein formulas, such as, e.g., Phenex, also are known to those of skill in the art. Administration of these compositions according to the present invention will be via any common route for dietary supplementation. The protein is preferably administered orally, as is the BH4.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The BH4 compositions may be prepared as pharmaceutical forms suitable for injectable use. Such compositions include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The BH4 used in a composition described herein is preferably formulated as a dihydrochloride salt, however, it is contemplated that other salt forms of BH4 posses the desired biological activity, and consequently, other salt forms of BH4 can be used.

Compositions and methods for producing a stabilized tablet formulation are also disclosed in co-pending U.S. provisional application No. 60/629,189 filed Nov. 17, 2004, the entirety of which is hereby incorporated by reference.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'dibenzylethylenediamine, chloroprocaine, choline, diethanolamine, dicyclohexylamine, ethylenediamine, N methylglucamine, and procaine.

Pharmaceutically acceptable acid addition salts include inorganic or organic acid salts. Examples of suitable acid salts include the hydrochlorides, acetates, citrates, salicylates, nitrates, phosphates. Other suitable pharmaceutically acceptable salts are well known to those skilled in the art and include, for example, acetic, citric, oxalic, tartaric, or mandelic acids, hydrochloric acid, hydrobromic acid, sulfuric acid or phosphoric acid; with organic carboxylic, sulfonic, sulfo or phospho acids or N substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4 aminosalicylic acid, 2 phenoxybenzoic acid, 2 acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2 hydroxyethanesulfonic acid, ethane 1,2 disulfonic acid, benzenesulfonic acid, 4 methylbenzenesulfoc acid, naphthalene 2 sulfonic acid, naphthalene 1,5 disulfonic acid, 2 or 3 phosphoglycerate, glucose 6 phosphate, N cyclohexylsulfamic acid (with the formation of cyclamates), or with other acid organic compounds, such as ascorbic acid.

Specifically, BH4 salts with inorganic or organic acids are preferred. Nonlimiting examples of alternative BH4 salts forms includes BH4 salts of acetic acid, citric acid, oxalic acid, tartaric acid, fumaric acid, and mandelic acid.

The frequency of BH4 dosing will depend on the pharmacokinetic parameters of the agent and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435 1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of established assays for determining blood levels of Phe in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Clinical Evaluation with 6R-Tetrahydrobiopterin

The following example provides guidance on the parameters to be used for the clinical evaluation BH4 in the therapeutic methods of the present invention. As discussed herein throughout, BH4 will be used in the treatment of HPA including HPA, mild phenylketonuria (PKU) and classic PKU. Clinical trials will be conducted which will provide an assessment of daily oral doses of BH4 for safety, pharmacokinetics, and initial response of both surrogate and defined clinical endpoints. The trial will be conducted for a minimum, but not necessarily limited to, 6 weeks to collect sufficient safety information for 30 evaluable patients.

The initial dose for the trials will vary from about 10 to about 20 mg/kg. In the event that this dose does not produce a reduction in excess plasma phenylalanine (Phe) levels in a patient, or produce a significant direct clinical benefit measured as an ability to increase daily oral Phe intake without increases in plasma Phe levels, the dose should be increased as necessary, and maintained for an additional minimal period of, but necessarily limited to, 6 weeks to establish safety and to evaluate further efficacy. Lower doses, e.g., doses of between 5 to 10 mg/kg also are contemplated.

Measurements of safety will include adverse events, allergic reactions, complete clinical chemistry panel (kidney and liver function), urinalysis, and CBC with differential. In addition, other parameters including the reduction in levels of blood Phe levels, neuropsychological and cognitive testing, and global assessments also will be monitored. The present example also contemplates the determination of pharmacokinetic parameters of the drug in the circulation, and general distribution and half-life of 6R-BH4 in blood. It is anticipated that these measures will help relate dose to clinical response.

Methods

Patients who have elevated levels of plasma Phe will undergo a baseline a medical history and physical exam, neuropsychological and cognitive testing, a standard set of clinical laboratory tests (CBC, Panel 20, CH50, UA), levels of urinary pterins, dihydropteridine reductase (DHPR) levels, and a fasting blood (plasma) panel of serum amino acids. The proposed human dose of 10 to about 20 mg/kg BH4 will be administered divided in one to three daily doses. The patient will be followed closely with weekly visits to the clinic. Patients will return to the clinic for a complete evaluation one week after completing the treatment period. Should dose escalation be required, the patients will follow the same schedule outlined above. Safety will be monitored throughout the trial.

Enrolled patients will be randomized to receive BH4 or a placebo. After an initial two to four-week period all study participants will be placed on a controlled diet with a limited Phe intake for a total of four to six weeks. After completing the first two to four weeks on dietary restriction, all study participants will be crossed-over in their randomization and will followed for an additional two to four weeks. Phe blood levels and other biochemical parameters will be followed closely at the end of each period. Evaluation of neuropsychological outcomes will include measurements of sustained attention; working memory; and ability to perform complex operations. Patients who complete the trial, and who benefited from therapy by showing a beneficial decrease plasma Phe levels, will be offered continued BH4 therapy thorough an extended protocol for as long as safety and efficacy conditions warrant it, or until BLA approval.

Diagnosis and Inclusion/Exclusion Criteria

The patient may be male or female, aged twelve years or older with a documented diagnosis of HPA or mild PKU confirmed by genetic testing and evidence of elevated Phe levels in blood. The study will include HPA or PKU patients who do not accurately follow dietary control. Female patients of childbearing potential must have a negative pregnancy test (urine β-hCG) just prior to each dosing and must be advised to use a medically accepted method of contraception throughout the study. A patient will be excluded from this study if the patient has evidence of a primary BH4 deficiency, has previously received multiple doses of BH4 for more than 1 week of treatment; is pregnant or lactating; has received an investigational drug within 30 days prior to study enrollment; or has a medical condition, serious intercurrent illness, or other extenuating circumstance that may significantly decrease study compliance.

Dose, Route and Regimen

Patients will receive BH4 at a dose of 5-10 mg/kg per day. In the event that Phe blood levels are not decreased by a reasonable amount and no clinical benefit is observed, the dose will be increased as necessary. Dose escalation will occur only after all patients have undergone at least 2 weeks of therapy. The daily BH4 dosage will be administered orally as liquid, powder, tablets or capsules. The total daily dose may be given as a single dose or perhaps divided in two or three daily doses. The patients will be monitored clinically as well as for any adverse reactions. If any unusual symptoms are observed, study drug administration will be stopped immediately, and a decision will be made about study continuation.

Dietary Intervention

Following the initial randomization and two week treatment period, all study participants will undergo dietary counseling and will follow a standard Phe-restricted diet complemented with Phe-specific medical foods for a total of four to six weeks. Diets will be managed at home and dietary intake will be recorded in daily logs. Analyses of the intakes of nutrients and medical foods and the percent of Recommended Dietary Intakes (RDI) will be compared among the treatment groups.

BH4 Safety

BH4 therapy will be determined to be safe if no significant acute or chronic drug reactions occur during the course of the study. The longer-term administration of the drug will be determined to be safe if no significant abnormalities are observed in the clinical examinations, clinical labs, or other appropriate studies.

Example 2

Preparation of Stabilized Crystallized form of BH4

U.S. Provisional Patent Application Ser. No. 60/520,377, entitled "Polymorphs of (6R)-L-erythro-tetrahydrobiopterin dihydrochloride" filed on Nov. 17, 2003 in the name of Applicants Rudolf MOSER, of Schaffhausen, Switzerland and Viola GROEHN of Dachsen, Switzerland and assigned Merck-Eprova internal reference number 216, and U.S. patent application Ser. No. 10/990,316, entitled "Polymorphs of (6R)-L-erythro-tetrahydrobiopterin dihydrochloride" filed concurrently herewith on Nov. 17, 2004 in the name of Applicants Rudolf MOSER, of Schaffhausen, Switzerland and Viola GROEHN of Dachsen, Switzerland and assigned Merck-Eprova internal reference number 216/US CIP (both of the Moser et al. applications are collectively referred to herein as the "Moser Applications" and both are incorporated herein by reference in their entireties. The examples of that specification describe X ray and Raman spectra studies to characterize the polymorphs of BH4. Each of the BH4 compositions of that application may be used in the treatment methods described herein. The following description provides additional background and a brief characterization of some of those exemplary compositions.

Results obtained during development of (6R)-L-erythro-tetrahydrobiopterin dihydrochloride (see the Moser Applications) indicated that the compound may possess polymorphic forms. The continued interest in this area requires an efficient and reliable method for the preparation of individual polymorphs of (6R)-L-erythro-tetrahydrobiopterin dihydrochloride and controlled crystallization conditions to provide polymorphs, which are preferably stable and easily to handle and to process in the manufacture and preparation of formulations.

Crystallization techniques well known in the art for producing drug crystals are used to prepare the prepare the polymorph forms. Such techniques include, but are not limited to, techniques such as suspension, precipitation, re-crystallization, evaporation, solvent like water sorption methods or decomposition of solvates. Diluted, saturated or super-saturated solutions of the BH4 may be used for crystallization, with or without seeding with suitable nucleating agents. Temperatures up to 150° C. may be applied to form solutions of the drug. Cooling to initiate crystallization and precipitation down to −100° C. and preferably down to −30° C. may be applied. Metastable polymorph or pseudo-polymorph forms can be used to prepare solutions or suspensions for the preparation of more stable forms and to achieve higher concentrations in the solutions.

As discussed in the Moser Applications, the polymorph form may be obtained by crystallization of the BH4 from polar solvent mixtures. The Moser Applications also describes a process for the preparation of polymorph form of (6R)-L-erythro-tetrahydrobiopterin dihydrochloride, comprising dissolution, optionally at elevated temperatures, of a solid lower energy form than the claimed form of (6R)-L-erythro-tetrahydrobiopterin dihydrochloride in a polar solvent mixture, addition of seeds to the solution, cooling the obtained suspension and isolation of the formed crystals.

Dissolution may be carried out at room temperature or up to 70° C., More preferably the dissolution is carried out at temperatures up to 50° C. The starting material may be added to the final solvent mixture for dissolution, or alternatively the starting material first may be dissolved in water and other solvents may than be added both or one after the other solvent. The solution of the BH4 is preferably stirred. Cooling may mean temperatures down to −80° C., preferably down to −40° C. to 0° C. In some embodiments, in order to initiate the crystallization of the BH4 polymorph, the solution may be seeded. Suitable seeds may include a portion of the polymorph form from another batch of crystals, or crystals having a similar or identical morphology. After isolation, the crystalline form can be washed with acetone or tetrahydrofurane and dried using techniques commonly used for drying drug crystals.

The polymorph forms of BH4 described in the Moser Applications are a very stable crystalline form of the drug.

The polymorph form can be easily filtered off, dried and ground to particle sizes desired for pharmaceutical formulations. These outstanding properties renders this polymorph form especially feasible for pharmaceutical application. The stability of the polymorph form of BH4 was determined after the BH4×2HCl (the polymorph form) had been stored for 8 months in a minigrip bag at 40° C. and 75% relative humidity. Quality was checked in different intervals throughout the 8 month period by HPLC. After 8 months, the quality and stability of the polymorph was surprisingly similar to the stability seen at time zero:

|  | 0 months (at the beginning) | after 1 week | after 1 month | after 3 months | after 8 months |
|---|---|---|---|---|---|
| HPLC [% area] | 98.4 | 99.4 | 98.3 | 99.1 | 98.1 |

Accordingly, the Moser Applications provides descriptions of a pharmaceutical compositions comprising a polymorph form of (6R)-L-erythro-tetrahydrobiopterin dihydrochloride and a pharmaceutically acceptable carrier or diluent. Such compositions will be useful in the therapeutic methods described herein.

In addition to the Moser Applications, those of skill in the art also are referred to U.S. Pat. Nos. 6,596,721; 6,441,168; and 6,271,374 which describe various methods and compositions for producing stable crystalline salts of 5-methyltetrahydrofolic acid and methods and compositions for producing stable forms of 6R tetrahdrofolic acid and methods and compositions for producing stable forms of 6S and 6R tetrahdrofolic acid. Each of these patents are incorporated herein by reference in their entirety as generally teaching methods of producing crystalline forms of agents and techniques for characterizing such agents. Such methods may be used in producing stable forms of BH4 for use as pharmaceutical compositions in the treatment methods taught herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 3

Administration of Tetrahydrobiopterin to Humans with Elevated Serum Phe Levels

An open label, single and multiple dose study was conducted in a total of 20 patients to demonstrate the safety and efficacy of tetrahydrobiopterin in humans with elevated blood levels of phenylalanine (>600 µmol/L). Criteria for inclusion in the study included (1) baseline blood Phe levels of >600 µmol/L, (2) age of at least 8 years. Criteria for exclusion from the study included (1) pregnancy or breastfeeding, (2) concurrent diseases or conditions that require medication or treatment, (3) concurrent treatment with any drug known to inhibit folate synthesis, and (4) treatment with any investigational drug within 30 days. Each of the patients also was identified as having a mutation in the phenylalanine hydroxylase (PAH) gene. Study subjects underwent baseline assessments, including medical history with assessment of phenylketonuria (PKU) or hyperphenylalaninemia (HPA) related signs and symptoms, physical examinations, vital signs, serum amino acid (i.e., phenylalanine, tyrosine, and tryptophan) blood levels, and routine laboratory tests (chemistry, hematology, and urinalysis) before inclusion in the study.

The drug tested was (6R)-5,6,7,8-tetrahydrobiopterin, also known as 2-amino-6-(1,2-dihydroxypropyl)-5,6,7,8-tetrahydro-3H-pteridin-4-one tetrahydrobiopterin, or sapropterin (BH4 or 6R-BH4. The drug was obtained in 10 mg or 50 mg oral tablets from Schircks Laboratories, Switzerland (product no. 11.212 (6R)-5,6,7,8-Tetrahydro-L-biopterin dihydrochloride). The half-life of the Schircks 6R-BH4 dihydrochloride salt is approximately 3.5 hours.

Drugs known to inhibit folate synthesis such as bactrim, methotrexate, or 5-FU were not permitted to be administered during the study. Before initiation of 6R-BH4 dosing, a 7 day washout period was required for any drugs known to inhibit folate synthesis. No investigational drugs were permitted to be taken during study participation or within 30 days prior to study enrollment.

Within a maximum of 4 weeks following the completion of baseline assessments, eligible subjects began the first stage of the study. Single ascending doses of 10 mg/kg, 20 mg/kg and 40 mg/kg of 6R-BH4 were administered orally, with a washout period of at least 7 days between each dose, and subjects were monitored 24 hours after each dose. Subjects underwent a safety assessment and blood amino acid (i.e, phenylalanine, tyrosine, and tryptophan) level measurements before and 24 hours after each 6R-BH4 dose. Blood pressure was measured 30 minutes and 1 hour after each dose. Safety assessments included physical examinations, vital signs, serial assessment of PKU or HPA related signs and symptoms, recording of adverse events, and monitoring of changes in laboratory parameters (chemistry, hematology, and urinalysis). Subjects were instructed to continue their usual diet without any modification, and to record daily intake of food and beverages throughout the study.

After the first stage of the study was completed, subjects entered the second stage of the study, during which they received 10 mg/kg of 6R-BH4 daily in an oral dosage form, for a total of 7 days. After a washout period of at least 7 days, each subject received 20 mg/kg of 6R-BH4 daily for a total of 7 days. During the second stage of the study, subjects were monitored before dosing, at 24 and 72 hours after first dose, and on the 7th day of dosing at each of the two dose levels. Monitoring included a safety assessment as described above, measurement of serum blood amino acid (i.e, phenylalanine, tyrosine, and tryptophan) levels and evaluation of phenylalanine and tyrosine oral intake. Subjects were instructed to continue their usual diet without any modification, and to record daily intake of food and beverages throughout the study.

After a single dose of 6R-BH4 (10 mg/kg), blood Phe declined 10%±0.26% from baseline. Single doses of 6R-BH4 at 20 mg/kg and 40 mg/kg showed mean declines of 17%±0.28% and 27%±0.25% respectively. The reduction in blood Phe levels appeared to be dose dependent.

Figure 16:
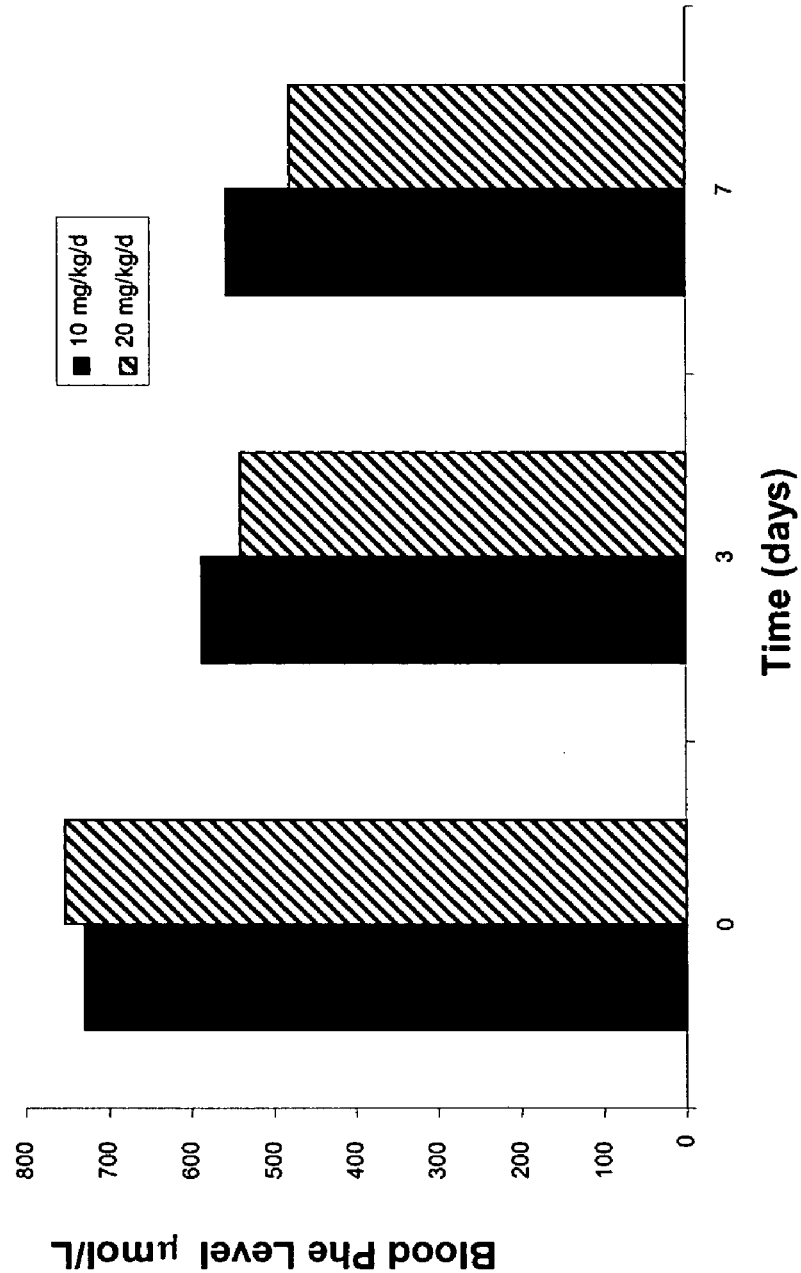
FIG. 16 is a mean blood phenylalanine level comparison at time zero, 3 days, and 7 days for multiple daily BH4 doses of 10 mg/kg/d and 20 mg/kg/d.
Figure 17:
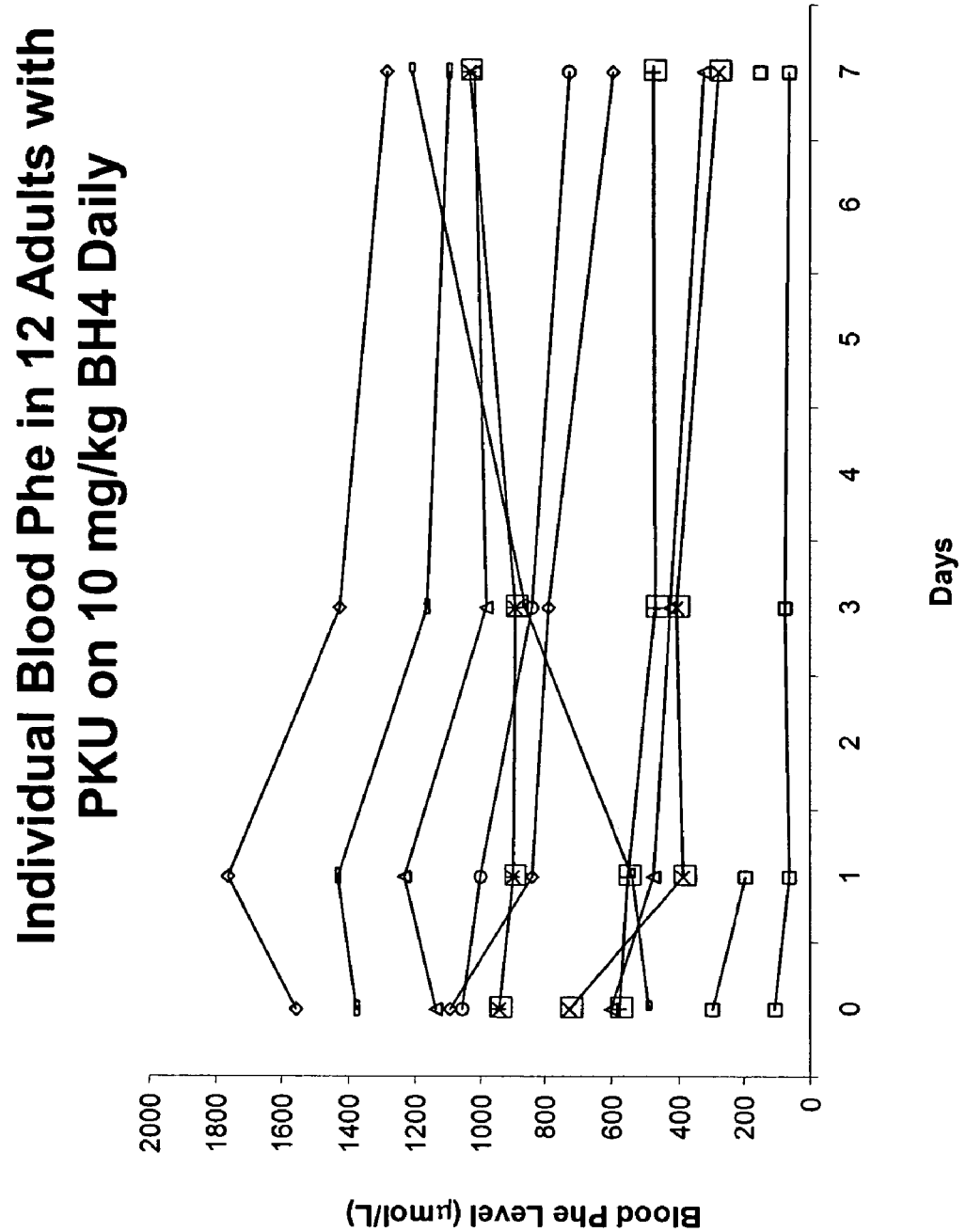
FIG. 17 is a comparison of daily individual blood phenylalanine levels for 12 adults having PKU and taking 10 mg/kg/d over 7 days.
Figure 18:
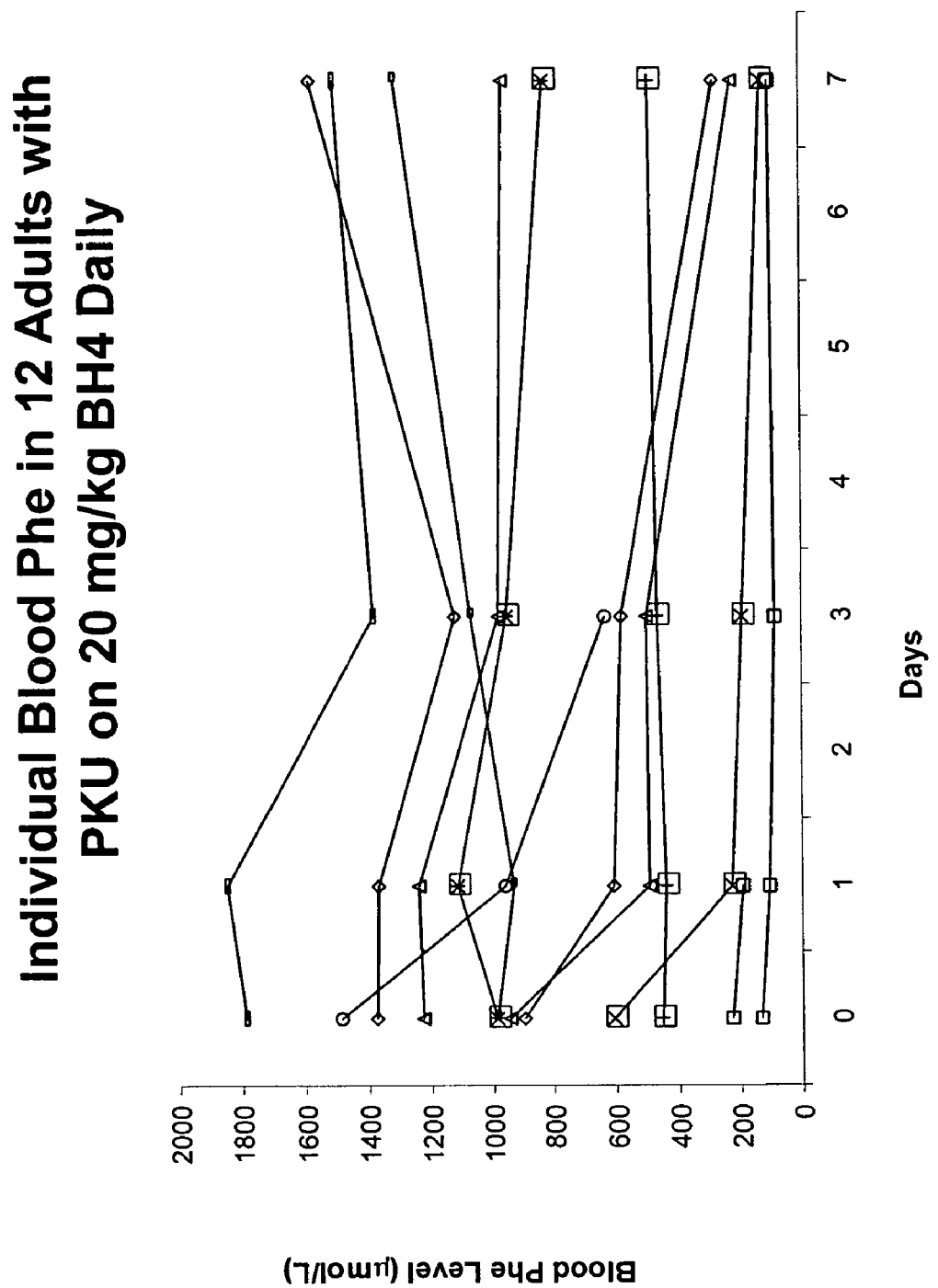
FIG. 18 is a comparison of daily individual blood phenylalanine levels for 12 adults having PKU and taking 20 mg/kg/d over 7 days.
Figure 19:
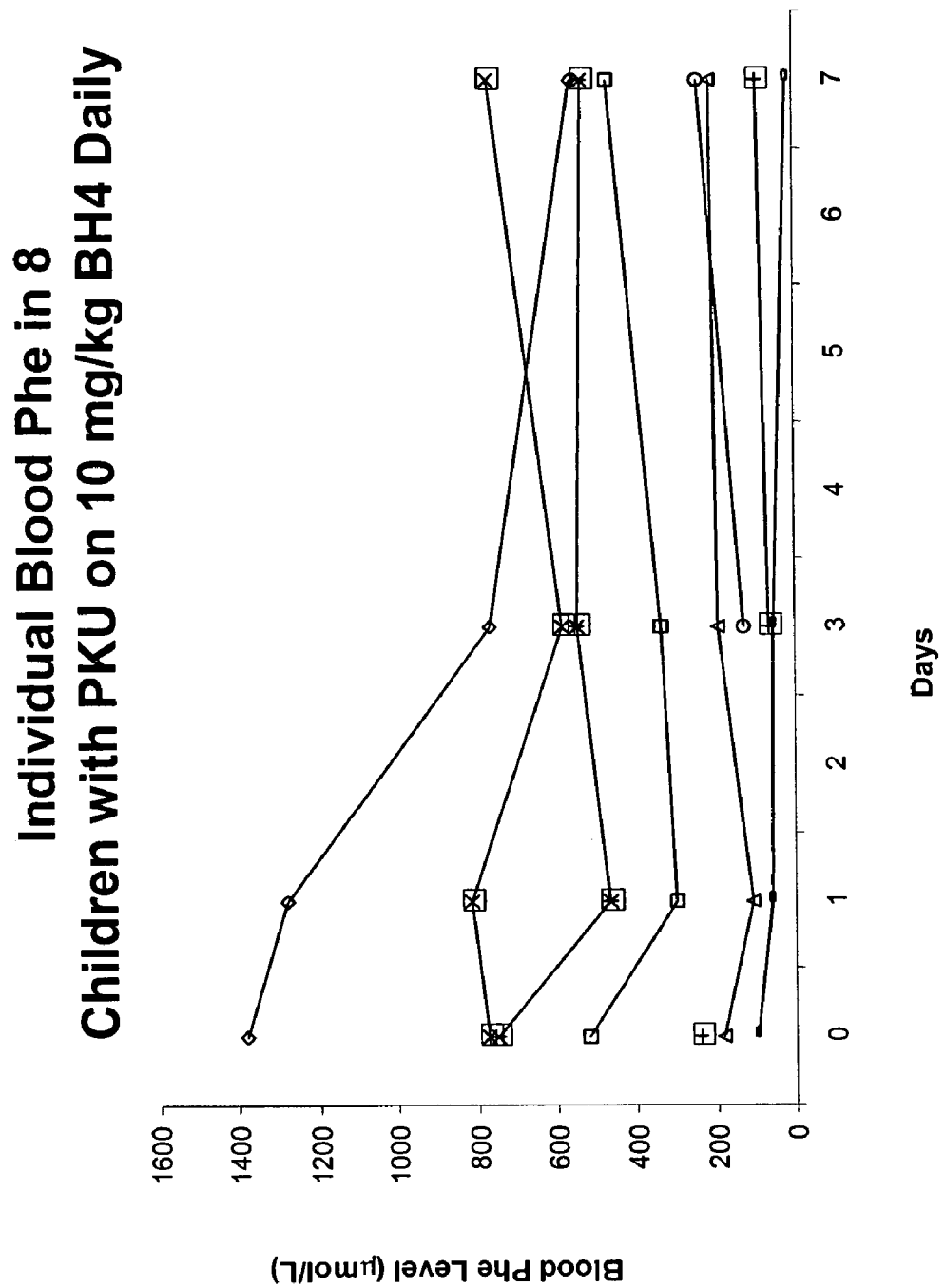
FIG. 19 is a comparison of daily individual blood phenylalanine levels for 8 children having PKU and taking 10 mg/kg/d over 7 days.
Figure 20:
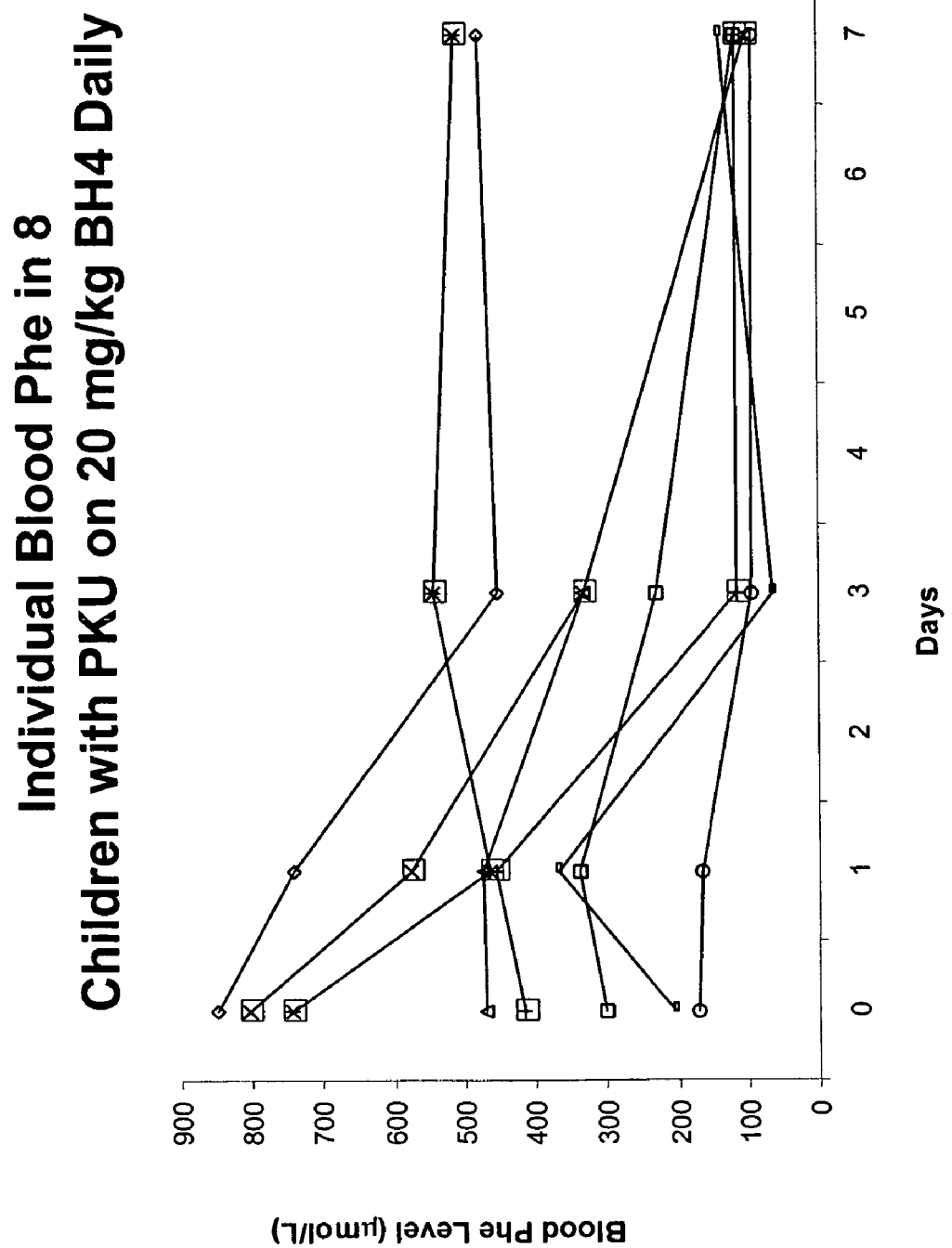
FIG. 20 is a comparison of daily individual blood phenylalanine levels for 8 children having PKU and taking 20 mg/kg/d over 7 days.

FIG. 16 shows mean blood phenylalanine level after 10 and 20 mg/kg 6R-BH4 daily for 7 days, in the 14 of 20 patients who responded to treatment. For the purposes of this study, a decline in blood Phe levels of 30% was considered to be "responsive", although patients who exhibit less of a decline would still benefit from BH4 treatment. The seven-day trial showed a sustained decrease in blood Phe concentration in 70% of the patients (14/20) taking 20 mg/kg. Of those 14 patients, 10 (71%) responded favorably to 10 mg/kg/day. Blood tyrosine was observed to increase in some but not all patients; some patients had increases of >80% from baseline tyrosine levels. The individual blood Phe responses to multiple doses of 10 mg/kg BH4 are shown in 11 adults (FIG. 17) and 9 children (FIG. 19). The individual blood Phe responses to multiple doses of 20 mg/kg BH4 are shown in 11 adults (FIG. 18) and in 9 children (FIG. 20).

Thus, a single-dose loading test was inadequate to identify patients who responded to BH4 treatment with a reduction in blood Phe level of 30% or more. A 7-day loading test successfully identified a high percentage of responsive patients. The 20 mg/kg, 7-day loading test with 6R-BH4 identified 70% of the PKU patients that responded to 20 mg/kg of BH4. Of the 14 responders, 71% also showed a 30% or greater reduction in blood Phe level with the lower dose of 10 mg/kg 6R-BH4.

The references cited herein throughout, to the extent that they provide exemplary procedural or other details supplementary to those set forth herein, are all specifically incorporated herein by reference.

What is claimed is:

1. A method for treating a subject with hyperphenylalaninemia due to tetrahydrobiopterin-responsive phenylketonuria, comprising administering to said subject a therapeutically effective total daily dosage of tetrahydrobiopterin (BH4) or pharmaceutically acceptable salt thereof, wherein the administering is multiday, oral, and only once per day, and wherein the administering does not achieve controlled release of the BH4 in the gastrointestinal tract.

2. The method of claim 1, wherein the administering is for at least 7 days.

3. The method of claim 1, wherein the subject is administered BH4 for at least 2 weeks.

4. The method of claim 3, wherein said subject is administered BH4 for at least 6 weeks.

5. The method of claim 1, wherein said subject suffers from severe phenylketonuria, moderate phenylketonuria, or mild phenylketonuria.

6. The method of claim 5, wherein said subject suffers from severe phenylketonuria.

7. The method of claim 5, wherein said subject suffers from mild phenylketonuria.

8. The method of claim 5, wherein said subject has been diagnosed as having a mutant phenylalanine hydroxylase (PAH).

9. The method of claim 8, wherein said mutant PAH comprises a mutation in the catalytic domain of PAH.

10. The method of claim 8, wherein said mutation comprises one or more mutations selected from the group consisting of F39L, L48S, I65T, R68S, A104D, S110C, D129G, E178G, V190A, P211T, R241C, R261Q, A300S, L308F, A313T, K320N, A373T, V388M E390G, A395P, P407S, and Y414C.

11. The method of claim 5, wherein said subject has a plasma phenylalanine concentration of greater than 180 μM prior to treatment with BH4.

12. The method of claim 5, wherein said subject has a plasma phenylalanine concentration of greater than 600 μM prior to treatment with BH4.

13. The method of claim 5, wherein said subject has a plasma phenylalanine concentration of greater than 1000 μM prior to treatment with BH4.

14. The method of claim 5, wherein said subject has a plasma phenylalanine concentration of greater than 1200 μM prior to treatment with BH4.

15. The method of claim 5, wherein said administration of BH4 decreases the plasma phenylalanine concentration of said subject to less than 600 μM.

16. The method of claim 5, wherein said administration of BH4 decreases the plasma phenylalanine concentration of said subject to less than 500 μM.

17. The method of claim 5, wherein said administration of BH4 decreases the plasma phenylalanine concentration of said subject to less than 360 μM.

18. The method of claim 5, wherein said BH4 is administered in a daily dose of between about 1 mg/kg to about 30 mg/kg.

19. The method of claim 5, wherein said BH4 is administered in a daily dose of between about 5 mg/kg to about 30 mg/kg.

20. The method of claim 5, wherein said BH4 is administered as a crystallized form stable for at least 3 months at 40° C. and 75% relative humidity.

21. The method of claim 20, wherein said crystallized form of BH4 comprises at least 99.5% pure (6R)-5,6,7,8-tetrahydrobiopterin.

22. The method of claim 5, further comprising administering to said subject a protein-restricted diet.

23. The method of claim 22, wherein said protein-restricted diet is a phenylalanine-restricted diet wherein the total phenylalanine is restricted to less than 600 mg per day.

24. The method of claim 22, wherein said protein-restricted diet is a phenylalanine-restricted diet wherein the total phenylalanine is restricted to less than 300 mg per day.

25. The method of claim 22, wherein said subject is a pregnant female.

26. The method of claim 22, wherein said subject is an infant between the ages of 0 and 3 years of age.

27. The method of claim 22, wherein said subject is a female of child-bearing age that is contemplating pregnancy.

28. The method of claim 20, wherein said crystallized form of BH4 comprises purified polymorph B, wherein polymorph B, as a hydrochloride salt, exhibits an X-ray powder diffraction pattern with the following characteristic peaks expressed in d-values(A) 8.7 (vs), 5.63 (m), 4.76(m), 4.40 (m), 4.00 (s), 3.23 (s), 3.11 (vs), preferably 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), and 2.44 (w).

29. The method of claim 20, wherein said crystallized form of BH4 comprises purified polymorph A, wherein polymorph A, as a hydrochloride salt, exhibits an X-ray powder diffraction pattern with the following characteristic peaks expressed in d-values(A): 15.5 (vs), 12.0 (m), 6.7 (m), 6.5 (m), 6.3 (w), 6.1 (w), 5.96 (w), 5.49 (m), 4.89 (m), 3.79 (m), 3.70 (s), 3.48 (m), 3.45 (m), 3.33 (s), 3.26 (s), 3.22 (m), 3.18 (m), 3.08 (m), 3.02 (w), 2.95 (w), 2.87 (m), 2.79 (w), 2.70 (w).

30. The method of claim 20, wherein said crystallized form of BH4 comprises purified polymorph F, wherein polymorph F, as a hydrochloride salt, exhibits an X-ray powder diffraction pattern with the following characteristic peaks expressed in d-values(A): 17.1 (vs), 12.1 (w), 8.6 (w), 7.0 (w), 6.5 (w), 6.4 (w), 5.92 (w), 5.72 (w), 5.11 (w), 4.92 (m), 4.86 (w), 4.68 (m), 4.41 (w), 4.12 (w), 3.88 (w), 3.83 (w), 3.70 (m), 3.64 (w), 3.55 (m), 3.49 (s), 3.46 (vs), 3.39 (s), 3.33 (m), 3.31 (m), 3.27 (m), 3.21 (m), 3.19 (m), 3.09 (m), 3.02 (m), and 2.96 (m).

31. The method of claim 20, wherein said crystallized form of BH4 comprises purified polymorph J, wherein polymorph J, as a hydrochloride salt, exhibits an X-ray powder diffraction pattern with the following characteristic peaks expressed in d-values(A): 14.6 (m), 6.6 (w), 6.4 (w), 5.47 (w), 4.84 (w), 3.29 (vs), and 3.21 (vs).

32. The method of claim 20, wherein said crystallized form of BH4 comprises purified polymorph K, wherein polymorph K, as a hydrochloride salt, exhibits an X-ray powder diffraction pattern with the following characteristic peaks expressed in d-values(A): 14.0 (s), 9.4 (w), 6.6 (w), 6.4 (w), 6.3 (w), 6.1 (w), 6.0 (w), 5.66 (w), 5.33 (w), 5.13 (vw), 4.73 (m), 4.64 (m), 4.48 (w), 4.32 (vw), 4.22 (w), 4.08 (w), 3.88 (w), 3.79 (w), 3.54 (m), 3.49 (vs), 3.39 (m), 3.33 (vs), 3.13 (s), 3.10 (m), 3.05 (m), 3.01 (m), 2.99 (m), and 2.90 (m).

33. The method of claim 20, wherein said crystallized form of BH4 comprises purified hydrate C, wherein hydrate C, as a hydrochloride salt, exhibits an X-ray powder diffraction pattern with the following characteristic peaks expressed in d-values(A): 18.2 (m), 15.4 (w), 13.9 (vs), 10.4 (w), 9.6 (w), 9.1 (w), 8.8 (m), 8.2 (w), 8.0 (w), 6.8 (m), 6.5 (w), 6.05 (m), 5.77 (w), 5.64 (w), 5.44 (w), 5.19 (w), 4.89 (w), 4.76 (w), 4.70 (w), 4.41 (w), 4.25 (m), 4.00 (m), 3.88 (m), 3.80 (m), 3.59 (s), 3.50 (m), 3.44 (m), 3.37 (m), 3.26 (s), 3.19 (vs), 3.17 (s), 3.11 (m), 3.06 (m), 3.02 (m), 2.97 (vs), 2.93 (m), 2.89 (m), 2.83 (m), and 2.43 (m).

34. The method of claim 20, wherein said crystallized form of BH4 comprises purified hydrate D, wherein hydrate D, as a hydrochloride salt, exhibits an X-ray powder diffraction pattern with the following characteristic peaks expressed in d-values(A): 8.6 (s), 6.8 (w), 5.56 (m), 4.99 (m), 4.67 (s), 4.32 (m), 3.93 (vs), 3.88 (w), 3.64 (w), 3.41 (w), 3.25 (w), 3.17 (m), 3.05 (s), 2.94 (w), 2.92 (w), 2.88 (m), 2.85 (w), 2.80 (w), 2.79 (m), 2.68 (w), 2.65 (w), 2.52 (vw), 2.35 (w), 2.34 (w), 2.30 (w), and 2.29 (w).

35. The method of claim 20, wherein said crystallized form of BH4 comprises purified hydrate E, wherein hydrate E, as a hydrochloride salt, exhibits an X-ray powder diffraction pattern with the following characteristic peaks expressed in d-values(A): 15.4 (s), 6.6 (w), 6.5 (w), 5.95 (vw), 5.61 (vw), 5.48 (w), 5.24 (w), 4.87 (w), 4.50 (vw), 4.27 (w), 3.94 (w), 3.78 (w), 3.69 (m), 3.60 (w), 3.33 (s), 3.26 (vs), 3.16 (w), 3.08 (m), 2.98 (w), 2.95 (m), 2.91 (w), 2.87 (m), 2.79 (w), 2.74 (w), 2.69 (w), and 2.62 (w).

36. The method of claim 20, wherein said crystallized form of BH4 comprises purified hydrate H, wherein hydrate H, as a hydrochloride salt, exhibits an X-ray powder diffraction pattern with the following characteristic peaks expressed in d-values(A): 8.6 15.8 (vs), 10.3 (w), 8.0 (w), 6.6 (w), 6.07 (w), 4.81 (w), 4.30 (w), 3.87 (m), 3.60 (m), 3.27 (m), 3.21 (m), 3.13 (w), 3.05 (w), 2.96 (m), 2.89 (m), 2.82 (w), and 2.67 (m).

37. The method of claim 20, wherein said crystallized form of BH4 comprises purified hydrate O, wherein hydrate O, as a hydrochloride salt, exhibits an X-ray powder diffraction pattern with the following characteristic peaks expressed in d-values(A): 15.9 (w), 14.0 (w), 12.0 (w), 8.8 (m), 7.0 (w), 6.5 (w), 6.3 (m), 6.00 (w), 5.75 (w), 5.65 (m), 5.06 (m), 4.98 (m), 4.92 (m), 4.84 (w), 4.77 (w), 4.42 (w), 4.33 (w), 4.00 (m), 3.88 (m), 3.78 (m), 3.69 (s), 3.64 (s), 3.52 (vs), 3.49 (s), 3.46 (s), 3.42 (s), 3.32 (m), 3.27 (m), 3.23 (s), 3.18 (m), 3.15 (vs), 3.12 (m), 3.04 (vs), 2.95 (m), 2.81 (s), 2.72 (m), 2.67 (m), and 2.61 (m).

38. The method of claim 20, wherein said crystallized form of BH4 comprises purified solvate G, wherein solvate G, as a hydrochloride salt, exhibits an X-ray powder diffraction pattern with the following characteristic peaks expressed in d-values(A): 14.5 (vs), 10.9 (w), 9.8 (w), 7.0 (w), 6.3 (w), 5.74 (w), 5.24 (vw), 5.04 (vw), 4.79 (w), 4.41 (w), 4.02 (w), 3.86 (w), 3.77 (w), 3.69 (w), 3.63 (m), 3.57 (m), 3.49 (m), 3.41 (m), 3.26 (m), 3.17 (m), 3.07 (m), 2.97 (m), 2.95 (m), 2.87 (w), and 2.61 (w).

39. The method of claim 20, wherein said crystallized form of BH4 comprises purified solvate I, wherein solvate I, as a hydrochloride salt, exhibits an X-ray powder diffraction pattern with the following characteristic peaks expressed in d-values(A): 14.5 (m), 14.0 (w), 11.0 (w), 7.0 (vw), 6.9 (vw), 6.2 (vw), 5.30 (w), 4.79 (w), 4.44 (w), 4.29 (w), 4.20 (vw), 4.02 (w), 3.84 (w), 3.80 (w), 3.67 (vs), 3.61 (m), 3.56 (w), 3.44 (m), 3.27 (w), 3.19 (w), 3.11(s), 3.00 (m), 2.94 (w), 2.87 (w), and 2.80 (w).

40. The method of claim 20, wherein said crystallized form of BH4 comprises purified solvate L, wherein solvate L, as a hydrochloride salt, exhibits an X-ray powder diffraction pattern with the following characteristic peaks expressed in d-values(A): 14.1 (vs), 10.4 (w), 9.5 (w), 9.0 (vw), 6.9 (w), 6.5 (w), 6.1 (w), 5.75 (w), 5.61 (w), 5.08 (w), 4.71 (w), 3.86 (w), 3.78 (w), 3.46 (m), 3.36 (m), 3.06 (w), 2.90 (w), and 2.82 (w).

41. The method of claim 20, wherein said crystallized form of BH4 comprises purified solvate M, wherein solvate M, as a hydrochloride salt, exhibits an X-ray powder diffraction pattern with the following characteristic peaks expressed in d-values(A): 18.9 (s), 6.4 (m), 6.06 (w), 5.66 (w), 5.28 (w), 4.50 (w), 4.23 (w), and 3.22 (vs).

42. The method of claim 20, wherein said crystallized form of BH4 comprises purified solvate N, wherein solvate N, as a hydrochloride salt, exhibits an X-ray powder diffraction pattern with the following characteristic peaks expressed in d-values(A): 19.5 (m), 9.9 (w), 6.7 (w), 5.15 (w), 4.83(w), 3.91 (w), 3.56 (m), 3.33 (vs), 3.15 (w), 2.89 (w), 2.81 (w), 2.56 (w), and 2.36 (w).

43. The method of claim 1, wherein the BH4 is administered in a daily dose of about 10 mg/kg or more.

44. The method of claim 2, wherein the BH4 is administered in a daily dose of about 10 mg/kg or more.

45. The method of claim 3, wherein the BH4 is administered in a daily dose of about 10 mg/kg or more.

46. The method of claim 4, wherein the BH4 is administered in a daily dose of about 10 mg/kg or more.

* * * * *

UNITED STATES PATENT AND TRADEMARK OFFICE
CERTIFICATE OF CORRECTION

PATENT NO. : 7,566,714 B2  Page 1 of 1
APPLICATION NO. : 11/143887
DATED : July 28, 2009
INVENTOR(S) : Daniel I. Oppenheimer et al.

It is certified that error appears in the above-identified patent and that said Letters Patent is hereby corrected as shown below:

On the Title Page:

At field (73), "Biomarin" should be -- BioMarin --.

Signed and Sealed this

Twenty-third Day of March, 2010

David J. Kappos
*Director of the United States Patent and Trademark Office*